(12) United States Patent
Drewniak et al.

(10) Patent No.: US 9,243,255 B2
(45) Date of Patent: Jan. 26, 2016

(54) BACTERIAL STRAINS, PLASMIDS, METHOD OF PRODUCING BACTERIAL STRAINS CAPABLE OF CHEMOLITHOTROPHIC ARSENITES OXIDATION AND USES THEREOF

(71) Applicant: UNIWERSYTET WARSZAWSKI, Warsaw (PL)

(72) Inventors: Lukasz Drewniak, Skarzysko-Kamienna (PL); Aleksandra Sklodowska, Warsaw (PL); Monika Radlinska, Warsaw (PL); Martyna Ciezkowska, Minsk Mazowiecki (PL)

(73) Assignee: UNIWERSYTET WARSZAWSKI, Warsaw (PL)

( * ) Notice: Subject to any disclaimer, the term of this patent is extended or adjusted under 35 U.S.C. 154(b) by 0 days.

(21) Appl. No.: 14/614,251

(22) Filed: Feb. 4, 2015

(65) Prior Publication Data

US 2015/0197758 A1    Jul. 16, 2015

Related U.S. Application Data

(60) Division of application No. 14/163,565, filed on Jan. 24, 2014, and a continuation-in-part of application No. PCT/IB2013/055577, filed on Jul. 8, 2013.

(30) Foreign Application Priority Data

Jul. 10, 2012   (PL) ........................................ 399883

(51) Int. Cl.
```
G01N 33/569    (2006.01)
C12N 15/74     (2006.01)
C12P 3/00      (2006.01)
C12R 1/01      (2006.01)
C12N 15/52     (2006.01)
C02F 3/34      (2006.01)
C02F 1/52      (2006.01)
C02F 101/10    (2006.01)
```
(52) U.S. Cl.
CPC .............. *C12N 15/743* (2013.01); *C02F 3/34* (2013.01); *C12N 15/52* (2013.01); *C12P 3/00* (2013.01); *C12R 1/01* (2013.01); *C02F 1/5236* (2013.01); *C02F 2101/103* (2013.01)

(58) Field of Classification Search
None
See application file for complete search history.

(56) References Cited

U.S. PATENT DOCUMENTS

2004/0072313 A1    4/2004  Banfield et al.

OTHER PUBLICATIONS

Drewniak et al. (Journal of Biotechnology vol. 164, pp. 479-488 (2013) available on line Feb. 21, 2013.*
Gen E Accession GU990088 entered Mar. 5, 2010 by Drewniak et al.*
Lucia Cavalca, et al., Arsenic-Resistant Bacterial Associated With Roots of the Wild Cirsium Arvense (L.) Plant From an arsenic Polluted Soil, and Screening of Potential Plant Growth-Promoting Characteristics, Systematic and Applied Microbiology (2010) vol. 33, p. 164-164.
L. Drewniak, et al., Arsenic Release From Gold Mine Rocks Mediated by the Activity of Indigenous Bacterial, Hydrometallurgy (2010) vol. 104, p. 437-442.
Amir H. Malik, et al., Perspectives of Low Cost Arsenic Remediation of Drinking Water in Pakistan and Other Countries, Journal of Hazardous Materials (2009) vol. 168, p. 1-12.
E.D. Rhine, et al., The Arsenite Oxidase Genes (aroAB) in Novel Chemoautotrophic Arsenite Oxidizers, Biochemical and Biophysical Research Communications (2007) vol. 354, p. 662-667.

* cited by examiner

*Primary Examiner* — J. Hines
*Assistant Examiner* — Khatol Shahnan Shah
(74) *Attorney, Agent, or Firm* — Vedder Price P.C.; Thomas J. Kowalski; Deborah L. Lu

(57) ABSTRACT

The invention provides novel strains *Agrobacterium tumefaciens* KKP 2039p and *Paracoccus alcaliphilus* KKP 2040p, the plasmid pSinA and its functional derivative, method for producing bacterial strains capable of chemolithotrophic arsenite oxidation and novel bacterial strains produced by this method. The invention also relates to the composition, comprising the novel bacterial strain or the plasmid pSinA and the use of these novel strains, as well as the method of bioaugmentation of an arsenic contaminated environment, particularly the method for the removal of arsenic from waters.

15 Claims, 7 Drawing Sheets

FIG. 2A-B
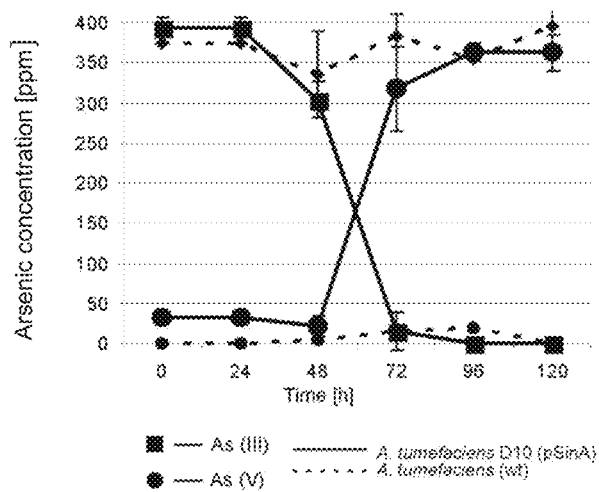
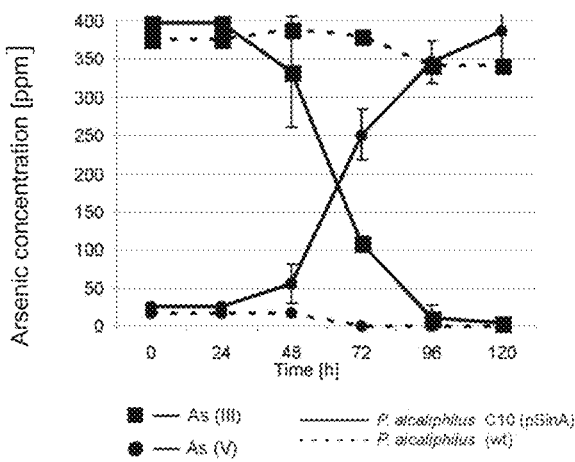

FIG. 5A-B

SEQUENCE LISTING

<160> NUMBER OF SEQ ID NOS: 17

<210> SEQ ID NO 1
<211> LENGTH: 108938
<212> TYPE: DNA
<213> ORGANISM: Sinorhizobium sp.

<400> SEQUENCE: 1

```
aagtcggaga gacggcctgt cggcgtcttg aatatttgcg aacagattgt aagggaagga    60
gattttggac gggaatttat accaggctaa atctctggaa acgttgaaaa aaaaggcggc   120
acagtttgtt gcatcaaaat gcgttaaggt tttgttaacc ctatttctct tgcggacaga   180
cgggaatcgt gcgctatctt cagacggtaa tagcgcgtct gacgctgata aaccgtcttg   240
aacctgaggc taaagtgaac gtgatcgaca ggcacatcag tagggcagca acgtccgcac   300
atattacgca gcgcgcggaa gctctatccg cgagactccg tgcggtcggt gaacgcgcct   360
ttcccccgac cgcgcagaag tcgcttcggt cgttcacctc tggggaggta gccgagatcg   420
ttggtgtttc ggatggctac ctgcgtcaac tctccctgga tggcctcggc ccggcacctg   480
atatcgggac cggtggccga cgctcctata cacttgaaca aatcaatggc ttgcggcagt   540
acctcgccga ggcacgcccc aaggaagcag tgcgtttctg gccccgtcgc cgggagggtg   600
aaaaacttca aatcatcact gtcgccaatt ttaagggtgg ctcggccaag accacgacat   660
ctctatatct cgcgcagggt ctggcgctcc agggttatcg agtccttgcc atagatcttg   720
atccccaggc ctcgctctcc gcgatgtttg gttatcagcc ggaattcgat gttgcggaga   780
ataccacgat atacggcgcc atcaggtatg atgaccagcg tgtggcgatg aaagatgtga   840
tccgcaagac ctacttcacg ggcattagca tcgttcccgg caatcttgag ctgatggagt   900
ttgagcatca gaccccgcga tttatgcttc agaaccgagg acggccagaa gatttgtttt   960
tcaggcgtgt cgcaagcgcc attgatcagg tcaaagacga gtacgacatt gtcgttgttg  1020
actgccctcc tcagcttggc ttcctcacca tgggtgctct gaatgcagcg acaggaatga  1080
ttgtcaccgt ccacccacaa atggtggacg tagcttccat gagccaattt ctcctaatga  1140
cgtccgatct tgtctccgta atcgaagagg cgggaggtaa gctcgactat gattttctga  1200
ggttccttgt gacccgccat gatccccgag atgtacctga acaggaaatc gtcggtttac  1260
ttcgggacgt attcggtacc gatgtgatgg ctgcggcagc atggaaatcg accgcgattg  1320
ctaatgccgg tttgaccaag caatctcttt acgagttgtc gcgtggcgcg gtcggtcgat  1380
cgacctatga tcgagcgatg gaatccatca gtgccgtgaa tcacgaagct gtcggcctaa  1440
tcaatgaagt gtggggtaga tgatggtgct ccactctcaa aagaatcaat cgcttaactt  1500
gttgtcagct gacgacgtga tgtcgtcggg gctagtagtt aaacgttctg attggggaaa  1560
```

```
tgatagatga gcaaacggac tcaatcagtt cgcaatctct ttgccgcagg gcctgatgag    1620
gcgccgaccg tggacacacg tcaaccaatg cagcgcgtag cttcaggagc ggttcggtcg    1680
ttgaaggaca cttttctcgga agttgagagg gactacgaag aactcaagca aaaagttgct   1740
gacggcgctc ttccgattga cctcgatccg tctcttatcg acccatcccc cttcgccgat    1800
cgttttgcgg atcaggatgc ttcggctgtc gaagctctca agcctctttt ccttgagcac    1860
gggcaagaaa taccaattct agtacgggct catccgactg agattggccg ttatcagatt    1920
tcttatggcc atcgtcgcgt acgagctgcc actgagcttg gtcttaaggt caaggcttac    1980
gtgcgcgaac ttagtgacga tcgccttgct gtcgcccaag gcattgaaaa ttcagctcgt    2040
gaagatctta cttttataga gcgttcaatg ttcgcgctga aactcgagga aggcgggttt    2100
gagaggactc tcattcaaac cgcgttgtcg gttgatcggc aggaagcatc caagctcatc    2160
agcgtaggcc gcgcagttcc tggttggctg gccgaagcga taggccgggc tccgaagata    2220
ggtcgcccgc ggtggcagga gcttgctgac ggtctgaaaa atgcaggagc ggaaagcaaa    2280
gcgcgcaagg ctacaactga caagtctttt ggtcacaaga cttccgatga tcgctttatc    2340
gcggttcttc gcgcgataaa ggcgatagat agaccgagcg cggaaaagac gccggtactt    2400
tccgcaaagt ctgccgaggg tactaagatc gctaccctcg cggtctccgg cagggtttgt    2460
aaaattgaga ttgatagaga tcgggacgag gcgtttgcca agttcgtgat ggatcgaatt    2520
cctgatcttt acgagaaatt ccggcagacc gagcccggat ccgaaggtta gagaaggaag    2580
aaaccgcaaa agaaaaaggc ccccaaacgt tgccgtcgtg gaagcctctc tcattggtct    2640
aagcagcctg agaatcgcat ttccatgaat cccagtcaat agtctttggc accgatttgg    2700
tgagctgatt ccttttgccg atcgaaaggt gaaagaaaaa tgcgaagtgg aagtgtaacg    2760
acgccattcg ggcggcggcc gatgacgctt gcgttggtca ggacccaatt ccaggcagcg    2820
gacatccgta agggaaaagt tgcggacaaa tggaaagtat accgcgatgc ctgcgaagca    2880
cgcgcgctac ttggcctgcg cgatagagcg cttgctgtgc tcaacgctct cctgtcgttt    2940
tatccagaga cggacctcag cgaagatgcg aaccttgtgg tctttccgtc taatgctcaa    3000
ctgagcgcac gagcgaacgg catcgcgggc acgactctga gagagaactt ggctgtattg    3060
gtgggtgccg gactgataaa tcgtaacgac agtcccaatg gtaaacgcta cgtgagacgt    3120
ggcaaggacg gcgaggtgga gacagcatat gggttcagtc ttgccccatt gcttgcgagg    3180
gcggaagaac ttgctctcat ggcgcagcgg gtggccgagg aggcacgacg cttcaaggta    3240
gttaaggagc ggacgactat tgcgcgcagg gacgtgcgta agcttatcac ggctgctgtt    3300
gaagatggtg cgcctggcga ctgggcgacg atggagacaa tctacatagg ggccgtagca    3360
aggcttcgga ccgccaagtc gattgaggcc cttgaatcga tcctggacga actagaacta    3420
ttgcgcgaag gtgtactcag cgtattggaa agcaacatct tttcacaaaa aaccgctacc    3480
aatgacaacg aaatccgtca gcacatacag aattcaaata ccgaatctat aaatgaattt    3540
gaacctagct cagaaaaaga gcagggtggg aaaccgatgt tgaagtcaga ccgactggcc    3600
gagccgctaa agagtttccc tattggttg tgatgcgag catgccctga aattgcggcc     3660
tatgcgcctg gaggccaggt ccagagttgg agggacttga tgtccgcggc agtcgtggtt    3720
cggtcgacct tgggagtaag cgcttcagct tatcaggatg cttgcgaggc aatgggcgca    3780
gagaatgcgg ccgtcgcgat ggcggcgata cttgagcgag ctgggcacat caattccgct    3840
ggtggctatc tccgcgatct tacctccaga acgcgccgcg tgaattttc gctcggcccg     3900 atgataatgg cgcttttgaa agtgaactct ggcggggcta aagtgcgtg atgttcccga     3960
```

```
taccaggagc tttcggaagc cgtcgattgt agtcagctga ctacaaacta accccctgtt    4020
gcagctaagg tttcttaatc acctgcgacg tccatattca ggagtcaaaa cagacgtttg    4080
caactgaaat agacgaacgt atttcgaaag tggtaccagc ggtccttttt tccgccgcgc    4140
ggtagggtag atagaagctt cagattgctt tgggaaacag agcggcgaaa tgcgcgttga    4200
gcatgacctt cgtttatcag ctcgttttt ccaacgccac ggaaatacgg tttcagtgaa    4260
catgctgcca ttgccgtccg gaggacgacg gttcccttat aacaatcgcg tagcccggcc    4320
gctccgacgg gtcgcgttgt tgtagtagct tgacgcctgc tgcaccgatc ggtggcgcga    4380
ctgctccatc gcctccggca aaggaacgcc ccggtttgcg gcttcggtca aatagcccga    4440
ccgcaacccg tgcgcggaaa actccccgc ctccagcccg gccatcgtcg cccgctgttt    4500
gacaatatcg ttgatcgcct tcggatcgag cgcccgacgg gaaacattcc cccagcgatc    4560
aatcgcccga acacactgc cactttcaat cttggcggca acaagccagg cgctcagggc    4620
atcaaccggc cggccggtca gaaagacaac ttcatcgctg tcgccgctgc tggtctttgt    4680
gcggccgaga tggattgaca gcgagggcag gggagccccg ccctcaacgg cgatcggcgg    4740
ctcagtcgtc aactgttccc tgcgcagccc ggcaatctcg ctgcgacggc gcccacccga    4800
cgcaaagcca accatcagga tggcgcgatc gcggatgtca cgaaggctct cgctggcaca    4860
agtggctagc atttttgcca tgatgtctcc agtgaccgcc ttggcgctct gcggcggcg    4920 ttggcgtggc acggcacgaa cggcgagccg gattgcggac ttaagggcag gggaggcaaa    4980
agcgccgtcg aaaccgcgcc acttggtcag tgtcgaccag ttggccagac gccggcgcac    5040
ggtatcgggc gcgtgcggcc cggttgatct gagaaagccg ccatctcgaa gggcctggtc    5100
aacctcagcc ggcatgccat ggtccggatc ggtttcgcgc ctcgctgggt cccagaggtg    5160
atgggcgaca aacttaagga gcagcgcctc gggcgccggc cagggaaggg cgccgccagt    5220
cgcggcgtgc gaccaggctt cgagatagcc gagatcggag gtcaacgccc gcagcgtatt    5280
ctcacccata ccttcgttga tcaggtgacg cagggtctcg acgtcctggt cggtcaggat    5340
ttcggcaagc ttgtcacgtc ggtcgatcgg cagcaccgac gcgatggtgt cgagctgttc    5400
ggcgcggttt aaaacattct gggtgacaga cgataccgac aaggtctttt tcgtcatagg    5460
acctgtccaa tgctaaatgt gcgttttgcaa aagttacgga aagcccgtat attccggaac    5520
aaaggagttc tgccatgacc tcgaccgtga cagcagcagc cgtttccaag aattttggcg    5580
cctatcagga tgccgcagtc cgcgagccgg tgattatcac caagaacggc cggccgcgca    5640
cggttctgat cgcctatgag gactatctgc gtctggccag acgcgaccgt cgcgtagatc    5700
tcaccacggc gatgagtgac gatgaacttg ccgccattga agcgtctcag atggagtcgg    5760
gtctcgatca tctcaacgcc gaactgctga cgggcaaaca tgctgccgac tgaaccaaaa    5820
gtcggttggg tctttcgtta ttcctatctc tggcactggc agcatctcga aggccgggag    5880
gagggcgaca aggaccgccc ggcgctggtg ttggcgattg ttgcgacctt ggacgatggc    5940
acgcccgcag tccgtgtcct gccgatcacg cactcgccgc cctctgatcc gagtgacgcg    6000
atcgaaatcc cgccggcgac aaaacggcgt cttggactgg acgacgaacg atcctggatt    6060
atcctgacgt aaagcaaccg gttgtctgg ccggaccgga atgtccggcc cgttgacagc    6120
gaaaccggct accttggccc tttgccaccg gcattgttca acgagatcaa gcgccgcttt    6180
gtcgaactgg cgcgcggcca gcgtcatcgc gccacgggcc gcagcgaata gcggcttagc    6240
tgtggtcgcg gatcttggct ggccgcgtct ttgatctgca atatcgagca aaatgggtcc    6300
```

```
tttgtgacca tcctagcgcc caattttacc gatttgcggt ctcaaatcaa tcacttccga    6360
taagggttac ttatcggggg tcagaagccg caggcccatt tgtcagaagt atagaactct    6420
aacaggtata tagatttccc ttaacgaatc atttaccata atttcaatgg tttacgatct    6480
cgcgaaattg cccctccaga gcctgttgag gccggtctca gaaacaggcg tcgcacttgc    6540
tcgtcttgac gagcgcatcg cccgttctcc cgttggcggg ggctttctcg agcgttccca    6600
tttcctcgag gcccatgcct cgctctgggt cgacggtgaa cttgtccatt tggaggacct    6660
cgttctgcac gacgcccttc gcgacatccg cgcacccacc cacgaactca ccatcgcccg    6720
cgacatcctg aaaacccgcc gtcgcatcgc cgcccatccc ccggcctggg cgctctctgc    6780
tcaaggcctc gcctccctct gcgggcaggc gtggcctgca gcatcgtcgg gtgtcgacgg    6840
agagagtttg ccggatggca atgttgtcag cgacactcgg ggtggggtag ggaggccga    6900
agatcctgat gccgacggtc ttagtgatgc gtttgccgcg atcgatgcgg ttcttgcccg    6960
ctcggacgcc gcgattgaag aagcgaagaa gccgggggc gcgaaaaacg cttcggacaa    7020
ggatccgttc gtctacgacc tcgactggga tgaggacgag cggctggcgg agtggcaggc    7080
cgtgctgacg cggtcccagg atctgccgcc ggtcctgcaa tccatcgtgg cgctcgacgc    7140
ctggaatgaa atcgccgtgc tccagcatgc gccgtggctc ggtcggctgc tggctgcctc    7200
gatcctgcgc gagagcggcg tcaccaccgg tggccatctc gcagcgatca atgtcgggct    7260
caaggctatt cccgtcgatc ggcgccgca tcgtgatcgc gagacgcggt tgctggcgat    7320
ttcaagggcg ttggtgattg ccgccgagac ggggctgaag gagcatgatc gcctggtgct    7380
ggcgcggcag atgatgatgc gcaaacttga gggacgccgg acgtcatcga ggctgccgga    7440
gcttgtcgag ctcgttatgg cgcggccgct gatctcggcc ggcatggtgg caaagacgct    7500
tgaggtcaca ccgcagggag cgcgccggat cgttcaggag cttggtttga gggagatgac    7560
cgggagaggg aggtttcggg cgtggggat tgtctagaat gggtcagaac gagatgaaat    7620
cgaacgacag gccttgcgct atctataatt cggtcctatc tttcggggtg aattaggagg    7680
cgttcggatg gaacatctga caacggcaca gcggctttt gtggtgggcg cgccgctgga    7740
catcttcaag aaggttgtcg agcgcgcgcc gattaagccg caactcgtga gcgaggtgg    7800
tcgaagcatt cggcagttcg gtcaagctga gctggtgttt ctccatgcct atgacgaact    7860
caaactggcg ctgacgccca agagccaatc cgagttctat gaggcgttgc ggacgacatc    7920
cctgaagcgc agtctcgcga aggaagtcgt gttcggcaaa cagcgctacg acatcggtca    7980
gcacctagtc ttcgtcgagc gcaagctgaa ggaactcgag aagctcaccg atcaggtcga    8040
cctatccggg aaggagccgg tcatccgagg cacgcacatc gaggcgcatc ggatcgctgc    8100
tcttctcaac gccggcgcca cggtcgaaga gattcttcgc gactatccct ccttgaagga    8160
acaacaggtc gtggcggcgc gcgtctatgc ggaggcgcat ccgaaggcgg gccggccgta    8220
cccgaagcaa acggcaaaag ccgccatgcg cgcagccgat cttagcgcgc tggatgactg    8280
agcttgaaat acctgctcga tacaaatgtc ctgaaagaga ttggtcgacc cgaaccgcac    8340
gagaatgtcg cggcttggct cgatactatc gatgattacc gatctcgcca tcagcgtgat    8400
ctcggttcga gagatttcga aaggcatcga gaagaagcgt acgaccgatg acgtcgtggc    8460
gaacgcgatc gccaaggctg ccgacgcaat cttcgcggct tatcaaggtc gtattctccc    8520
cgtcgacgag cctgtcgcac gccgttgggg tcagatgctc ggtcaatcag ataagaatat    8580
cgacgatacc ggcttggccg cgacagcgca ggtgaatgat cttatcatgg tgtcacgcaa    8640
cgtcgcggat tttcagggcc ggggcgtcac ggtccttgat ccgttcaaga agcctgccag    8700
```

```
atctgtgccc tcccaagatg tggcacgatg agcttcgacc ggatcggata agatatctaa    8760
attatctcag ccatccacaa ttctgcggaa cggatcacca aacacgtgca gggctaggaa    8820
gcgtgcagga tcatatcccg ttgcttttcc tacgtcctga ttggctttga agaccgcgtc    8880
tattacctga tctccagcat cccaacgttc caggaaggcc ggaaaccacc tcggtgtaat    8940
cgacgaagcg aggggccacg gtgacgccac aaccgtggag catcctcggt ccaacaactg    9000
acgcgtaagc ccaattgtca tgtttgccgc agggtgcttg tcgctacggc cgccgctgca    9060
gacaaacaaa accacgactc ctacattgcg aagagcgtct gccaagtcag acgcaagaat    9120
tcgcaaattg ccttcatcgg aaacctggtg aaaaaacggt tctccatccg ctacgctgcc    9180
gtgggcggct atcaccacaa gctgcgagcc ggcgaggtcc tccgggagcg ccgcagcggt    9240
attgagggat atattgctcg cctcgaaagt tggctgtaac caacgcccta tgctgctcag    9300
cgtgccttct tgattcagat ccgcggaaat ccatgccttt ctggttccat tcgattgcag    9360
cggctgtgtg cgggcgcttt ccaaccaaga gagcgatggc gcggaagcga tggcacggct    9420
tcgccccgcg aagtcgttgt cgacccagag caaattgaag gccagctgct ggagcttgct    9480
gtcggtgaca agacaaccct tgtccggcag cggtgtcgat aggccaagcc tttccgtcga    9540
cgtgtaaaac aggttcgctg ttttctcatc gacgccgtat cgatacggga attctttgct    9600
ccactgtcgg taatctgaca cggaaaacgt gtttgagggt tcgacacctg gcgtggatgc    9660
ggccccattc tccgcatcga gccggatcaa ccggtctttc gcatcgatac cgatcatgac    9720
gaaaccagct cccgccgaat gtcttttccag catcgaaagt ggttcctctg gcccctttgag    9780 ggccgaaacc ggttcggatg tggcctgcca gccaggtttg gcaacgcccc tgtcggaaag    9840
gagttcaatt gcgagtgcaa cgccgagact cgacgaagcg tcggcttcgt ggccaagaag    9900 cttttttgacc accggcacca tcttgcccga atcaaagccg gaatcctccg aatgtcggga    9960
tagttctatg cgctcgtgaa ccgcaaaaat ctggtcggcc gtcggtcttg cggaggctgc   10020
cgcacgggtc aactgttcga tcggacccctt aagccgctcg acaagggtgt caaagagcgc   10080
ctcgtcgtca ggatcgacgt ctatcccggc ctcgcgcgcc caagccaaaa tttgaccgag   10140
tatcaatgtt acaggtgcat ggtcgccggc gtacgatgcg cgcgtcttc ctaggtctac   10200 ggcgtcctgc aggagggccg gcaacctcgc acgaaattcg ttcgcgtcgc gaaatccccc   10260
tttcagtttc agctggagcg caagcaaatc gagttgaatg tcgtttccgt cagaaagccc   10320
gagttcatcg agaaccatgc gggcatgttc ggccatgtgc tctgctgctt tgatgagccc   10380
aacgtcccgg aacgtcccgg caagaccgta catctcaatc caaagctggt gcagcgaaac   10440
cggtccggcg agcttggccg cacacgcaaa cgcgactaaa gcttcgatag cattacccga   10500
gcgccgatag acgtcaccga ataccccccca tgcaatacgt tggcgtacgg ggtccaagcc   10560
agagcagaga agagcgtgct cggcataatc tcgcgcctcc tggactttgc gcgccgcga   10620 aagctggatg gcgccgacac ccataagttc caggtcagct ggacctagtg attccgacat   10680
ggcgatgctg acaccgatgc ttaaccaggc tttgaattcc gccaaatcgt catcggtttc   10740
tgcgtcctcc gccagctgag gtagcatggc cttgaacgta gccaccaatc gatcgccact   10800
gcacgggaga tcttcgctcg gaaacctcgt tttgccgagt gtaatgggcg cttcccgttc   10860
gagccacgcg aacgcggcgc ggtgaaacgc ctcaaacgtc ttgaactctt cagggctgat   10920
tgcgtcgacg tcgtcagcct gctggaagtc tatctcgccg gcataagaag acagaatgat   10980
gctggcgatt agcgcaattc cgctttgccc agcgacttgc agatcgagaa tccgagctat   11040
```

```
taacaacctc aatctgcctt ccgcaggdtg tgtcgcggcg tagcggaggg gaatctcgac   11100
tgcctccgtc aatcgttctg gctcgacgag cgctccgatg ttcccccgtg attgcagtag   11160
tatttgttcc ataacgtcga cggtaagaaa cgccttccaa cgcggcggcg acggattttt   11220
atgcgccgta acgaggtcga acgcatggag gatcaatccc cgccgagtg cgtcttgcac    11280
caatgtctgc tcgatcgtct ccgctcgttg cggataggcg agcgtcagat gtcgcccaac   11340
ggtcggatag tcgggggag ttggcgagct caattcgccg gcaaatgcat catagagcgc    11400
ggtcagttcg ggttctgcct tacgcgatgc gaggatagcc gacgcatcgg caaacctccc   11460
cgccgatttg tgttcggcga atgtgcgatc ggcgaggact ggtgcatttg ggtggtgctg   11520
cctgagccgt gcttcaatcg tttgttccaa atccgccgca tctaaacggc ttgccgtgcg   11580
aagagcggtc tggaggttct ccatggttga aaggcttggt gcgcaaaggc gcagcaaccg   11640
caccgcaaga gcgcccgcgc cagcctcctc ggcgatcttc gccatcgcga gtacgaccgg   11700
aggattcgat ttctcatcaa gaggcaggtt ttccagttca tgcagagtct ggccggtgag   11760
gcctgcaaga tgtagcaact ggattctgag atttggcttc tcatcatcga agttggcggg   11820
gagcgtatcg acttcctgca gcgcaacgcc cagacggcct tcccgtacta agctgctcca   11880
ctgcaaagcc cgtacggaga gttcactctg gagatcgttt tcagctgttg ccaggtagac   11940
gtctacgtca tcgtggacat cgtgcaacat gtcttgaaga gctgtttgca cgggagcgaa   12000
gtgcccgaca tcgatcaaaa aatagctgct gagcctctcg cgcaagcacg acgcgaggtg   12060
agcgatttgc ggtacccaga agttctcctc cagagaggat gcagagccta tttcatcggg   12120
tgcaatcggt ctcacaagag gggagcggaa aagagccgca ttcagtatga tcatcgcgct   12180
gtacggttgc cgtgctgaca tgctctccac gagggctagg gtatcgtggt tttcaagttc   12240
gatgatctgg ctctcagcgg gatcgacgcg tccgggatat ctcgctattg ctgctttcat   12300
agccttgtcg agggtggcct tcccgccagc ctgatcgcac gacactgccg gagccagcac   12360
gagaaatccg gagaacgggt gttcacgatc ggacgtcagc caagacaaaa ttccatcgat   12420
gtacagatat aagcgagacg gaagatcgtc gttgcccagg cacattatat cgctaccggt   12480
gctcgacgtc cgactagcga atatcggtcg tagatcgtta gagaccggtc gcggcgcggc   12540
ctcgtttgta ttttctgacg acgctttgcc attggcatcc atgtggtaac tccggcgatc   12600
agcttccaag gttgggccaa ccagattggt tggacgaaaa agtgacccag ttccaacgct   12660
cgaataggg cgtcaggagc caattgcgcg attgtatttg cttgaatagg taatgaaagt    12720
cacatcaacc ttgaacgtca gaaaaatgtg tattattttc tgacgcatga aaaccatcac   12780
gtctgtcccg gatcagatca tgaagcgcgc ccgcgcgcgc gggcgcggcg tcgtcttcac   12840
gccaagtgat tttctggacg tggccgggcg cgcggcagtc gaccaagccc tctcccgatt   12900
ggtcaagatc gggaaactcc gtcgcctggc gcgaggcctt tacgacttcc cgaaggttca   12960
tccacagctt ggcccgctat cgccggcccc tgatgatgtc gcccacgcat ggcgcgcga   13020
gaccgggtcg cagctgcaga ttgcgggcgc gcggcggcg aatgccctcg gtctctccac    13080
gcaggtcccg agcaaaagca cctatctgac caacggtccc tcgcgccggg tcgtgttggg   13140
caagcgggtg gtcgatctgc gtcatgcctc gccgaagcat ctgattgctc caggcagtga   13200
tgtcggcacc gtcgtgcagg ctcttcgtca tgtcggggcg gtgcgtgcgg ccgatgttgc   13260
acaaatcgcg gcgcgccgtc tgtcggccaa tgacaagaaa aagcttgcct caactgcagt   13320
ccaggctccc gcttggatgc ggccgacgct cgtctcgatc gccaatgcag catccggtga   13380
gctcgatgga tgaggtcccc ctccttccgg cagatgacag ggcacccaat agcttgcgca   13440
```

```
gtttggtggg cgccgcgggt cagcaagcga ccctacggtc gcgcgggagt atacaaactg   13500
gcggtcccta tgggcgctag ttacccgacc aggatcatcc tcgctttccg gagcggtggc   13560
gtctgcgcct ttccgaaatg cgacaagcac ctcacctacg acgcgaaggt cggcgatgac   13620
acctatgtcg gcgaggcggc ccacattcgc ggcgagaagg cgaccgccgc acgctacgat   13680
gcctcgatga ccgatgagga gcgcgacaac gtgcgaaacc tcatctatct ctgcacggat   13740
catcatacga tcatcgacaa ggtcgaggcc gattggccga ctccgacgct tctggctctg   13800
aaggaaagtc acgagaagca ggttcgtcag gcgatggagg aagccttcgc tgacgtcgcc   13860
tttccggaac tgcaaaacgc cgtgtcctgg gtctccaagc aggcgcccgc catcaacggg   13920
tcgttcgacc tgatcgcgcc ggacgagaag atcaagaaga acgcgctctc gaacggggcg   13980
cggcacatta tcgccgccgg cctgaccgca cgcgtgaccg tcggtgagta tatcgaggcc   14040
gaagcacagc ttgattccga tttcccagag cgactgaagg ccggcttcct cgaagaatat   14100
tatgcgcggc gaaaggaagg ccataagggc gacgaactat tcgagctgat gtgcgccttc   14160
gcccagcgcg gtctgaaacg tcaggcggac aagaccgcag ggatcgcggt gctggtctac   14220
ttgttcgaaa tctgcgatgt gttcgagaaa tgatccttcc aaccaaacac atcccgcaga   14280
aagaggcgct gatcggagtc ggcgcaaccc ttctggcgca cctaggcggg ccaatgacgg   14340
tctccggcct gtgggagcgt ctccgctcag agcctaacgt cggtacgttc gagcgcttcg   14400
tcctagcctc caacctgctc tatctcatcg gcgccatcga catcaaagac ggtctgatcg   14460
tcaggaccgc atcatgatcc gagccgtacg cgccaaccag aagggctttc acgctgccgc   14520
gtttaaggct ggcatcaatc ttgttcttgc cgaccgctcc tcggcagccg gggacaagga   14580
cacgacgaac gcccttggga agtcgacgct gatcgaaatc atcgacttct gtctggcgag   14640
caaccccctcg cccggaaagg gcctgcgcat cgaagccttg cagggctggg ccttcaccct   14700
ggagctgacc atcggtggca atgacgtcgc cgtaacgcgg tctcccgacg cgcccgggtt   14760
cttcgccgtc gaaggatcga ccgtgggtg gcctgtgcag ccggccccaa acaaggacgg   14820
catgccaggg ctcgacacga aaaagtggcg agcagtgctc gcctgggcgt tgttcgggat   14880
tagcgaccte gcatctgagt ccggatacaa gccgtctgcc cggtcgttgc tatcctattt   14940
cgcgcgaaac caggctgttg cctacaaacac cccgttcaaa catttcgaca atcagaagac   15000
ctgggacatt caggtccaca atgccttcct gcttgggctc aactgggaga aggcggccgc   15060
ctggcagcag ctgaaggatc agaagaacgc gcttgatgcg ctgaagcagg cgatcaagac   15120
aggcgcggtc gatggtgagc ttgcttccct cggtgagctt gaggccgaac gcctgcgtct   15180
caccacgcag cttgagcggg aacgcgaagc cctgtccacc tttcgcgttt tgccgcagta   15240
tcgcgagatc gaggcacagg cgaacattct cacaagcgag atccacggct tggtaaacgc   15300
taatatcgtg gataagcgcc gacttgagcg ttatcgcgag tcagtggtga acgaggatgc   15360
accgacggcg gatcgtctcg aagctctgta taacgaagcc ggaatcgcgt taccgggcgc   15420
cgttaggaaa actctcgctg atgctcgcgc attcaacgag aagatcgtcg ccaaccgccg   15480
cgagttcatt gccagcgaga ttaccgcgct cgaagctgcg gtggtaaatc gcgatgctca   15540
ggttgtcact ctgaccgatc gacgcgccgg ttatctcggc gccctggccg gacaaggcgc   15600
cctggaggaa ctcacccacc tgcaggaact ccacgctgcg acgcgtctca aggtggatga   15660
gctgaccaac aggattaccc agctccgcca gatgaccacc aagtcggaca cgatcaaggt   15720
tgaaaccgtt gcgctcaaac gggctgcaat actggattat gaagaacggc gcgcggtgtg   15780
```

```
gtcccaggca ctgagcctgt tctcggaatt ctccgaggcc ctgtacaatg ctgccgggag   15840
actggtgatc gatatcgacg acaccggata caaattcgac gtcgagatag ctggcagtcc   15900
cagcgagggt atcagcaaga tgaagatctt ctgctacgac ctcatgctca tctcgttcgc   15960
gcgccagcgt ggcctgggca tcgacttcct tattcacgac agcaccatct cgacggtgt   16020 cgacccgcga cagcgcgccc acgcgctcga actggcggcg caatgtctg ccaaatatgg   16080 cttccaatac atttgcacgc tgaacaccga catggttccg atcaacgatt tttcggcaga   16140
cttcgatttc gcatccgtgg tccgcatgcg cctaaccgac accgacccaa gcggtagtct   16200
gcttgggttt aggtactgat cggaggcgga gtggatggcg ctattctcgc aagaccaact   16260
ggaggccatc gctggcgcgc tcggcgatac ggaggcgggt ttgaccggcc ccgagatcca   16320
gcacctgatc gcatcgacca aaatgtccga tccgggggca atgacgaaga gggtccgaat   16380
ctacaacgcg tttgctgaaa gtcagaatac caaacgcaac cgaaccaaca ttttgcaatt   16440
cattcgtctg gcgatgaagc cagcgcgcta cagccgctct cccgagcgtt atgagccgat   16500
gcgcgcactg cttaaccagg cgctcgcatt cgccggcctg gttgtcgatc agactgggga   16560
actcaaaaaa gccgagattg cacaaaccct ccccgaagcc cagcgacggg cgcgcgagct   16620
gcgggccgat ctgaaggcc gcggcgtcca ccccgatgta ctcaggtttt gccgagccga   16680
acttctggca gacaactatt ttcacgccgt ccaggaagca gtgaagagcg tcgccgacaa   16740
gatgcgcacg cgcaccgggc tttccgacga cggcgccggg ctggtcgatc gcactcttgg   16800
tggcgagcct ccgctcctcg cgatcaatcc gcgcagcacg gtaagcgaac ggagcgagca   16860
gagcggcttt gcaaatctcg tgcgcgggac attcggatg ttccgcaatc ctacagcgca   16920
cgatgctcga attcattggg tgatgtcgaa agaggacgca gaagatctgc tgacaatcgt   16980
ctcgctcatt catcgtcgcc tcgacagcgc gcatatgccc ccacgagttt aagtgagacc   17040
caatgtgaac acgacaattt ggcgaaggag attgtaagat tgggtctaac gatgccgacc   17100
acctggcgct acggttctcc gggagcgatg ccgcccttcg ctgcgaacgc ctttaactcg   17160
ctgatccaca cgatcgccgg ccaatcggaa tcgtcatggt cgatcttcga gctcttcaag   17220
gcgaagttca gcggcggctc gtcttggagt tcgagcgaaa gctgggcgat cagcgatttg   17280
cataccgcaa tgatgagggc cgctgacaac gccccgtat tcatcagcgc gttctgggac   17340
ggttgcaccc aagtgcaggc gtcccatccg gaagtcggct gccggatgc cgatgtcgtc   17400 aatcaaatcc tctacgaaca cgaggtccct tacgaggtta ggccgccgc actgctggcg   17460 cgccacccc agacgccaat cgtcgtacaa gcaccggaga agtctcttgg tgagcgcgcc   17520
ttcgccctga tccacgcctc gctggaccag gccgatcgtc tgttgctcga gcagcgtcct   17580
cgccaggccg ttcaggagat tctgtggctg ctcgaaaccg tttcgacggc tttcagggc   17640 catgaaagcg gagctggcac gatcgaaggg aaatatttca atgagatcat tcgaaccatg   17700
cgcaataata atcgcggcag tgcccttgct gaagccctcg gatggatgac gaagatgcac   17760
ggatacctat cctccccagg gggcggcggc gttcgccacg gcacccagct tgcggccgat   17820
gtctccccta cgctcaggga ggcacacctc tactgcaacc tgacccggag ctatatcaac   17880
tacctcctgg ccgaactggc ggaacagaac taatcgcagg agtcagcgat tcgtgttgtt   17940
tttcgtacac aagagagtgg acggcgaacc acactatatt gcgccgcgct agtttccgga   18000
aatattccta agatggaatg caaggcgctg cgctatcgtg cggttgcatc gcgggcgaca   18060
gagcggacaa cagaaggaag tataccaggt gggcgtatga tcagtcgcgg ttcggaatgc   18120
catcgttggg agccccatat tcatgcgcct ggcaccgtcc tcaacaatca gttcggtgcg   18180
```

```
gccgatccct ggggtgcata tctcacatcg ctcgaagggc tgacgccgaa gatcgaagta   18240
atcgccgtca cggactatta cgtcaccgat acctacgaac agttccttac ccataaggcc   18300
gctggccggt tgccagacgt gaagctgctc tttccgaaca tcgaactgcg cctcgatgtg   18360
gcggcaaaga cggggttcgt gaacatccat ctgttggtga gccccgagga cccagatcat   18420
gttggcgagg tcaagcggat cctcaagcgc ctgcaattcg cgcccataa cgatcgcttc   18480 gactgcacgc gcgaggagct gatcaagctc ggcaagcgct ccgacaccac gatcaccgaa   18540
gacggcgcgg cgctccgcca cggcgcgacc caggtgaagg taaacttcga ccaattgcgc   18600
aaagtcatcc atgagagcga atgggcgaaa aagaacgtcc tgatcgctgt cgcgggcggc   18660
gctggagacg gcacgtctgg gctgcggcag gctgccgacg cgacgatgcg tcaggaaatc   18720
gaaaagttcg ctcacatcat cttttcgagc agcccggcgc agcgcgagtt ctggctcggc   18780
cagcgcggtg tgccgatcga ggagctgcgt tcgcgctatg acggctgcaa gccttgcctc   18840
catggcagca attcccacga ccagaaatcg gtgggccagc ctgtcgacag tcgcttttcg   18900
tggatcaagg gcgctttaga gttcgatgcc cttcggcagg cctgcatcga ccccgagggt   18960
cgtgcctatg tcggcgagca gccgccgcgc tcggcgatgc catcgcaagt gatctcgcat   19020
gtcaggatcg acgatgcgga ttgggcgtcc acaccggata tcccgctcaa ccctggcctc   19080
gtcgccatca ttggtgctcg ggggtccggc aagaccgcct tggcagacgt catcgcggcg   19140
gggtgcgatg caattccccc atccggatgg gacgcggacg agaacaacag tccgtccttc   19200
ctggcgcgtg cgcgcaggct tatcagcgat gcgacgacga cgctgacctg gggcggcggc   19260
gcaacggtca cccgcgcgct cgacgggagc gatgccaacg gccatatgtc ctttccacgg   19320
gcccgctacc tgtcgcagca gtttgtcgag gagctttgct ccgccaaagg cgtctccgac   19380
ggtctggtcg aggagatcga gcgcgtgata tacgaatcgc attcgcccga tgatcgcgaa   19440
tgggcgctcg acttcgccga gctgcgcgag cagcagacct cccgtttcca acaagcgcgc   19500
gagcgcgagg cccaggcgat cgccgacatc tccgaccgta ttgccaccga gttcgagaag   19560
gagagcctcg tcgcctcgct gaccaagcag gtcggggaga agaacaagct gatcgccgac   19620
tacgctgccg atcgcgcgag gctggtcgta agaggcaccg aagctcaggt cgcccggcat   19680
acgcaactca gcgaagccgc tcaaaagctc cgcagcagca tccagaattt tggcaaccaa   19740
cgccgcacct tcgtcgcact ccacgacgag gtccgctcca tgcgggcaac cggctcgccg   19800
gagatgctgc ggcaggcgca ggcccgtcac gccaatagcg ggctcaacgc cacgcaatgg   19860
gacgaattcc tgctgatcta caagggcgac gtcgacaaga gccttacagc ctatgtgaac   19920
tgggcggata ccgagatccg taagcttcag ggcgttcccc cgccgccgg cgatcccaat   19980 gtcgcgctca tcgccgacac ggttgatatc tcaacactgc cctggcgcc aatcatcgcc   20040 gaaatgacgc ggctagaagc actgttcagc gcagataagg tggtgcgaga tcaatatacg   20100
gcactcacca accgcatcgc gcaggaaaat tccgcgctcc aaacgctgca gacgcgcctt   20160
aaagatgcgg aaagggccgc ggcgcgccgc aaggacctgc agaacgaacg tgacgacacc   20220
tacggccgcg tattcgaagc tatcatcaac gagcagaata cgctggccgg gctttacgca   20280
cccctgatgg cgcgcctcgc ggccgcctcg ggcacgttga agaagctcag cttctcggtc   20340
cgccggatcg ccgacgtcca ggcctggggc accttgccg aggaggagct tctcgaccga   20400
cgcaaaaccg gtcccttcta cgggcgcggt tcgctgatcg ctgcggccac ggacgcgctc   20460
aactcggcgt gggagacggg atccgcggct gaggtacagt ccgccatgac ggccttcatg   20520
```

```
gcgaaatatc tgcgagatct gctgacccat gcaccttatg cgccgaccca gcaggcggaa    20580
ttccgggctt ggtcgaagca gttcgcgcac tggcttttca gcaccgagca catcactgtc    20640
cggtatgaaa tctcctatga cggcgtcgac atccgcaagc tctcacccgg cacgcgggt    20700 atcgtgcttc tgttgctcta tctggcgctc gacgattccg acgatcggcc actgatcatt    20760
gaccagcctg aagagaatct cgatccgaag tccgtcttcg acgagcttgt cgcgctcttc    20820
atcgccgcga agcaaagcg ccaggtgatc atggtcacgc acaacgccaa cctcgtcatc    20880
aacacggacg cggaccagat catcgtcgcc gaagcagggc cgcatcccgc aggcggcctg    20940
ccgccgatca gttatgtggc gggcgggctg gagaacgcgg caatccgcaa ggcggtctgc    21000
gacatcctcg aaggtggcga agccgctttc cgcgagcgcg cgcggcgcct tcgcgtccgc    21060
ctcgacagat aggatagcga gatggttaca cgcgatatcg ccgcctccga tcctcaacag    21120
atcttcggct tcctggcgga gcgcggctgg tctcgccaca gcagcgaaga cgcggaccca    21180
gacgccatcg tccgcgcgct gggccaactc ggtgatcggc tcgggacgcg cgttccgggt    21240
cgtgcgggct cgctcgagga gtcgtcgag ccgcgtgccg ccgatgatgc gcatcctcga    21300
tccttgagcg cgcgctacgg cctgggcgcc ctgccgcttc acacggaact cagccatcgc    21360
actagaccct gccgttacct ccttctcgga tgtatcgatc cgggatcgcc ggccgcttcg    21420
acgatgcttc tcgactggcg gacgctcggc ttttcgcagg aggagcttga ccttctcgaa    21480
gacgctccga tccttgttcg caccggtcgg cgctccttct actcgacgat cctgtcgccg    21540
ggccgagctt tcttgcggta cgatcccggc tgccttgaag ccttggacga gcgcggccgg    21600
acggccctgg cgcttatcga ggaccggatc gccggcgccc actcagaggc gcatcattgg    21660
cgccggggcg acatcctcat cattgacaac tggcgcgtcc tgcacgggcg cagtccgtcg    21720
gaccgagggt ccgccgccg tctagcaagg attctcatcg atgcctgagg aagtcttcat    21780
cgcaatcaac ggcgacgctc tccatacaaa gtcgaaagtt tacatcggcc gagcccttgt    21840
tcggaagggc gccagcgatc tagacgaata tcagctctgg gcctcgctcg cgctcgagct    21900
gctcggcaaa gccgcgctcg cccggaaaca cccgagcctt gtggtcgatc cgacgcactg    21960
gcagtcgatg ttcgtcgccg ccggtatcaa tgtcacgacc gacgtcaaga cgatcaccgc    22020
caagaccctg ttcgagcgcc tcgcacacct cgtcccgcgc ttcgacaaga cggtgcagaa    22080
attctgccaa gacatcgccg agcgtcgaaa tgccgaactg cactcggccg accttccgtt    22140
ccgcaccatg cgtctcgacg cctgggaggc gcgctattgg catgcgtgcg atacgatcct    22200
gcaccagatg ggatcgtctc tggagcaatg gcttggggcg gccgatgcca aggcgccccg    22260
tcaattgctc gacgaagccg ccaaggccct cgaagcggcg gtcaaacttc gcgtcgaagc    22320
tgcaagggaa cagttcgagg cattgaggag ggccgagcgg gaacgtctgg ccgccgaagc    22380
cgaattgcgc gagccgcagc atcaggcggg aatcttcaag ggccgctacg acgagatctg    22440
gaccgagagc tgcccggcct gcaaatgcag agcgttcatg accggcgagc agaccggtga    22500
agatatcagc gaagagcgcg acgagtatgc gatctgggaa atcgtcgacc gcgagttcgt    22560
cggcgaagag tttcgctgcc gacatgcga actcgcgctg atgggaagcg acgaaatcgg    22620
cgcgggcgga ctgaactaca tccacgagga ccaacaagag cgcgaaatgg aatacgaggc    22680
cgactacggc aacgactgac catcggcgga gaaatataca cgggcaac acacatgccg    22740 gtctacttca taggcgagga tgaaaacgga tgctcgccga tcaaggtcgg cgtagccaag    22800
gacatcggcc ggcggaagag cgacctgcag accggaaatc cgctcgaact caaactcctc    22860
ggttggatca cgtcgcccga cgatttcgag accgagcgcg atctgcaccg tcgcctcgca    22920
```

```
tcccggcgcg gccgcggcga gtggttctac atcgagccgg ccgacgtcct gcctttcctg   22980
atggaggtcg gacagcgtgg tttcgtcgcg aagaatgcgg atgccttcga aatcaccggc   23040
tacgatcgcg acgccatccc cgaatatctc ggtgtgtggg aatgggccga cctcgaaatc   23100
gacgaatgct gtcccttctg cggatgcctt tgcggcatgc attttcagga cgcctctcag   23160
atgtactact gcatccagtg cgacacgctc accgacttct cggaactgtc cccggatgac   23220
cgcgacgggc gagaggactg actggcctca agaccaacaa cgaatggggg cataacatga   23280
gcatgcaatg gctattggcg cgagcaccgg gattccacgc gctgcccgaa gaggaccgcg   23340
cagcgatctt caacttcact ttcctgtgga gcctgttcga ggcccaagtc atgggcaatt   23400
ttgcgcgcgc cgatctcatt tgcgcgaagg ccgacgagtg gcaagacgcc ggcacgctcg   23460
acgccgacca gtatgatgga gagctggctt attttcgcca gcgctatttc gccaacgggc   23520
aattcacgca ccacttcgcc cacctgcatc ttcgccccgc cgatcagccc gacctcgtcc   23580
ggtcggtcct cgacgggagc aacaacgacc cgcgcgatcg gctgctgacc gtgctgataa   23640
tcgtctggcg ctttcgcaac aatctgttcc acggcgagaa gtggacctac cagctccagg   23700
gccagcacgc gaatttcacg cacgccaatg ccgtgttgat gcggctcctc gaacggcatg   23760
ggcagttggc agcctgacgg cgtcaggtgc tccccggctt ccgccagaat ggttcgtccg   23820
catagatgct gacgcccatc tgtccgcgcg gattttcggc cgcccaagcc agcacctctt   23880
cggtcgggac gaccagtctg gtctggccgg tcggctccca gcagttcttg ccggacttca   23940
tgtagaagtc tccgacacct tccacgttga tccggccggt gcgcatgcgc cgcaagccga   24000
aggccgtgat ctggtacgtc aggacgcctc cgtgggtccg gcgaacaacg ccgccgatc   24060
cctcgggttg attgcggtag tagtcttcga tctcggcctc ggtctgacgg gcgcatggcg   24120
aaagcttacg gtctggcacg gcaatcctct cgttcggggg ctgtcggccc tccgctgcac   24180
acaggcggtg actaatccct ggtggcgaac accttgcgcg ttccctgcat cagcagattt   24240
cgtcgatctc gaggcgacga tctagctttg atccagacca attggccctc gtggcaacgc   24300
cggcaccatc gttcgtgcag gtagagagcc acgctttggt tgcgctgaaa tcagttagta   24360
tctcagcaag ttaagcagcg gcttcacaca tagtccccag aaattccgca tgccccgaag   24420
gatctgcttc aaatatttgc cattcaagat gcgtactctg gtctgctttc cagttccgct   24480
ccccacagcc gcccgtccat tcacggcgcc atacagccgc tctccggaca caaaccgacc   24540
ttcaccgctg agcagtttga gcacgttagc ccctattcga ataacagggt cgaaggttct   24600
gatccttca aggcggcgaa tctcacgctt cgagtgcgc gatgagattt tttaagagat   24660
tacccgatgg aaaatggctc gaaacgcaag ggcatgcccc gctctagggt tacgagctcc   24720
ggtggcagga ttgccagacc ggcggcttgg gccatgggcg acaggcttcc cgacgatccg   24780
cggcccagca ttgccagcac gggagtgcca gaagcgtcgc gactctgaag tcgaacgggg   24840
acgaattccg ttcggccctc cttcttgcgc aacccaaagt cggagatcgc cggcatccag   24900
acgggatcca aatgctcgat cccggccaca gccctgatcg ccggcagcgc aatcttgtcg   24960
agtgtcacgg cggaggccat gggattccca ggcaagccga taaagagcgc cgaccctagc   25020
gtgccgaagg aaaccggctt gcccggtcgc atggcgacat caagcacgcc gagcgacccg   25080
ccgcagcgtg tgagcgcgtc ccgcacatga tcctcgccac ccctggacat cccgcctgac   25140
gtcacgacga tatcgtgctc cgtagcacgc ctgtgaatga tattggtggt cgcctcaatc   25200
gtgtccggcg tcgccccgag atcgcggact tcgagccagg gatgcgacag catggaggcg   25260
```

```
aaaaggtagc gattggaatt atagatctgg ccagccgcca agtgctcacc cggctctttc   25320
agttcagagc ctgtcgtaat gaacccgagt cggatctttc gaacgatgga aatccgagac   25380
aagcctgcgg ccgcgagcag cgcaatccgg tgtgctgtca gaaccgtccc ggccttgaac   25440
agcaaagagt tttggtcgac atcttcgccc gccctgcgga tgttctcgcc tgggcgggga   25500
cggtaggcgg tggtgaactg gcgatcatgc cgcgaacatt tttcacggat gatcacggcg   25560
tcgaaaccgg ccgggatcat cgcgccggtg aagatttcca cggcctcagc attttcgaaa   25620
ctgctgctgc tggcctgatc tccggctgcc actctgtctg cgaccagaaa ggtccaggga   25680
ccactgccgg aaaaacccgc cgtgcgaacc gcaaacccgt ccatcgccga atgatcgaag   25740
cgcggcaagg cacagggcga gcggatgtcg gcggccacca cgcggccgcc tgcagaaaac   25800
agatcgaggt cttcggtagc ggtcacgggc cggcacaggc cgatggcgcg gccaccgca   25860 tcggcaaccg acaacatggg gcgagcagct aaggctcgcc cgcagtcgag agcagcgcgg   25920
tcgaacaacg cggcacggtc cgctggcatg taattcatca aggcctccca accacgatta   25980
aagggacagg tgtggagatc gcgacctcct ctgtgaggtc gcgacaccag cgcttcacgg   26040
ggtgctgatt gttttcaggt aagcgatgac gtcggccaca tcctcgggct tcttcaggcc   26100
ggcgaaggcc atcttggttc ccttgatata ggccttggga ttggcgagat actcggtcaa   26160
gtgggcttcg tcccaggtcc agccctcttc ggccttgcc ttgaaggcgg gcgagtagtt   26220
gaagccctcg acgcctgcga ccttccggcc gatgatggca ttcagttcag gaccgacctt   26280
gttggccgca ccctcgccga cggcatggca ggcggtgcat tcttgaaaaa cgaccgcgcc   26340
tttttccgcg tcgccctcgg ccatggcggg ggatgttgca atcaggcaca gtgagactat   26400
cgaaaacagt ttccgcattt gtattgtcca tatgtttgaa ggagtgggcg gcgctactgg   26460
ccgcccacgt ctggagggaa gagtggcagg ggccactcgc tgtgtcctca agccgaccgg   26520
tattctttcg acttgaaggt cagatgagcc acgttttttag gcgcatccga aatcttgcgg   26580
atattgcccc aggtctgctt gtagtttggg atgatcaact cgttcgtgcc ggcgctggtc   26640
acattgccct gcacgccagt cgggaaaccg aacaacatga aggtttcgcc gcggcgtgcg   26700
gtcggtgtcg gataggccat ggcctgggtc gcgccggcat cattgtaaat ctcgacgagg   26760
tccccctcct tgagccccgc ttccaccatg tcctccgggt tcatttcgat gaacggatag   26820
gggaaccggt ccatgacgaa gtcgttttcc tggtcaagat aagcggattg ccagaccaca   26880
ttggcgcgcc cgttgttgat cagatatttg tggttgtcct tctgctgttg cttgcccggt   26940
gcctgcagtc cgcgccacgg tgcgtccatg aagcgcgcct tgccatcgtc ggtcgagaac   27000
acgccgtcgg tatagagccg ctgggtgccg gcgatcttgc cgtcggcaaa accgtcgcc   27060 ggctcctgga atccgttggt gcccatggcg ctcaggcgct cataggtgac gaattcaccg   27120
ccatgagcgt gtctgttgta accgtccatg aaggcgtctt cctcggtctg ccagtcgaag   27180
cccttgaact tgccggcata ggcagcgtcg cccatctcgg tcagcacccg ttccatggta   27240
ttggctagcc gggcggcgat caggcagtcc ggcatggatt ggccgggcgg gtccatgtag   27300
cgctcggtca accgcatccg gcgttcgcca ttcatcgaag tgaggttcat ctcgcccgac   27360
gtggccgcag gcaggatgac gtgacaggcc tcgccgatct ttgtcgggat gatgtctata   27420
ttgacggcga acagaccacc ctggttgatc gcagcgacga tggcgttcac catggcctcg   27480
cggtcgccat agggagcgac gctcatcgca tccttcacca tgtcggtgcg cttcttgtag   27540
acgcgcttga actcgtgggc gttgagggtg gtcttgtagt ggtcgcagcc ccaaatgtgg   27600
tgcacgcccc cttggccgcc gatcagcaac tggtcgacat aggccgccgg ccggccgaca   27660
```

```
tgggcgtcgg acgggcgcac ataaccttcc tggtgaccgc cgaggcgaac gacgccaccg    27720
ccaggacgac cgatattgcc ggtggcgagg gccagattca ccagcgcgcc gttggtgcgg    27780
taattgtcgt tgccccagat caggcccttc tcgtagccga acatgacgcg tcgacgcttg    27840
ccgccttcct tcggcatggc aatccattcg gcggctttga tgatctggga ttggtctagc    27900
cccgttattt tcgcggcttc ctcgatggat acgcggcacc cttcgacggc atcctcgaaa    27960
ttggacaaat gtccaggctt gctgtccgat ccgccacgcg cgggatagag cggcggccgt    28020
gctacacctt cccgcaaggt cgatttgtcg atgaattcgc ggtcaaccca gcccttatca    28080
gcgatgtatg taaacagcgc attgaatagc gctaggtcgc tgccggaatt gatcgcgaga    28140
tgcaggacgt tgtccttgcc agccgtttcc tcgctcgcat tgacggtcac cgtgcggcgc    28200
ggatcgacaa tgataatccg gcccgcttca tgcggctcgt ctggcatgat ctgctttttc    28260
ttctcgagac tttcgccgcg caggttcggg atccagtgat tgaggaaata gtttgtctgg    28320
gtctccagcg cattggtgcc gaccgcgacg atcgtgtcgg ccagttcggc atcctcatag    28380
cagttgttca actcgccgac gcccatgtcg cgggtaccgt ggacttccga attataggcc    28440
gggcggttgt ggatacggat gttccttgacc ttcatggcct cgaaatagag cttgcccgtg    28500
ccccaggtgt tttcgtagcc gcctccggcg ccgccatggt cgaaggccga aacgatcaga    28560
gcgtcctcac ccttctcctt gatgatcttc gccgtcacgc gggcgacaag atcaagcgca    28620
tcgtcccagc tcgtcggctg catctgtcca tagcgccaga cgagggatc cgtcaggcgc    28680 tgttgctggg tgttgcgggc ttcggaaaag ctcgtttcgg ccatcctggc tccgcgaact    28740
gaaccgagac cggtgttcac cacgcattcg tggtccggct tgatgacgac atgaacgtcg    28800
cggccatcct gtttgacgac attgtacatg gatggcgaat accaggcgtc agtttccgcc    28860
tgttgctgct cggacagatc gacgccgaac acgtttttct gcgggtccgt gccgccctgt    28920
ttgttgattg gccaggtgta ggcgtgatag ccgcagccga cgatgcagaa gtggcaggtg    28980
acgttgtgct tctttgcgtc cgcgggaatg atcggcagac ggtcgatgtg acgtttgaag    29040
gccatgatct tcttcccctta tagaacgttg acaggcggc cgtagatgag ctcatcgacg    29100
ccttcggcga agatgtcacc gttatctgcg acgcggagca cgtattgagg caggttctgc    29160
gtggactgtc cccagacctg ctggcctccc ttttcagcat cgaacaccga gaagtggccg    29220
ggacagttga acgtcttgtt gtcggcggta tagctcagcg gaaaacccctt gtgggggcag    29280 atggtagaaa agccgacgat gtcgccatcg ggaccgacgc cgccttccac gcgcgtcccg    29340
agtttgagaa gaacgcccga ggcatcttca tcgggatagg cgacgtcgag aggttcgttg    29400
agggtgagtt ccgagatgtt ggcgagacga ttggcgggat agtccacgcc ggccgcagcg    29460
gtagcggctc ttgcctgtgg cgcgccgacg cccgtgacga cgacactagc gcccgcggcg    29520
gccaatgccc ctccgcgtag gaactggcgt cgaccgatat cgaccatgtt tcgacagcgt    29580
gacatgcgat cctcctccat tgaatgtcga aggtcgaatt gcaatagctg tgccaacagg    29640
tagagggctg atttatcgcg cctttttcgc gaatcttccg tgtgtgggtt cggatttccg    29700
aacggccagt aaccaccgtt gttcagttgg ccgaacgttc actagcttct attccgaaac    29760
gcgtcatttt ctcccaaagg gtcgtacgag aaatgccgag atgtcctgcg gcctgagaaa    29820
tctgtccgcc ggttgcgctt agcgcccgca ggatctgtcg gcgctccgcg gcgtcccgcg    29880
catcggagag tgttccgatc cgcggcgtat cagatacttt ggcgacgtcg gggaatagat    29940
ccgccggcat cacgagcaga ttttccgaca gagcagcggc gcgttccagc cgattgcgga    30000
```

-continued

```
gctcgcgggc attcccgggc aacagtgtt caagcattgc gtcctcggca agcgtactga    30060
tgccccgaac gcgagtctcc ctgatctgca tgatctcctc gagaaagcgc tgagcgagcc    30120
acaggatgtc ttcctgtcgt tcacgcagcg gtgcaagcat gactggaagg cggaaagac    30180 gaaagaacaa gtcctttcga aggaactgg cgtcgctgcc aatctcctga tgggtggcac    30240
agacaatgcg tgccttgaac gggatggatg tttcgctgcc gacccgatga aaccaaccat    30300
cctcgatgag acgaagaagt ttcgcctgca gaacaggcgg catatcaccg atctcgtcga    30360
gaaagagaat accttcgccg gcacgttccg cgtagccgcg atgaagttgg tgagcacccg    30420
taaatgctcc tttctcgtgg ccgaaaagct cgcttttccag cagttcggct ggaatggctg    30480
cgcagtttac ggcgatgaaa ggggcgagcg cacgctttga taactgatgc agaaacctgg    30540
cgctgacttc cttgccagtg ccggtctctc cctgaatgag aacggggagg ggatgagagg    30600
cataacgccg caacatctgt tcggcgtcgc gcatggcgcg ggagatgccg agggagctat    30660
tgagctcatc ctgccgcttg ctccttaagc ttgatgagac gcgatcgagg aaagccgtca    30720
tgtcgaacgg tttggtgatg aagtcgaccg caccactgcg catcagacgc accgcctggt    30780
ctatatcggc gtagccagac atgaataaaa agggtgttgc ggtatcgcgg ctggcctggc    30840
ggaaaacctc ttcaccattc atgtctggaa ggcggatatc gcaaacgacg aggtcgaacg    30900
gttctgatcc gctggcgagc tcgcgcatgg cctgctctcc cttcgtccac catttcacct    30960
tgtggccctc aagcgaaagt cgctggatga gcgactctcc catgatggga tcgtcctcga    31020
gtatggcgat gcgccctgtt tcacgctgca tggctagttt cctccccagg aatcaatatc    31080
ggcaagtgca attcaatgac ggtcaggccg gcttcggtcc ttgacaaacg gatatgtcca    31140
ccggcctcat ccaccagctt ccggaccatc acaggccaa gccctccagc tgactgagcg    31200 gccgccatg gatctggcga tgtaaggaca ttagttgcgg ccttcggcag gcccggcccc    31260
gtatcggcaa ccgagaggat taacgtcgag ccgtcttcct cgaggcatgt ctccacaaaa    31320
atcgtgccgt catcgcccgc agcggcgctt gcgtttagca cgaggttcaa aagtgcttgc    31380
cgcacagtag agccgggcag ggcagatatg gtgagattgg atgggctgct cacccagtgc    31440
atcgtttgtc tgcggcttat aatgacgggg ccggccagta ggcgcacatc ttccagatcc    31500
tgtaggacga gaggctttcc ggagcggtcc ggccggtatg ttgccagtgc tgcctgtaca    31560
acatcgcgaa taccgccgag accacgttcc agaagggaca cactggtgct ccgtacgcct    31620
tcgtttgccc catgtcgctt caacgtgtcg atggagttga acagtcctcc gagcggatta    31680
ttgatctcgt gggccatgct ggatgcgagc cgtcctaaac tggcaagctt ctcttcctcg    31740
gccaatcgac gcgtgagtgc gctgcgctgc tgctcggctt gtaccaaagc gttgaagcca    31800
tgaaacagat cagcgagttc acccgcgcga tacggaaatt cttcagcggg aatggtgtag    31860
ggctgtccgg ccgcaccaga gcgcatgtgt tgtgccaatg tcgccaccgg cctgaccata    31920
cgtctggtca agacgtatcc aactgcggca aacacgaatg ccaagacagc attcgtcgca    31980
agaagcgtct ggagaacctg cgccctttcc gcgacaagat gggtgatgtc gaaagaggcg    32040
tgtacggtcc cgatcgactt tccctgataa aggagctgcc tgatcccgaa cccggtgttc    32100
gactgccatt cgatgcggat ttcatcgtct ttgcctcggt cagcgaaggc cggggggaagt    32160 tcggaaagta ccgggatagc gtgcggatcg ctggaagcca gtaccatgcc atcccgtcca    32220
gtcacaaccg tctcgatcgg agacacggcc gcaaacatcg tacgggtgcg gtcgagcagg    32280
tcataggttt cccatacatc ctgccgcaaa acagccggga taagagcggt ggacaagcca    32340
tcgaaatagg ttcccacgac gccgttcaga tgctgttcct gcatgtcatg aaggcgagcc    32400
```

```
aatacgcgtt cggagatgat gaggctgacg acgatcatca gggatgccac cattaccggg   32460
acccgaaccg tcaagggaat gccgcgaacg cgctcgatga ggctcacccc agcctccgaa   32520
cccgttccat gttgaccgcg atactttcgt agctttcggg tggaacctga gtgaacccgt   32580
caagctggag gcgctcaagc accgttcggc ccagctcgtc gctgtgcatt tgcaggagcg   32640
cgtttcttat tctggcaacc ggctggcttt cgcgctgtcg tgcggcggct gcgatgggcg   32700
ggaagccgtg ccagtcagac ttcaccagta ccctcgtttt cgagagcagt tccggttcgg   32760
tctgtttcat gacttcccag acgtacccat caacgctccc ggaatcggca aggccggaag   32820
ccactgcccg gatcacattg cggtggccgt aggtaaaaaa tgacttgcga aagaagcctt   32880
cctcggagac gccgcgttcg gccagatagg ttttcgtgac gaggtagccg gaattggaat   32940
cggggtcgga gaacgcatgg atatcccccc gacagtcatc aaaggcctgg atgtcacgat   33000
gttgaccgac gatgaggtag gattggtaaa gcggcttatc acgccacaat ggcgtggcaa   33060
ccagctccag ctcgtcccgg aacttcatga acgggtagcc gcaaatccag gcggcctcaa   33120
gattccccga gaccaggagg gcagtgactt cctggtaggt acgctgtgtg acaagttgta   33180
cttcttgacc aatagcgcgg actaggtagg cctgtagttc gtccagcact tccaggtcat   33240
tcgatagaaa gacgggtgtc aacccaaacc gaatcacgcc aggtcgcggc ggcacggaca   33300
gcaactcgct tcccgcaggc gatccggcga agcatatcgc ggacaaagct ccgcctatcg   33360
ccatccggcg cgatatacga cacttgtcgg cgtgccgacc gcgcgtgtgg tctcgatttg   33420
acaccgacga cctccctcag ctctcctcca gagcctaaat caattgtact gtcttcagac   33480
agattgtcca accgctcctc cgggattgag gtgctggttg catggatctc aggatttcgc   33540
ccgctaccac cttttgcaa ctatccggga cgggtgaaga cacagaccgg gagcggtgaa   33600
attttacttc aaacctgtat ccattgaata accggcgcct ctaacggtcc ggatcaggtc   33660
tggcttgttg gcaaagttaa gggcttttct gagccggccg acatgaacgt cgaccgttct   33720
ttcgtctaca tagagatcgt gaccccaaac gccgtcaagg agctgtgctc gggagaagac   33780 gcgcccggc gacgccatga gaaaatcgag gagacggaac tcggtcggac cgagcctgac   33840
ttcacggcgc tcgcgatgga cacgatggct ttcccggtca agctcgatgt cagcatagcg   33900
caaaatggac gagatcaatg ctggtttgga acgcctcagc agagctctca ccctggccat   33960
aagttccgga gtcgagaatg gcttcaccag atagtcatcc gcacctgtcg ccaatccccg   34020
cacacgctct gtctcctccc cccgtgccgt cagcataatg acggggagcc gctccgtgtt   34080
tggtctggcg cgtagacggc ggcaaagttc gattccggat acaccgggaa gcatccaatc   34140
cagaattagc agatccggca cgcttcctg cagaactatg tcagcctctt cgccgtggcc   34200
gattgtctcg acaaggtatc cttcggcctc gaggttgtag cggagcagaa cactcagcgc   34260
ttcctcgtct tcgacgatca tgacctttgg ggacatcagc ttcgctcctt agtttcgcgg   34320
ctgtcaggcg atttattaca gtgacacttc agttttgtga caaacgcgaa atatctagaa   34380
atctggaaat atgattgtca tcgtgaggat tttgggatat cctgcaaacc tctcgccatc   34440
gtgggtgcat cgagagcgac gcatctctac ggttaaattc cggataatat tttcgtcaaa   34500
tcatgtatta agcaagtaaa aaacttccaa ctcaaatatc aatctatcta gatataccat   34560
actatacttg gttgacataa aactgtcatc caacaatact atgaccgccc tgcgttcgcg   34620
gatgtcgcgt tcagcttttc tgaattcaca gagggtcgtc atgacacaca acacgaaaac   34680 cttttcgcccg gcgcgcgccg ccttcgcctc ttccgcagct tcgatcgtta ctctcggcct   34740
```

```
cctcgttgcc ccttcttttg cgcagcaggc accgacagtg ctgatcgacg gctcgagcac   34800
cgtattcccc atttccgaag ccatggctga agagttccag aaggctcaag ccggcaaaac   34860
cctggtgacc gtcggttctt ctggcacggg cggtggcttc aagaagttct gccgcggcga   34920
aaccgacatc accggcgctt cccgaccgat caagtccgac gagatcgaac tgtgcaagca   34980
gaacggcgtt gaattcatcg agctgcctgt cgcaatcgat gctctcgcaa cgatcgtaaa   35040
cccggcgaac gactgggcga cgtgcatgac cgtcgaggaa ctgaagaaga tttgggagcc   35100
tgaagcacag gggaaggtca cgaactggaa ccaggtccgc ggcgaattcc ctgacgccaa   35160
gctcggcctc tttggcgccg gcacggattc cggaacctac gactactaca cgttcgccat   35220
taacggcaaa gagcatgcca ccgcggcga ctataccgcg accgaggacg acaacatcac   35280
gatccagggc gtcggcggcg acaagaatgc gatcggcttc ctgggtctcg cctatctgac   35340
cgagaatgct ggcaaggtga aggctgtcga aatcaagcag gccgatggat cgtgcgtggc   35400
gccgtccatc gagacagcca ccgacggaac ttaccagccg ctcacccgtc cgcttttcta   35460
ttacgcttcc aagaagtcag ccgaagaaaa ggaacatgtg cgtgccttcg cggagttcct   35520
tttcgatgcc aagaaccagg aagaactcgt cagcgaggtc ggctatgtcg ccctgcctgc   35580
cgaagccgct ggccttgctc tgaagaagtt cgaaaagcgt gtcaccggga gccacttcga   35640
aggcggttcc aaggtcggcg tgacggtcac cgacctggtc gccgacgcag ccaactaaca   35700
tcccaaccct cccggcagtc gcgagtactc gcggctgccg tcagtggagc tcaagatgcc   35760
aacaacgctc gacgcctata ttccaagcga cgctttctg aaacggcgac gtatcatcga   35820
cctgtcgatg cgcgtgttgc ttttcttgtc cgccgctctc tcggtgcttg tcaccgctgc   35880
catcgtttac gtgcttgtaa gcgagtcgtg gaatttcttc accgaggttt cctttggac    35940 gttcctgacc gataccgagt ggacgccggt ctttgcgcag cctcgctacg gcattctgcc   36000
acttcttaca gcaaccctct gggccgccgg gatcgcgatt ttgatcgcaa tcccttggg    36060 aacaagcctc gccgtctacc tcagtgagta tgcgcgcccg gccgtccgcg aaaccgtcaa   36120
accggtgctc gaattgctcg gcggcgtgcc gaccgtcgtc tttggttatt cgctctcct   36180 gtttatcact ccactgcttc agacgttcat tccggcctg accggcttca accttctggc    36240
tcccggtatc gtgctcggca tcatgatcat gccctacatc gtctccatca gcgaagacgc   36300
gatgcgtgcc gtgccggcct cattgaggga aggcgcttac gctcttggca tgacgaggct   36360
gcagacgtcg ttcagggtca tcattccggg tgcgttctcg ggcatcaccg cagcgtatct   36420
tctcggaatg tcacgggccg taggcgagac catggtgctt gcaattgccg caggacagaa   36480
ccctaatctc accgcagatc ctcgcgaagg cgctgcaacg attacgtcct atatcgtaca   36540
gatgagcctc ggtgatctgc cccatggctc gctggcatat caaacgattt tcgctgcagg   36600
cctcgcactt ttcgtgctga cccttgtttt caacatcatc ggcttctttc ttcgccgccg   36660
cttccgggag gcttactgat ggctatcaca gcagacagcc caatcgtggc tctcgacatc   36720
gattcccaga cctcgctcgt caatcgagca cgacgcaacg acttcatatt cgccggcttg   36780
ggtctcacca tcttgttcgt ggttatggct ttcttggtcg cgttgatagc cgacctttc    36840 tacgacggac tgggccggat cgattacgcc ttcctgaccg agtttccgtc acggcgaccc   36900
gcagatgccg gcatccttc ggcctgggtc ggaacctgcc tggttatgtt cgtcacggct    36960
ttgctggcca ttccgcttgg tgtcggtgcg ggtctttacc tcgaagagta tgcgagaaag   37020
aactggatga ccgacgtcat tgaaatcaac gtcaccaatc tcgctggtgt accgtcgatt   37080
atctatggtt tgctcgcgct cggcttcttt gtctatctcg ccgatcttgg ccggacggtt   37140
```

```
ctggtcgcgg gcatggtgct tgcgctgctg atcctgccga tcgtcatcgt tgcgacgaga   37200
gaggctataa gggcgatacc gcagacaatc cgcgaaggcg ccttcggtct cggtgcggac   37260
aaatggcaga ccatgtggca ttacattctt ccggctgcgc ggcctggtat ccttaccggt   37320
gcgatcgtcg gcttgtcccg agccatcggg gaaaccgccc cgatcatcac gatcggcgct   37380
ctgaccttca tcgcattcct tcctcctgcg cctgtggatg cgagctttcc ctttatcaac   37440
tttgattggc tgaatgcgcc gttcaccgtg atgcccatcc agatgttcaa ctggatatca   37500
cggccgcagg cagcgtttca catcaatgcc gccgcgactg tgttgtcct gatgttcatg    37560 acgttgggca tgaatgccgt cgccatctgg atacgcttca ggcttcgacg caatcttggc   37620
ctctaactga gatcggacca aaaatgaacg acacttcgac cgtcagtaaa cctgccagag   37680
tgggccagca aacaggttca gcgcgcaaca ttctgatcca tcccgaacgc ctgcgcgctg   37740
aagtgaggga tctcgatttc tggtacggag aattccacgc gctcaagaag gtcaaccttc   37800
ccgttgcgga aaagcaggtt actgctttga tcggcccgtc aggctgcggc aagagcacgc   37860
tcttgcgatc gttcaaccgt atgcacgatc tttaccctgg caaccggtac gagggcgcga   37920
ttgaactgct gccggaaaag aaaaatttag tggctcaggg catggatccg atcctgatcc   37980
gcttgagcat cgggatggtg tttcagaagc caaacccgtt tccgaaatcg atttatgaaa   38040
acgttgcagc cggcctgaaa atccgtggca tcaccaagaa gagccttctt gatgagcgag   38100
ttgagcaggc tcttcagggc gcggcactct ggaatgaggt gaaggaccgc ctccatcagt   38160
cagcctatgg cctttcggga gggcagcaac agcgtttgtg catcgcccgt acgctggccc   38220
ccaatcccga aatcattctt ttcgatgaac ccacatcggc tctggacccg atcgccaccg   38280
cgaaaatcga ggagctcatc gcggagttgc gagaccagta cacgatcgtc atcgtcacgc   38340
acaacatgca gcaggcagcg cggatatcga catacaccgc ctacatgcac ctgggcgaga   38400
tgaccgagta caacgcaacg aacgagttct tcacgaatcc gcagaacgaa aaaacgcagc   38460
actacatcac cggtcgcttc ggttaagggg gaaacatgac gatggatcac actattcgag   38520
ctttcgacga ggaactgcag gacctgaccg gacaagtatc cgatatgggg cgaatcgctg   38580
cagcgctcct cgacaagtcc gtcaatgctc tcatcggcaa cgacaagaca ctggcagatg   38640
aggtcgtaag ggccgacctt caactcgatg ccatgcagag aaccgccgaa acggcggctg   38700
tgcagatcat tgctcgcaga cagcccgtcg cgaacgacct cgacggatc gtcggggcga    38760 tgcgcatggt ttcaaacctg gagcgtgtgg gcgatctcgc caagaacatc gccaagcgcg   38820
ctgcaatcat ggatgcttca cttaacaggg gtgttgtctc tgcagggttc agcacattgg   38880
ccgaagccgc caaaacgcag ctggctggcg cgctcgatgc tttccagaac aacgacgcga   38940
aggcggcatc tcaagtccga ctccaggacg agcacatcga tgtactctat aacggcctct   39000
ttcgagaact cctgacatac atgatggaag accagcgctc gatcacattg tgcgctcacc   39060 tcctttttg cgccaagaac ctggagcggg tcggagatca tgctaccaat cttgctgaga   39120
ccgtcgagta catcgtgacg ggcgatgatg tttcgactga tcgccctcgc gccgaaactg   39180
tcgttgcgat ggagtagact tcatgccgag cgtcgttatc gtacaggaag atattggcgt   39240
tggctcgatc ctggaagcaa gcttccgcga ggaaggttat atcgccgggg tatgtggact   39300
ggccgagcag tgcgaacgta tggtagcaga aaggcaacca gatctggttg ttgtcgattc   39360
agtgagccgt gcgaccaatc tccgtcagtc gtttatgaaa atgcgagccc atgtgcgcag   39420
aaggcagttg gcgatcatcg tcttgggcgg agaggcgctg cccaagcccc tttttgatgc   39480
```

```
cggagctgac gattacttgc cgcgcccctt ttccgttcag gaacttctcg ctcgcagcaa   39540
tgcgctcctt gagcgttcat gctcgaagac gaccaggata ttgaaccatc gcgagatatc   39600
cctgaacgtc gaaacgcaca gggtttcgcg gaagggacgg gagatccacc ttggtccgac   39660
ggaatatcgt ctcctgcaga cgatgctgac agaaccgtcg cgactgtttg cgcgtcgcga   39720
gattcttgag atggtgtgga acgacaccag ccgggatgaa cgcatcgttg atgtcagcat   39780
caagcgattg cggaagtcct tgaacatcgg aagcaaggaa gacgcaattc gtactgtgcg   39840
cggctgcggt tacggcctgc agtaatagcg atcagggtag actgtttccg attgccctca   39900
actgcgtttg aagggacatc ctgtcgatcg actcgatcgg aagcgcggtg aagacggaga   39960
gcctgttggc gatagcgtct gccgcccgtc gaaaggcggc gagcctttgc agttcacttc   40020
cctcaacaag cgtgggatcg tcgatagccc agtgcgctgt aaaaggctga ccgggccagg   40080
aggggcattg ctcccccgtc agtgtatcgc aaacggtgaa gacgaaatcc atagcgacac   40140
ggttgagacc tttgaactcg tcccagctct tgggcctgag gttctcgatt ggacagtcca   40200
tcttctgaag tgttgcgagt gtcatcggat gcacctcgct tgcgggaaga tttcctgcag   40260
agaacgccgc aaaccgcatc ggcgccatct tgcgcagaat ggcctccgcc atgatcgatc   40320
tggcagaatt tgcgcggcat aggaaaagca cattgaaaat gcgtggtacc tgttggtctg   40380
gcttggttct ggtcgacgag gttttgccag ccatggggt aaagtccgtc gccaaaaact   40440
cgaccagcct ccagacaagt tcggtgttcg gccgataaat tatcgtggtg ccaacgcgtt   40500
gggtctggac cagtccagca cgcttcaaca cgttaagatg agacgacatc gtattttgag   40560
gcacatcgag cagtcttcct atgtcgcctg agggcaatcc ctccggcgaa tgatccagga   40620
gaagacgcag tgcatcaagt cgggtggttt gcgcgattgc agcaaatgcc tctacgatag   40680 ccgattttc cataagtctg gatatataga ttttcgttta gttgagcaag ttgcgttccc   40740
ttggcgggcg acaataaatc cgtatttctg gaaatgtgca gttctgtcat atttctgtgg   40800
cgcaagtgcc gaataagcgg gtgtctgttt tggatcgatg gagaacctga tgaaaaagct   40860
cgtggccgca ctggcgataa ccgtagcatt tgcaatgcct gctcaggcag aattcaaact   40920
cgacgcccgc tacacggatg cggacggtga catggtcgcc gacattccga cggatgccag   40980
ccagctcgca gaccctgata cgctggtgtt cgcctataca ccggtcgaag atccggctgt   41040
ttacgccgat gtctggaaag gctttctcga tcacctcgcg gaaaagaccg gcaagaaggt   41100 tcagttttc ccggtgcagg aaaacgccgc tcagatcgaa gccatgcggg ccggtcggct   41160
gcacgtgtcc ggctttaata ccggttccaa tccgatcgct gtcgcctgtg ccggcttccg   41220
gccgtttgca atgatggcct ccaaggacgg cgccttcggc tacgagatgg aaatcattac   41280
ttatccaggt tccggggtcg agaagatcga ggatctcaag ggcaagaagc tcgccttcac   41340
cgccgagaca tccaactccg gtttcaaggc tccatcggca ttgctgaagt ccgagtacaa   41400
gctcgaggcg ggcaaggatt ttgagccggt tttctcgggc aaacatgaca attcggtcct   41460
cggcgttgcc aacaaggact acccggctgc ggctgtcgcc aattccgtca tgaagcgcat   41520
gatcgcccgt gatgtcgtca aggcggacca gattgtctca atcttcaagt cgcagacgtt   41580
cccgaccaca ggttatggcg tggccccacaa tctgaccccg gaactgcagg aaaagatcaa   41640
aggtgccttc ttctcctaca actgggaagg ctcggcgctc ctgaaggaat ccagacatc   41700 ggagccgccg caggaaagtt tcatcccgat ctccttcaag gaaaactggt ctgtcgttcg   41760
ccagatcgat gaagccaacg gcgtcaccta cgcgtgcaaa taagcacgtt tgaccaataa   41820
gcgccgggtc gtacgcgacc cggcgcttac tcatgtttta aaggcgggga acgagaatgc   41880
```

```
tcaggatcac ggggctcacc aaaacctaca aaaccggcga caaggcgctg aacgggatca   41940
cattggaaat ccctgccggc caggtggtag gtttgatcgg tccttcggga gccggcaaat   42000
ccagtctcat ccgttgcgta aatcgactga ccgaacccac gtcaggcaag atctttctag   42060
gcgagcgaga cgtgaccgcg ttgtctcggt ccgatctcag ggtcgcgcgc cgccgtatcg   42120
gcatgatctt ccaggaatat gctctggtcg agcggttgac cgtaatggaa aacgtgctct   42180
ccggtcggct cggctacgtg cctttctggc gcagtttttt acgccgctac cccgcaggct   42240
acgtgcagaa cgcattcgca cttctggagc gcgttggttt gacggcccat gccgacaaac   42300
gcgccgatgc tctctcaggc ggtcagcgac agcgcgtcgg tatcgcacgc gcgctggagc   42360
aagaccctga actgcttctg gttgatgagc cgaccgcttc gctcgaccct aaaacctcac   42420
ggcaaatcat gaggctgatc gtcgagatct gcaaagaacg aaacctgccg gcggtcatca   42480
atatccatga cgtcctgttg gcgcaggctt tcgttcaacg gattatcggc ctgcgtgctg   42540
gcgaggtagt cttcgacggc acgcctgacc aactcgacac agctgcactc acccgcatct   42600
atggcgaaga ggactgggtt gccatgcaga agcaagccca ggatgatgcc gaagaagagc   42660
tccttgcagt tattgaacga gaacgggcgg aagagcgctt ggcaggagcc ttgtgatggc   42720
ccatgtactc tcgacgagct atccttcggt gtggcggcgg ccaccactgt tcatcaggtc   42780
ggcggttttg cgctggctga tctatggggg cgcgctgatt tatatcatcg ttgccgttgc   42840
gaccatcgat gtaaactggg cgcgtgccta cgaagggctc gatcgcggct ggcgtttcct   42900
tcaaggcttt ctggtcccaa actttaccac gcgctggcgt gatatcgcac agggacttga   42960
agagagcctg acgatgacgt tgacttcgac tatcgtcggt atcctcgttt ccatcccgat   43020
tggcatcgga ggggcgcgca atcttgcgcc agcgcccgtc tactacgtgt gccgctcaat   43080
cattgccatt tcgcgtgcct tccaggagat catcattgcg atcctgctcg ttgcaatgtt   43140
cggtttcggc ccgttcgcgg gtttcctgac gctcaccttc gcaacgattg gctttatcgc   43200
caagctcctc gctgacgcta tcgaagaaat cgatgaaaag caggcagagg ccatccgtgc   43260
caccggcgcg tcttggctgc aactcgtcaa ctatgcggtc caaccacagg taatgccgcg   43320
actgataggg cttcgctct accggtttga catcaatttc cgtgaatcgg ccgtcatcgg   43380
catcgtcggg gcaggaggta tcggtgcaac gctcaacacg tcgattgacc gatacgagta   43440
cgatagcgcc ggtgctgtgc tgatcctcat tatcgtcatc gtcatgctcg ccgaatacgg   43500
ttcgagctta attcgcaagc gggttcaata atgccagttt cacattccct tgatggcagc   43560
aagacatggc gcaagctcac gccgagccgc gagctcattc agtggatcgg ttggctgcta   43620
ctcgtcgcct tcttcatgtt ctgctggcag atcatgacaa aagatacgat ctgggcgttt   43680
atttacgatg cgccccggca aggcggcgac attcttagcc gcgcctttcc acctcgcctg   43740
ttttatgtaa gcgagctcat cactccgctt tgggacacgc tcaacatggc gacgcttggg   43800
acgcttttg gcactgtgct ggcggtgcct attgcttttcc ttgccgctcg caacaccacg   43860
cccagcctgc ttgtccttcg gccgatcgca cttttcctga tcgttgcatc acggtccatc   43920
aactcgctga tctgggcatt gcttctcgtc tcgatcctgg gacctggact gcttgccggc   43980
atcattgcga tcgcccttcg gtcaattggc ttcgtcggaa agctccttta cgaaacgatt   44040
gaggagatcg accagaagca ggttgaagct atctcatcca ccggggcaag tcgcatacag   44100
gttatcgact acgcgattgt gccgcaggtc ctgccttcgt ttctgggaat taccgtgttc   44160
cgctgggaca tcaacatcag ggaatcggcg atcctcggcc tcgtcggtgc aggcgggctc   44220
```

```
ggcctcaagc ttcagtcctc tttgaacatg ttggcctggc cccaggtaac gacgatcttc    44280
atcgtcattc tggccacggt tatcctggcc gagtgggtct cggcagctgt acgcaaggcg    44340
ctcgtgtgag cctgtttaac gtcaaggctt tcgggtcccg ggcaaggccg tctgcagtgt    44400
tgcagtctaa gttcgtgcgt tcttattcaa agtcgagggc aggcgctgct gaacaaacgt    44460
gttgacttcg tccataattc cagtaatctg gatatatgga acaggaacaa gcaattctcg    44520
ctcttgcagc gctcgcgcaa ccaacccgtc ttgagacttt tcggttgctc ataaaacacg    44580
cgccggaggg gctgccggct ggcgatatag cgcgtgcgct cgtggtgccg caaaatacca    44640
tgtcggcgca tttgaacatt ctgtcgcggg ccgggctcgt aacctcgcaa cggcacagca    44700
ggatcatcat gtaccgcgct gagctcgaac agcttcgcga tatgacgcta ttccttctga    44760
aggaatgctg tggtggatcc gctgaattgt gtgcgccact catcgctgaa ctgacaccgt    44820
gctgtgtccc gaccccgcag gaaagtctcg catgagtgcg ctcagggtag aacgattaga    44880
cgggagcgat ctcgaatcag gcagcgacat gttccttgct accaagaggg catcgccgct    44940
ttttgcctgc ctcgtgttca tcgaagtttg acgggaaaat ctgccagccg cagtgcttgc    45000
cacacggcag ctgtcctctc tgcccatcat cggcgacgat catgaaatct acccgaccac    45060
taacttaaca cacggatcac agacatgacc gaaaagacct ataacgtgct cttcctgtgc    45120
acgggcaatt ccgcacgctc cattcttgcc gaagccatcc tcaacaagga aggcggcggt    45180
cgcttcaagg cttactccgc tggcagtcag ccgaagggcg aagtcaatcc gcacgcgctc    45240
aaggaactcg cggcgctcgg ttacgcctca acaggcttct cgtccaagag ctgggatgtg    45300
tttgccgagc cgggtgcgcc acagatggat ttcatcttca ccgtttgtga cagtgcagcg    45360
ggtgaagctt gcccggtatg gatcggtcac ccgatgacag cccattgggg cgtcgaggat    45420
cctgcatctg tcaacggaac cgaagtcgaa attcagcggg cattcgcgca ggcggcgcgg    45480
tttctgaaaa atcgtatcac ggcattcctg agccttccgc tcgaatccat tgatcgcctg    45540
gccctcgaaa cacggctacg gcagatcgga acgatggaag gaacgaccgg tgttcgggaa    45600
gcgaccaatt aaagccagat gacggattcg gccgaagtga agaaacgcgc gccgttaatt    45660
cgtcggccct cgacctccat actttctctc cagtcaaaca aaaggcccga cgtcgcatga    45720
ccaaccccgt cgatatcgtc atctaccaca acccggactg cggaacttcg cgcaacacgc    45780
ttgcgatgat ccgcaacgcc ggcatcgaac cccatgtggt cgagtatctc aagaccccgc    45840
cttcgcgcgc gctgctggag cagttgatcg accggatggg aatttctgcg cgtgaccttc    45900
ttcgcgaaaa gggaacaccg ttttccgaac tcggtctggg cgacacatcc ttgtcggatg    45960
agcaactggt tgatgcaatg atggaacatc ccatcctcat caaccgcccg atcgtcgtca    46020
cgcctgccgg tgtcaagctg tgccgaccat cggaagtggt gctggatatc cttccagccg    46080
atcagcaggc tgcgtttacc aaggaagatg gcgaagtcgt cgtcgaccag accggtcgtc    46140
gcgtggtcta acgtaagtca attcaagctg aacgcgtgtg accgcagtct tcgttgcaag    46200
gctgcggacg atgtttatct gccaaggaga gcgccaatgc gtcccgaaga accaacactg    46260
cgcctgtcgt ttctcgaccg ctatctgacc gtctggattt tgccgccat ggcactgggt    46320 gtgctgctcg gtaccgtctt taccggcctg cctcagcgc tcgacagcct ttccgtcggc    46380
accaccaata ttccgattgc catcggcctc atcctgatga tgtatccgcc tctggcgaaa    46440
gtgcgcttcg aggaattgcc gcaggtgttt gccgacaagc gggttctggc gatttctctc    46500
ctgcagaact ggataatcgg tccggtgctg atgtttgcac tggcggtgat ttttctgcgg    46560
gactatccgg aatatatgac cggtttgatc ctgatcggtc tcgcccgctg cattgccatg    46620
```

```
gttctcgtct ggaaccagct tgcaaggggc gacaaccagt atgtcgcggg cctcgttgcc   46680
ttcaattcga tcttccagat cctgtttttc agcgtctatg cgtggttctt cctgtccttc   46740
ctgcctccgc tgtttggcct tgaaggcagt gtgatcgacg tctcgttctg gacgattgcg   46800
gaagcggtgc tgatctatct cggtattccg ttcctcgccg gttacctcac gcgccgcttg   46860
ctgactgcga aaaagagcag ggattggtac gagaacgtct tcctgccgaa gatcagcccg   46920
atgacgctgg cagcccttct gttcacgatc gtcgccatgt tcagcctgaa gggtggggat   46980
gtggtccgcc tgccgggcga tgtggtgatg atcgccattc cgctgacgat ctactttctc   47040
atcatgtttc ttgtcagctt ctggatgcg aagtccgtcg gcacggatta tccgcgcacg   47100
acagccgttg cctttacggc ggccggcaac aacttcgagc ttgccattgc ggttgccatt   47160
gctgcttttg gttggcctc gccggtcgca tttgccgcgg tgattggccc cttggtcgaa   47220
gttccggtgc tgatcttgct ggtgcaactg gcactctgga tgggccgcaa gtattttaca   47280
aagtcggccg gaaacccggc tgcgtaaaaa gtaaggaagc gcaatgtctt cggacatttt   47340
cgatgtcgtc gtgatcggtg cgggccaggc tggcctcgca tcggcttact atctgcggcg   47400
tgccgacgtc agattcgtga tccttgatgc tgaagaaggg cccggtggtg catgcgaca   47460 tgcgtggaat tcactccatc tgttttcacc ggcatccttt agctcgctgc cgggatggat   47520
gatgccggcg aagaccgagg cggcctatcc gtcaaggaat gaggtggtcg attatctggc   47580
gcgctacgag gagcggtatc attttcccat agaacgcccg gtcgcagtga cgtcggtccg   47640
caacgtcgaa ggcgctctgg aggtcgtcgc cgatagcaga cagtggcgag cgcgtgccgt   47700
tctgagcacg accggcactt ggcgacatcc tttcgttccg gactatgccg gtgcctctgg   47760
cttcaagggc gtgcagattc attcggcgga ttatgtctcg gctgatccct ttgtgggcca   47820
gcgggtcgcc atcgttggcg gcggaaattc cggggcgcag atacttgccg aagtatcaag   47880
ggtcgccgaa accatctggg tcacgcctca ggaaccggtg tttttgcccg atgaagtcga   47940
tggacacgtg ctgtttcagc gcgctaccgc acgggtgctt ggcggggaga gtggcccagc   48000
agttggcagc cttggtgata ttgtcatggt tcccccggtc cgggacgcac gggatcgcgg   48060
cgtgctgggt tcggtgcggc cattctcaaa ctttgatcgg gatggcgtcg tctggcagga   48120
cgatactaga agcgatcttg acgccgtcat ctggtgcacc gggtttcggc cagcgctcga   48180
tcatctccag gatctcggcg tgatcacgga cgatggcagg gttgatgtgg atgagggcg   48240 ctcgattaag cagccacgcc tttggcttgc cgggtatggg aattggaccg gggctgcctc   48300
ggcgacgctt ctggggtcag gccggacggc ccgcgagatg atcccgagac ttgtcgcggc   48360
gctgtaggcg cgcaatcccg atgaatgcga caattgcact tgcacccagc gtggtggtaa   48420
tgacgagcga ccacagcgtg ccgatatggg ccatggcaaa cgctagcgca aagggtgcgg   48480
tggccgacag gatcaaccgt gcggccatga ccttgccttg cagcctgccg tagccatcgc   48540
tgccaaacag catcagcggc aaggtaccgg tgacgatgct gaaaagaccg ctgcccaaac   48600
cgaagacaac ggcaaaagcc atggctcctg ctaccgacgg agcggtgagg gtcaggatga   48660
gtacgccccc ggggatcaat gtggcggcaa tcgttgccaa agcgagcggc ggcagattgc   48720
cgccgagcac catgttggca aaccggctca gcacctgcga cggaccaaac agcgtgccga   48780
caatggcggc ggtggcccca aggccaagcc ccgacagcag cggcaccata tgcaccagga   48840
tcgccgcact gacgagagat tgcagcgaga acccaccac catcagcttg aacccgaact   48900
gccggacgtc cgggctgaga cttccctcca cgatctgcgc cgtgccggct tgtttctgtg   48960
```

```
ctctacccct tggcaaggccg taagacagcc aggcgtggag cggcaggcag acgagcaagt   49020
tgagcgcggc gaacaccagg tagacattct gccaggagag atgggcgtgc agagccgttg   49080
tgatgggcca gaagatcgtt gaggcgaagc cggcgatcag ggtcagatag gtgatgctgc   49140
gctgggcggt gcgggggctt gcctgcacca gcagcgcgaa ggcggcgcca tattgcacga   49200
gattggcggc gatttcgacc acgatcaggg cggcgacgaa gccgctcttg cccggcgcat   49260
aggcacagac gatcagcgcg gctgcggcaa tcgcggagcc ggccgtcatc acctgtcctg   49320
cgccgaaatg atcaatggcc cggccaaggt agggcgcagt caagccgcct agaagaagtg   49380
ccgcggaaag tgcggcgaaa atccactccg tagaccagtt caggtctcgc gccatatcgg   49440
gtgcaaggat gctgaaactg tagtagaggg ttccatagcc aatgatctgg gtgaggccca   49500
gggcaaggat agtgccgacc ggcgggcgct cgctcatatt gatttcgagat ccacgcgctg   49560 ttcgagcttt gcggcctctt ccttcctctc gctatagcgg tcggtcaggt agtcggaggc   49620
atcgcgggtc agcagtgtga acttcaccag ttcctcgcag acatcgacga cgcgatcata   49680
ataggcagag ggtttcatgc gaccctccgt gtcgaactcc tgccaggcct tggcgaccga   49740
cgactggttc ggaatggtga tcatccgcat ccaacggccc agtatccgca actgattgac   49800
ggcgttgaac gactgcgagc caccggagac ctgcatgacg gccagcgtct ttccctgtgt   49860
cggtcgcacc gaaccggtcg tgagggggat ccagtcgatc tgggccttga tgatgccggt   49920
catcgcgccg tgccgctcgg ggctgaccca gacatggcct tccgaccaca gagaaagctc   49980
gcgcagttcc tgaacctttg ggtctgtatc cggcgctcca tcgggaaggg gcagaccctc   50040
gggattgaag atctttacct cgcatccgag gtgctcgaga agccgtgcag cttcttccgc   50100
caaaagacgg ctgaacgaaa tctttcgcag cgatccgtag aggatgagga tccgtggctt   50160
gtgctgcgaa taagccgggc gaagcgcgtc aaggtcgggc tggaaatga gatcaagcga   50220 ggcggctggc agatcggcca ttggggctac tccgtattgt aggatttagg cgtttgtatt   50280
ccggggccgt tatgaatctg atccggcaag ttctgggggc acgtcaccgc cgtcagattg   50340
acccgaacaa cagttctcca tcaggaaatg agcgaggccg ttgagggtct cgaagctcgc   50400
gctgtagacg atggagcgtg actcccgctg agcactaatc agaccagcat gttccagttc   50460
tttgagatga aggaaatgt tggaaggcga gacgttcaca gcttcggcaa ttatacccgc   50520
cgccaatccg cccggaccgg cgacgacgag cttgcgaatg acctgcagtc gggtctgctg   50580
tgacagtgcg cgaaacgcat ccaggacctg ccgctcgttc ataaaatcca atcctcgtaa   50640
aagcgttcta aggtgccagg atatacaagg cttcggcacc tgcgggggat gatcgtattt   50700
cacaccccac ttgttttcat atttcaacta atattgaaat tatgagttag ttgcggctac   50760
gtcaagaagt gttttgcccg tcagtggacc agaagcagcg gaagatcggc tgcagccaaa   50820
acttcccgcg tttcgtgacc catgagccat tccagccact cgctatgact aaaagccccg   50880
gtgaccagaa cgtccgcttt cagggcatcc gcttcacgga cgagctgcgc gccgatcgtt   50940
ttgtcggaac ggggcagaat atgaacttct ggtgtgacgc ctgagccttg catcacagta   51000
tttagcgtcc tatcggcgtt gctttcatcc gttacgcgaa gtgcgctgac acgttctgcg   51060
gcttcgagcc atggtccggc agtctctatt gcgcggcgag ctagatcgct gtctgtgagg   51120
cccacggcga catgcgaaaa ccttgcgcgc gctcctgctt tccaaccggg cggaaccagc   51180
agaaccggcc ggtgcgccgt gaagatctca gcgtggaaag catcggcggc atccatgttt   51240
ctattatgcg acaagacgac gagggcgata tccgcggtcg tctcccgtaa aacggtctgc   51300
gcctccggcc cggtaatcgt gcgcaattct atcgaaggcg cttcgggtcg caaaactata   51360
```

```
ttccattcgc cgaacgcgga tttgatagcg tccgcacgct gttgcagcga gccttcgtca   51420
tgggtgcgaa gctcctgcat gtcgatttcc tcgggagggc agacgagatg tgcaggatcg   51480
acgatgacat tcaacgcttc gatcgacgag caggtcacgg atgctgccgc cataactgca   51540
gcatccatcg ttcccgcgac tgtatcgcct tttgtcagta cagccagaat tctcatgtta   51600
gtgctcccat catttcccga accgtgcagc accaccaagt tctgcctcga tctccagcag   51660
ccgattgtat ttcgcaatcc ggtcagagcg cgaggctgaa cccgtcttga tctgaccgcc   51720
acccatggcg acagcgaaat cggcgatgaa gctgtcttcc gtctcgcccg agcggtgcga   51780
aatgacatag ttccagccgg cattacggca gagctggatc gcgctgatcg tctcggtcac   51840
cgtgccgatc tggttgagct tgatcagtgc cgcattgcag gccttctcct cgatacccct   51900
tgcaatgaag tgggtattgg tgacgaggtt gtcgtcccg acgatctgaa tccggtcgcc   51960
gagagcgttg gtgatggcct tgtagccgtc ccaatcgttc tcatcatggc tgtcctcgat   52020
cgagacgatc gggaattttt cgacccaggt ctcgaacagg ctgaccatct cctcggacgt   52080
cttgtttcct tgcccgctgc gcgtcaggcg atagagcccg tcctcaaaga cgaactggc    52140
agcaggatcg agcgcgatag caatatcgtc gcctggccgg tagcctgcgg cctcgattgc   52200
ttcgacaatg acctcgcagg cctcctcgtt gctccggagc ttcggtgcaa atccaccttc   52260
gtcgccgaca ctggtgctga gaccgcgctt cgacaggata gatttcaggg catgaaacgt   52320
ctcggcccca aaacggaggg cttcagcaaa tgttggcgca ccatgcgggt agagcatgaa   52380
ttcctggaaa tccatgccgg aatcggcgtg catgccgcca ttgagcacgt tcatcatggg   52440
gatgggcaga tggacggccc caacgccacc cagataggcg taaagaggaa ggtcgtggct   52500
tgcggcggcg gccggcaga gcgcctggga aaccccaagg atggcattgg ctccaagctc    52560
ggatttgttc ggcgagccgt cgagttcgat cattgccgcg tcgagcgccg cttgatgtga   52620
aggatcccgt cccttcagaa gaggagcgat ccgctgattg acattgtcga cggctttacg   52680
aacgcccttg ccaccatagc ggctggcgtc accgtcgcgc agttccacgg cctcgttggc   52740
gccagtggag gcgccggagg gaacggacga ggtgccgaca atgccattgt cgagatgaac   52800
gctgacgcga agcgtcggat taccccgcga atcgaggatc tccagggcgg tgatgttttc   52860
gatgaaggct ctcatggact tgctcctgct gccgagatgg cggctttagt gctttccaat   52920
cgggaaatcc ctagattggg cggttggcat cttctatttc tttttctcga tctgatcgaa   52980
acgaccggta ctcccaccga cctgtttgag ggtttcgtcg tcgccatacc tcctccagcc   53040
agaatacgtg atcatcgact ggtataactg gaaaccaggc gtaccactcg cgccacaagc   53100
attgttcctt caccatggcc caatcctccc agttgttatc tcttggtctt aagccctgta   53160
cgcgacgagc acggctcatc ccgcgatcat cacgacaccg agccagttcg gaagtgtcag   53220
gcgttcgccg aggaacagga cggcaaagat ggaaacgaag acaaccgaca acatgtcgat   53280
cggcgcgacg cgggccgcgt cgccaagctt cagcgctcga aaatagcaaa tccaggatgc   53340
gccggtcgcg aggcctgaaa gcacaaggaa taaccagctt ctgctggaga ccgacgacgg   53400
ctcctgccag ttgccggtga tatagaccat catcccagcg gcgagcagaa tgacgatggt   53460
acgaatgaag gtggcgaatt cggagttcga cgccgatctt ggcgaagatc gctgtcagcg   53520
ctgcaaagcc tgctgacatg agagcccaca ggggccagct ggcaaggagg cttttcatgt   53580
cgcttgtcct tgcccaatga gccgtatcaa cgtgagacca gcaaacagtc cagccatcga   53640
aagcaccagc gaagccaagc aagcgtgcgg cggcaatatt gacggcgtgc cgggaaacac   53700
```

```
cacccaaacc cgctccgagg aacacgatca gatagaccaa gaccgtctcc ttcaggatgt    53760
cgtgactttg agtgcttctg ccgccgccac gttgtgatgg acgacgtccc actgttccag    53820
gtgcttgtag acgatcacct tgtttttcag gagcgcgcca tgagtccggc agaattcctc    53880
aagcttgtcg cgcgacgcaa tcatctcgac gcacatggtc agatccggat tggggatttc    53940
gaaaccctcg tcctgaagct tgccgctgtt cgaatatccg aagtgtgtat ggtgagcgac    54000
ggcattcata attcctgctg acttcgcctg caggaccagt tctcgataga gcggcttggc    54060
accaaaccag ctactcttgc ctgaggtctt ctcccgcggt ttcatataga tacgaccat     54120 gccgatttcg gtggaatgca gcctgtgttg cgtcacgatg atgggccttt cggtgagggt    54180
tgcggtggta gcaagggacc ggagccggac cttgccgaca aagtcgccga gcgcattggc    54240
gttcatgtcg cgcatatggc gaaccgagat gtcaggagga atgtcgttgg ccgcagctgt    54300
cttcggcacg cccacgcgct gcgaaaggta gatgctggaa tggccgctgc agaggtaggc    54360
aacgaagcag gcgaccgcga tgtagacgga gtgggttgcc ccgaaaagct cgatgcccat    54420
gatcatgcaa gcgagcggcg tgttggtcgc gcccgcgaag acggcgacga aaccgagagc    54480
ggcaaatagg tccggtggcg caccgagaac gcccgcgaca gcactgccga gagccgcacc    54540
gacgaagaac agcggcgtca cctcaccacc cttgaagcca gcgcttagag tgatgatcgt    54600
gaacagaccc ttccaggccc aactccagta atcgatgtga tctgggcgga agaagccgag    54660
gatcgttgca tcctcgggat tgggggacca taccccaagc cccagatatt ctcgtgttcc    54720
aagggcgtag accaagccaa gcaggatcaa gcttgcgaga accggacgca gcggggcata    54780
gggcaggatg gccttgtagg cggacgatgc caggtgagaa agttctgcga agaaatgcgc    54840
tgccagtcca aaggccacgg aggcaatcac aaccttcagc atcagcacgg cgtcgaggtg    54900
aaagccgatg ccttcaccag cgccgctcag ataggcgatg gcataatgtg tatgcccaat    54960
gctccaggcg tggcaggtcc agtctgcgac aatggcggcc agcaaggcag gaagcaatgc    55020
ctcgtattgc atccggccaa ttgtcaggac ttccaaggca aagaccgcgc cggcaatagg    55080
cgtgccgaag actgcaccaa acccggccgc aatgcctgcc atcaacagga tacgaatgtc    55140
ggcggatgtc agtttaaaga ccttaccgaa ggcgctcgca aggctgccgc ctagctgcac    55200
ggcggttccc tcgcgtccag ctgaaccgcc gaccagatgg gtcagcacgg ttgtgacgag    55260
gatgaacgga gccatgcgca gtggcacgcc gccacccggc tcgtggattt gatcgacgat    55320
cagattgttg ccgccctcgg cggacttgcc aaactttccg taggcccaca ccatagcaaa    55380
gccagccact ggcatacaga agatcagcca aggaaactcg aaccgtagtt ctgtcgcccg    55440
atcaaggctc cagaggaaca gagcaacgag cgatccgacg gctattgcca tcggaatgac    55500
aatggcgatc cactttgcga gactgcggat ttgctgaaaa cgaaggccga ataatgatgc    55560
gagcgtcatg cgaaagacac tccaccaaaa ctgtcagcag atatgagaaa acacagaaaa    55620
tgaattccag acacgaccct actccttcgc gttatgcgcg ttgagtagga gtcatcagct    55680
tcatcgagga agcggttcgg cgtaatgccc ggcagaatcc attaccgttg aggttaaata    55740
ccgttggaaa gtaactagag tcaaggtccc tcatcccgct catcggagtg atcccgtgca    55800
gatagggcaa gacagactgc ggcgatcacc gggacggtga acaggccggc tatcgtgatg    55860
agctgcattt catggcccca actcaaagtc cgcccaaatc gggtagcggt cggaagcgac    55920
gtcggttgtg tcattgctgg cgactgcgta tcccacggcg cgtcagcaag gcgcttgctg    55980
gcaagcaggt agtcggaacg gaaagtcatg aactccgtat tcgtgaaacc gcgtgccggg    56040
acagtcggcg tcggagtggc ttcaaggctg ttaccgacgt ccacgaaacc ggcccgcaac    56100
```

```
aacccggcta tcgtggtcct gtccgctgtg ccgtcctcac gggtgtagcg catacgatat   56160
cgtgcaggca gcaatgccag atcgtcaggc tcaggatcat ccggcgcgac ggaattgaag   56220
tcgccgccaa tcagggtcag tgtggatttc cttgaggatg cctccgtgaa cctgttgatc   56280
ctgcttgcgc ttggatggtc gcttcgcaac cgcgtgcgcg ttggcgtggc tctggctctg   56340
atcttgctcg ttcccggaat cgcgacgttg tggactacct atcagagcct tatggcgccc   56400
gttccgcccc agccgttcct gttggcagtc acaggcacgg gggcgcttgc agtcaacctt   56460
tcctgtgcat ttctgctgac agctttccgt cacgagaacg gtagcctgac gagggccgcg   56520
ttcctttcgg cgcgcaatga cgcgcttgcc aatatagcaa tcatcgtggc cggtatcgtc   56580
acggcctacg cctggcattc cgcctggccg gaccttatcg ttggcctgga gattgccgga   56640
atgaacatgg acgccgcccg cgaggtctgg caagccgctc ggaaggaaca cgccgctgcg   56700
gcttgaagcg attgtcggtg ggtattccaa aggcgaaagc tgcggacgca tgattaccag   56760
gttcacgcat gccgccatac cttcacggca gagatcagca gaatggcggc aagcgccgga   56820
aggagcaagg ccgtcggcac gacaccgagc aactgcccgc caatgaaggc gccagctatc   56880
gagccgagcg ccatgacgat gaggaatgtc ttgttgcgag cgacaacaga gaagctttgg   56940
tcccggctgt agcgcgtaaa gccgaccagc atcgtcggca ggctgacagc aagggagagg   57000
ctgcccgcga gtttaatatc tgcaccgaac agcagcacga gcgttgggat gagaagttcg   57060
ccgccggcaa cgcccaggag cgaggcgact acaccgatta ccagacctgc caaaatgcca   57120
gcgacaatct gcgtcgtgcc agtcacgagg ccagctccgg cggttgcatc gtggccgaac   57180
aacagcacca ctgcgatgac gattagcagc accgcgatca ccttatacag gttttccgat   57240
ctgaggcggg ttgcccagcc cgcgccaaac catgcaccaa gaagacttcc agccagcagg   57300
ttgacgacaa tagtccagtg cgcgacgatc tgatccagtg gaacggtcgc tgcccggaac   57360
ggcaaagcga atgcaacgac aacgaggctc attgctttgt tgaggatgac cgcttcgagt   57420
gccgcgtacc gaaacaggcc gatgagcagc ggcaggcgga actccgctcc acccagaccg   57480
atgaggccgc cgagcgttcc gatcacggca ccccagatga aggctgttgc cgaacgaatc   57540
ttacccgtca tttcttgcct cgtatgggtc ggtgcgctgg tgaaatggtc gcggcacgct   57600
tggtggagtt catgtcaaag ggactgttgg agcgaaagcg ttttcagaga tcgtatgaca   57660
gcgcagcgtt cgatctgcgc tgcgccatcg ttgtaatccg tataaatgtt cacgatattt   57720 gattttgac cgatcgacga tcagacatcc tgagcaggat gtatccgctc actccggcga   57780
tgattgatcc gcctaggatg ccgaacttga cccgatcctg catgacgggg tcctcgaacg   57840
cgagcaggcc aatgaacaag ctcatcgtga acccaattcc gcagagaagg gagacgccca   57900
gtgtctgtcc ccagctggcc gcggcgggca attccgccca tccgcttcga accatgacaa   57960
aaactgttcc gaaaatgccg agcagcttgc caagaacgag accggcacca acacccagcg   58020
ttaatggctc gatcagagtt gctggcgata cacctgcgaa cgaaacgcct gcatttgcaa   58080
agccgaagat cggaacgatg agaaatgcca cgggcttgtg cagaccatgt tccagcttgt   58140
gaagcggcga agccgctggc gttgcctcag gagtgccggg agtaagacgg atggggatcg   58200
ttagtgcgag aagaacgccg gcaagcgttg cgtgaacgcc tgacatcaaa acaagaaccc   58260
acaggaccgc ccccaggacg agaaatggcc aaagccgcat caccccaagg cggttgaaaa   58320
gcaccagatt cccgatcaca agtgcggccc caccaagggc gtacagattg acatcggccg   58380
tataaaacag cgcaatgacg atgaccgcgc ccagatcgtc aatgatggca agcgttgcca   58440
```

```
gaaagattttt cagtgatgcc ggcaccctcg gtcccagcag cgaaagcacc ccgagtgcaa    58500
aggcgatatc ggttgccgac ggaatggccc agccgcgcag ggcggcaggg ttctcgtagt    58560
tgaaggcgat ataaatcagc gccggaacga ccatgccacc ggctgcagcg gctcccggca    58620
gaatgcggcg gctccagctc gagagctggc catcgagcat ttcgcgcttg atctccaggc    58680
ctaccagcag gaaaaagact gccatcagcg cgtcgttgat ccaatgctgt acgctcagcg    58740
gtccaacata gacatgcagg agtgcgaaat attggtcggc aaaaggtgaa tttgccacga    58800
tgatggcgag tagcgcgact gccataagca ccaggccgcc tgatgcctca ttgtcgagga    58860
actgacgaag cgtagagtta atgcgacccc gcaacgggcg ggactgaatt gtggacatag    58920
atctgcgtcc tctgtgcaag agttgttgtt gttctccgta atagggggat ccctggcgca    58980
cgcagcacac gccatagcat tcaatatatt catcaattgt gcagatggcc agcaaaaccg    59040
gtacttcctc ggacagaacc gggatccctg cacctctgca atacgactca gacatctgga    59100
gatttcgtga gcaggtctgc ggcaggaaac ggccgacggg acgggctaac aaggattaga    59160
actgcctttc ggaggtgcga tggtcagcaa gcagcgactt ggatcgcccc acccgcaagc    59220
gaaccaattc cgctctcatg cgatggcgtc ctggcccagg tccgatcttc cacgatcaac    59280
ccgcaagggg tccgctagca ggctgcggcc gctcatggct ttgccatcgc ggtgatcgcg    59340
cccgtccccg tgccttttg gagccatcga gcgggattgg cccgctcccg gatggagcct    59400
tcgaaatgtc gcacgatctt gtcctcgcac agtcccacgc cttccagctt tcccgtgacc    59460
tgatggtccc ggtcaccgtc ttcgaggtcg acggcgaata tggcgtttat ctgaacagtc    59520
aagctgtctc actggcattt cgctgagctc gccggctccc ggaacagcgt ctcgatcagc    59580
ggacattccc gccgattgcc ttctgtgcat tgggccacca cgtccttcag cactcgctcc    59640
atgcgtttca ggtcggcgat cttttcacgc acgtcgtcga gatgcgcggc ggcaacggcg    59700
cttgcctcgg cgcagggctg gtcgcgctcg tcgacgaggc gcagcagttc acggacttca    59760
tcgagggaga agccgagctc gcgcgcccgc aagacgaagc gaagccgtcg ctcgtgggtg    59820
ctgtcgtagc tgcgatagcc gctcgccgtg cgcggcggct ccggcaggag gccgaccttc    59880
tcgtaatagc ggaccgtctc cagattgcac cctgtgcgct gtgcgagttc ggcgcgcttg    59940
aggcctttca cgccagcgtg atcgcgcatc caaaaatacc ccttgaccct gtagttgcta    60000
cagaccgcac attagcgcct ggataggttt tcgacaagaa gagcgaggtc gaacatgaat    60060
gcatcccgac acggaccagc agacgttgca ccgactgcgg caaacctgac gacgccagag    60120
cgaagcgagg ccgggcgaca gcgcctggtc gccgtcggcg gcatactcgg cgccatcgcc    60180
gcctcgtcct gttgcatcat tccgctcgtc ctgttcagcc tcggcatcgg cggcgcctgg    60240
atcggcaatc tgacgcgcgt tgcgccctac aagccactgt tgtcgccgc aacggcgggc    60300 atgctcggct acggcttcta ccttgtctac tggaagccgc gacaggcctg tgccgatggg    60360
gctgcctgca cgcgcgccgt ccccagccgc ctcgttcaga tcgcgctctg gttcgcgacc    60420
gtactcgtcg ccgctgcttt cgccttcgac tacgtcgcgc gctgctgct ttcgcctga    60480 caccaagagg agactacccc atgaggaaga gtttgagcgc tttcactttg atcgcgtcgg    60540
tgatgactgc gcctgccgcc ttcgccgccg aacgcactgt gacgtttgcc gtcgacaaca    60600
tgacctgcgc ctcgtgcccc tacatcgtga agaccacgat ggcggcaatc cccggtgtcg    60660
cgaaggtgac cgtctccttc gaggcgaagt ccgcgaccgt gaccttcgac gacgctaaga    60720
cgagcaccga tgccatcgca gccgccagca tgaatgctgg ttatccggcc cacccgacgc    60780
agcaaggcag ctagatgact gatcgcgccg taatccgcgc aggtgccgtt ggcgccgtcc    60840
```

```
tcgccgcgat ctgctgcgcg gcgccgctcc tcgccgtcgg cctgtctctg gcgggtcttg   60900
gcacgtggct gacaggtgtg ggtgcagtgg tgcttcccct gatcgtcgcg ggcttcggct   60960
tcggcgcgtg ggggcc ccat catcgccggg caagagccac ggcctatgag acgaagattc   61020
gcaaggaagg cgtgaagcca tgaacgattg ctgtgcaacc tcctcccggg acaacccggc   61080
cgtttctcag cccgcgacac tggcgagctt tgccgttcga ccgggcgtaa cgtttccgga   61140
ttggtcggcg gtcacgtcgc ctgtggtcaa aacgctctg caggcgatgg tcgggtccga   61200
ccacgtgctc aatcgctgga gcggttacga tcccgccacc gacagggtgc gtgttgcgtt   61260
gctccgactc tacgccgacc acgggggtgc cccgaccata agcgcgcttg cggagcgtac   61320
aaaactcagt gagatggtca tccggccact gctcgacgag ctccgccggc gcgacctcgt   61380
cgttctcgat ggcgagctga tcgtcggcgc ctatccgttc agcgatcata acaccggcca   61440
tcgggtcact ctggacggac gcacgctgaa tgcaatgtgc gcggtcgacg cgctgggcat   61500
cggtgccatg accgatcgcg acaccgcgat cgcctcgccc tgcggccatt gcggcgcact   61560
gatccggatc accacgcagg accgagggcg ggcactcgcc gacgtcgagc cacagtcggc   61620
cgtcatgtgg cagagcgtcc gttatgaagg cggctgcgcc gcgagctcgc tctgcgcgac   61680 gaccgcttttt ttctgctcgg acgagcatct ttccgcctgg cgcgacgaac gttccaccga   61740
cgagccaggt ttccggctgt cgatcgagga aggactggaa gccggccgtg ctctgttcgg   61800
gccgagcctc gctggtctcg atgtggcgtc gaagagcctg gtggtcgcca accgacccTT   61860
gcgcacaaac ggtcgcaatg gaggcgctta cgatctcgtc gtcatcggcg ccggctcggc   61920
cggcttctcg gcctcgatca cggccgccga tcagggcgca caggtggcgc tcatcggcag   61980
tggcaccatc ggcggcacct gcgtcaatgt cggctgcgtg ccgtcgaaga ccctgatccg   62040
cgcggccgag acgcttcata acgctcgcgt ggcggcacgt tttgccggca ttactgctga   62100
agccgaactg acagactggc gcggaaccgt tcgtcagaag gacacgctcg tgtctgggct   62160
gcgccaggcc aaatacgcgg acctgctccc cgcgtacaat ggtatcgcct atcgcgacgg   62220
gccggctcgc ctcctcgacg gcggtgtcga agttgacggc gcgcgtattg ccgctggcaa   62280
gatcattatc gcaaccggcg cgcggccggc agttcctgct attcctggcc tcgagaccgt   62340
accgtatctc accagtacga cggcgctcga cctcgaggaa ctgccgcgat cgctgctggt   62400
gatcggcggc ggttatatcg gcgcggagct cgcccagatg ttcgcccgtg ccggcgtcaa   62460
ggtgaccctc gtctgccggt cccgactgct ccccgaggcc gagcccgaga tcggcgcggc   62520
gctcacgggg tatttcgagg atgaaggcat caccgttatc tccggcatcg cttaccgcgc   62580
gatccgcaaa accgagggcc gagcgtcact gaccgtcacg cgtgacggtc acgatgtcca   62640
gatcgacgcc gatcaggtgc tgatcaccac gggccgcacg cccaacatcg aaggccttgg   62700
gctggccgag cacgggatca ccgtctcggc gaagggcggc atcgtggtcg acaccgcat   62760 gcgcacgacc aaggctggcg tctatgccgc cggcgacgtc accggccgcg accagttcgt   62820
ctacatggcc gcctatggcg ccaagctcgc cgccaagaac gccctcaatg gcgacagcct   62880
gcgctacgat aacagcgcca tgcccgctat cgtcttcacc gatccgcagg tcgcaagcgt   62940
aggtctcacc gaggcggcgg cgcgtgcggc cgggcatgag atccgcgttt cgacgatcgg   63000
tctcgatcag gtgccgcgcg cactcgccgc ccgcgacact cgtgggctta tcaagctcgt   63060
ggccgatgct gctggcggtc gtttgctcgg cgcccacatc ctcgcgccgg aaggtgccga   63120
cagcattcag accgcggctc tcgcgatccg ccagggtctc accgtcgatg acctcgcgga   63180
```

```
cacgatcttt ccttacctca ccacggtcga ggggctgaag ctcgcagcac tttcgttcgg   63240
caaggacatc gccaaactct cctgctgcgc cgggtgagca caatcggcgt caagggcgtt   63300
tcctgccgat gatcggtatg acgtcggcgg tgcggttatc gcgccgccgt tccataagct   63360
ggcacagcgc gcggacttga cgatgctggg cgagcacggt ttcgacggcg cgccgctcct   63420
gttcggcccg ggccgtcccc gccggccgat ccgtcgcgtt gcgccgggct ctcgactcgg   63480
caactgcatg gcggaaggct tccagcacct cggaagcgcg gttcgcggtc gcgcgactga   63540
cacctgcctc gatggccaga ttcacaaccg tcagcctgcc atcagccacg cggggcacc    63600 cataaaggag gcgcgccatc gcctcacgaa gcgcctgttc cgtggctgca ctgaccggct   63660
tcatgatgtg cgttccttca acggcgcgat gagcctgcgt tttctgtcgt tgtccaggcg   63720
cagcgcttcg cgttgcagcg gggagagacg cttgtcggcg agaagatcct ccgcctgtgc   63780
aatggaggct tcccatggcg ggagatgtcg ctcgacgagg caggcgttgg gacatcggtc   63840
gggcgcgcat cgcgacagga ccggcaccga ggctgaaggt ttctcagact cccgcaggca   63900
gagcgccgtc aatgggtcga agaagcagtc gttcagatat ccgacatgca gcgtgcgcgc   63960
cagatgcgcc agcatcgcct tcaggcgctt gcgatcggcc agttgccccg gaagcgggcc   64020
gagttcgcgc ccgacccgct ccagttccac gccgacgcgc ttaccggcgg gtccgcctgg   64080
accgtgaccg cgtcgatggt tttcgaagta gtcgatgatg tcgtcgagtt gtccgagcgc   64140
cagttcctgt tcgacctcct gcctgaagcc ggatgcggac gagccggcat agccgttgaa   64200
catggccacg gaggcgtgct tgtactggat tttgccggcg acaaccccga agggccggtt   64260
cgcgatgtac caggccagcg ttcgcctgaa ctgacgggtg ttgaagcgcc agacgtcttc   64320
tcccactcgg gggatcacag gactatcgtc cgcgccatat cgctcatcga gatgttctcg   64380
gaattggttg atcttcttgg cgatgagtat cggcgtctcg gcattgttcg tctcgcggtc   64440
gtcaagggca agccatagcc gctctgtccc cgcattccgg cggaatcgtt ccgaaagacg   64500
ctcggcaacc cggatcgcct ggacggcggc ctcgatggtg atccattcga cctgttcgcc   64560
gcgagcgccg cgatccttcc aggtcacgcc ctcgatcgcc agcctttctg ttcgcccgtc   64620
ccggtcgaga ttccgtttca ggcagccgga tcgcagcgac tgcacctcac cgtcgcgcat   64680
gcccgtcaga tagcaacaca cgatataggc ggccgtctgc aggtgccgtt cttcccgcgc   64740
caggctgatg gcatcgaagc gctcccgcca cggtcgcccc gtgtcgggat ccggggagat   64800
cggcgtgtcc atcccgccca cctcgaaccc aagctcgtcg acagcatcat gaaccatcga   64860
caacagggcc ggatctttgt ggacggtggt gagatgcagc ccgcattgca tcgtcaggag   64920
cttcagattg atgacctcgc catcaaacct gccgccccgc gacaatctgc cggtcagccc   64980
cccgatcgaa agaggtcttt ccagacagg aatgcctctt ccttcctcgc gacgcttgtc    65040
gatccaggag gccagcatta ccgcgggccg cgtgtggcgg gcgcgcgagc gtgctgcgaa   65100
ccggctgttc agtgcatcgg cttcagcccg ggcagtgaag atgtcgtcgc agaggtgctc   65160
gacatatttc aaggcccatc gcagcattgc gccgatgacc ggctccggga tgcgcgcggt   65220
ccggttttcc gaacagcgcg ttccctggcc ggttgcccga tagaccggtc ggccgcgcca   65280
cggggtgaag gtgatgccac cgcacgtcag atagggcgcc aggcgatgaa gctgacgat   65340 gggcctgagg cacacaccca cgcgcccggg cgtgatcggc cgcgcccggt gatgggtcgc   65400
gtatgcatcg atcaaatcct gatcgacgtt tgccagatcg agcttgccga tccgcgagcg   65460
cacgaagtcc aggaaccggc gcagcgtcgc aagcgcagta tggccggaga ctggccgcaa   65520
ccgcggctca ccgtcggcgc gccgttcatt catccaggca tagatgtatt ccttcgcaag   65580
```

```
caaccgctct gccgcgcagg ggatcacgcc gaagtcgacc gttcgaaagg cctttctggc    65640
catgttgaac atcgccggcg ccatatccca gacatcatcg ccgaaccgcg agagcgccgc    65700
tcggtcggta ccatccctga gaggcatcga agccaaaacg atgtcgtcat cgaccctgag    65760
gcgtgagacg gcacgctcat cgttcaaagg agaggtagtg gtcatgagcc gtaagcctcc    65820
ggcggaagat agagcaaccg cgccgaggat tctgccgcct caacccgtgc gcctccgacg    65880
acggaggacg ggaacatcgg cagaatttgc tccgtgatcc tgcggtatgg ccgatcgaat    65940
ttctcgttcc agtcgccaga aggcaacgcc tcccgcagct cgtccatgaa cgcctggaac    66000
gcgatcagcg ccggtagttt ccgtgcggta atgaccgcgt tggagcattc caggcacccc    66060
cagaacggcg tcggacaggc ttcgccttcc cgaccgaaag ggctgacgcg aagttgctg    66120 cacgccgcca gccaaagatc ctgctctccg tccaggagcg ggccgatctt ttccgacggg    66180
accggcagcc cggtcgcgtc ggctgaggtt cgcagccggg cttcatccgc gggcacaacg    66240
atccaaggtc gcagagccgg cgccatcgcg tcggtcagtg cctcgactat cgtctgctca    66300
tgcagatgcc gaagggcggg gatgtcggca taatggttgg ccgccaccgc taccgtgtgg    66360
ccgacggcaa agttctccaa ctgccctccg gtccgcttat accagtcagc cttctgggtc    66420
ttgcgcagcc tggagagatt gagcgccagc gattttccgg cgtcatcgac gattccgtac    66480
ttctcgacaa acgcggccac gcaggtcccc agcttttcg gcgacgacag gcgcccggc    66540 ttccaggtga tccagagctt gctcgatcca gtgtgctgcc gagccttttc cgtcagcttg    66600
atcgccagcc gcaggacggc tccgggcgtc tcccgtccgc catcgcggac acgcaagcgc    66660
ttccactggg catgatgcgc gcgccgcttt cgatactcga tctcgacata accccggttg    66720
ggattgcgca agcagtcagc ctcaagccca cgcagcgctt cgatctccat gccggtcgtc    66780
aaggacagcc agacgaggaa gccgacgaca tcgtaccggg tcagtggaa gccggcatgc    66840 agttcctcga ccggaggcgg ctcgagcccc atctatgag cgtggtagcg cagattgtcg    66900
aacagcgcgc cttccccggc gactactccc gccgtcacaa tctgttcgac cactaggtca    66960
tagcgacggc gcaattctgg atcacggcct acatccagaa gtgggggagg cagagcctcg    67020
cccgtcgcta tccggtcgcg agcctcgatg atctggcgca tcgctgcctg cagcaacgtc    67080
gaggcaatcc tcccactgta ggcatcgcgc ggctttgaga cgccgtgctc gccgtgaccg    67140
atgtatttca ggcgcaacag tgtttcgggc ggaagccttt caggattgag ctcggcggcg    67200
acgcgcagca ccccgatcag agcaccgagc acattgcgct gattgggtcg ctcgccgccg    67260
ttctgctcca gccagtcctc ataggcattg attaccgccg gagttaagtc gtcgagacga    67320
cgaggtttta ccgacgcccc ttccaggaac agccagaacc gccgcagacg gcggataaag    67380
gtgcctgcgg ttttccagag tggtgccggc cccatccggt ggagatactc ctgcaggaat    67440
ggcgcaacct catgggtcag cgccgtcagc ggccaggaag acagattgac gtcgatcctc    67500
ccggcatctt ccgtccgaag gacgaagacg agccggatttt gcggatttttc ctcttgagtg    67560 tcgaacaatt cgattccaac tgggaaggtg gcacgacgac cgcgtttcat cacagggtc    67620 caccagcatt aacgcgcagt tcccaggcct cgaccgcagc gtcgatcatt tcctggcttt    67680
cttccatgca atccaggtag atgtgagtgc tttcgatgcg gctatggccc agcaaacgct    67740
gcaacttcag aagaggatcg ccaatcaagc ggcggtacgc cgcgccgata tgggatcggc    67800
gttcgtcgag tacccatccg atctgttcac gcacagagcag cgacagcata tgaaccgcaa    67860
aggtgtggcg catcatgtgc ggagtgacgt cgaggtcgat cccgaaccgc ctgcaccgta    67920
```

```
cgcttgccct ccggaagacc acctcccaag cggccggggg catgggccgc gcccttccg    67980 ccagccaaag acacaatggt tcggatgttt ccgcccatac caagcggctg cgttcgcgcg   68040
gcgccagcac gtcgacactg gctcgaactg tgtccttttc cagaaggagc cttcccgat    68100 cgtggctgac gacacggatc ggatgttcga ttgacctatt gcgcggttgc gaaaggcgca   68160
tgaggacatt ggtccgttcc aacgccgcgt attcatgcag acgcttcagc acgcgctcgg   68220
gcaagcggat ctcgcgcccc ttgctaccct tggcaatggc cggcgccagt cggaaagatc   68280
ggctcctcaa tgcaccgacc ggctccgtcc tcgggaactc gatccagagc agacttgccg   68340
cttcctggag ccgcaggccc gtcgtgacga gcaattcggc gaacaacgca ttgcgctcgc   68400
tgttgcggcc ctgccaggtg ggatcctcgc tcccgtctgg aagacgacca cgcaagccga   68460
tctcgcgaaa caggagatac cgatccaggg aaaggaaccg gatatcgcgt gtccgtgcgc   68520
cgcgctcggt ggcaacattg gcagcgaccg ctatggcccc gccgccgttc gtccgtcgcc   68580
atgattgccg ataggtgaaa ggcgatttgg cgatcattcc ctcttcaaga gcccatcggt   68640
aaagcttgtc gagcgctgct accgaccggt tccagctcgc ggccgagatg cgcgccggag   68700
gaagcgccag acgtcgcgcc gcatggaagg ctgcgacatc gtgccgatca gccgcccaga   68760
gggctctgtt gtctcggcgc tcggcaagaa agcgcatcca gatcaggata tcccaaccat   68820
aggcgcgcaa gctgttgggc gaacgaaccc ccaacgtggg gcaagctcga agaaccggt    68880 tcaggtcgtg atcgtagctg tcgtcatcgc caagaatgaa cggcatgccg tccacgaggt   68940
tcagcttctc ggcggctgcg acttcatcca ccgacagcct gtggacgacg ccatcaaccg   69000
taacagactg ccgcagcgtc gaaagatccg tgaagaagag ctggggcatc ctgttctcct   69060
cggccgcgat tttccgcccg ggacgggctc gagcccgtcc cggcgggaaa atcgcatcgc   69120
ctcacctcaa gcgaagggga atgtcgtcaa cgttgatcgt gtgctgcgaa cgtcacagcg   69180
gtaagacaga acacagagtc aggataatgg cgtccttccc tctgacgaga tcgacgaggc   69240
gacgacctcg aggtcattca tgaatttat ccctgggcgg ctcattgagc cgctttgccg    69300
ttccggctga cgctggcgag cggcatgccg caagggacgc ttcgccatgg ccggtgcaaa   69360
tttgcacctt gcaggccatg cccttgcggc ttttgctctt cgcgtccgtc agaagctggc   69420
ccgcaaaatg cgggaaggaa agcaatgata aattagccgc cacgcggccg gagaagaaaa   69480
tgaagagaga cgagatcgag cgactccggg atacagtggg ttgtcaagcg gtattggaaa   69540
aggctgggtt tgcccttgat ggcaaggaaa gtaccaagcg agcgatgaag tatcgccgcg   69600
gtagcgagat cattatcgtc acccatgccg gccgggatg gtttgatcct ctcagtgacg    69660
ccaagggcga tatcttcggt ttggtgacca ccctggaggg ctgtaatttc ccggagggat   69720
gtatgcgggt cgccgagcta tcgggggttgc ggccatctga tcttgtctgg aacaaggaca   69780
ccgtcgagac gatcagccta gtctcgactg ctgaagattg ggcgcgccga cgatcgcctt   69840
cggccggttc tgccagctgg cgttatcttc gatggcaaag gtcactcccc gcatttgtca   69900
tccgggcggc gatcaaccgc aatctgctgc gcgaggggcc ttacggtagc atttgggcag   69960
cccatactga tcaccatgga aaagtgagcg gttgggaggg gcgtgggccc gattggcgcg   70020
gcttcgcgaa gggtggcgcc aagatcctgt ttcggctcgg cgctgaccac gccactcgat   70080
tgtgtgtcac cgaggctgct atcgatgcga tgagtttggc cgcaattgag ggaatgcgcg   70140
acggaacgct gtatctcagc acaggcggtg gctgggcgcc agccaccgca gccgcactgc   70200
gccggcttgg tcagcggccc gacatacagc ttgtggcagc aacagacggc aattctcaag   70260
gtgatgtttt tgctgatcgg ctgcgcatcc tcgccgagga tctcggctgt tcgtggcttc   70320
```

```
gcctgcgtcc ccacgccgac gactggaatg aggttttgaa gcaaatggag aaggaaaaga   70380
cccaaagaag ggtggaaaaa ggaggcgtgc cgcctgcacg cccgccgcat caagggaggc   70440
ttcgcccggc tgcaccggcc cttgacccgg ccgacgggca ggccggcgtt ccggaaggtg   70500
tcaaggagga ctgaagagga aggcgaggtc gtgaggatct cggcacttcg gtccggcaaa   70560
cccgaaggaa cagccaatgt ccaaccatac cataattcga aagatctttg aggggcgtgc   70620
gacccgtcag cagatgttct cgcttttcga tcgccatgcc aagcgaccca cgcggggcca   70680
cgatgaacca gcagcgctct acgccggtga gtggttcgaa atttcggaag ccgaacacga   70740
ctacatgttc gagatcctgc cgccgctgtg gatctgcggc tctacgttcg ccatgcgcga   70800
attcatgacg ggttcggtaa cctcggtgtt ctttgccctc aggatcgatg ggctgatccg   70860
ttacttccac ggttactgcg atcttttcga cagctcgaac gtcgaagcga tgagactggc   70920
catcatcgag cgcgaaagcc gacccgtccg aacaatcacg cgcgatgaac gtcttgagca   70980
tatctggagc atcacggcgg acgcctaccg cggctatgcc ggcgatcgct ggccgcctgc   71040
agcgcgaggg cagcgcaccg tcatgctctg gtgcacggct aagggaacga cgctgaagct   71100
gctcaccgat ttgaccgaag acgaggtagc ggccaagctc ccggttcagt tccgttatct   71160
ccccgacgcc attgcggctt gagggaggat gagatgcttt cgttcccgct cgaaaaagta   71220
cgcgaggttc tcgatcgcgg tcgggtcgac gctgaggcaa atggcggctt cgcaattta   71280 catcacgggc tcctgcccgg cgaaagtgaa cagccaggcc tctgacttgt cggagataac   71340
ggcgtctatc tgatgtcgaa ctgcaagctg cccgagggta tcaggccgct cgtgatctac   71400
gccgaagagt gcgacccaaa cacaaatgaa gactggtttc acgtcaagcg cgccacgttc   71460
ggcggcgatg atggtgttga gttttttaat ggtgcttctc tggaggccat gatgccgcc   71520 agtcctaccg caagccacct ctcgatcgtt ttccacgacg acgcgatgca cttgtcgctc   71580
atcacgccgc agtaggcacc gtcggccgct caagccaaac ccaaaatcgc ctctctcagc   71640
acggtcaagc cggcgctcac gcaccgtcga tgtcgtgcgc tggcaccaca aggagaaacc   71700
ccatgagtaa taacctttt cactcgatcg gcctgatacc ctcgacatgt ttggcagttc   71760
tgccctctca tccggactaa gcattggcat ccccatttgt ggaggcttcg agccggttgc   71820
cgctaacgat gacgatcccg atccgacacc tccctctcct cccttaatgc cttctccaaa   71880
acgcgcgata gccaaagcgt cgcgaccggc ccttccaagc cagatggaac gggcaaactt   71940
ctatctcgat ggcgatgatc gtcgtcttgc tacgacgtgg aaggagcgcg cgctcaccaa   72000
tgtcgccgcc attctgaccg caaatgagat tgagcgaaac gacgtaccca tcacgcgcga   72060
gcaccagaaa gtgctgatcc gctttaccgg cttcggcgcc ggcgagctcg ccaatggcat   72120
gttccgtcgg ccgggcgagg tcgatttccg caaaggctgg gacgatattg gttcttcgct   72180
cgagcgcgcg gtttgcgaga gcgattacgc gtcgcttgcc cgctgcaccc aatatgcgca   72240
tttcacgccg gagttcatta tccgcgcaat ctgggctggg gtccggaaac tgggctggcg   72300
cggcggccgg gtgctcgaac cgggtatcgg cacggggctg ttccctgccc tgatgccgca   72360
accctatcgc gacgccgcct atgtgaccgg gatcgagctc gatccggtca ccgcccgcat   72420
cgcccgcctg cttcagccga aggcgcggat catcaatggc gattttgccc gcacggatct   72480
ggcaccgatc tacgatctcg ccatcggcaa tccacccttc tccgatcgca ccgtccgctc   72540
ggaccgcgct taccggtcgc ttggcctcg tttgcacgac tatttcatcg ctcggtcgat   72600
tgacatgctg aagcccggcg cgctcgccgc cttcgtcacc tcacatggca ccatggacaa   72660
```

```
ggccgatacc acggcacgcg agcatatcgc caagtcggcc gacttgatcg gggcaatccg   72720
gttgcccgaa ggcagctttc gccgtgacgc cggcacggat gtcgttgtcg acatcctctt   72780
cttccgcaag cgcaagcccg agagccgga gggaaatcag ctgtggctcg atatcgatga   72840
aatcaggccg gccaccgagg acgaaggcgc catcagggtc aatcgctggt ttggtcggca   72900
tccggacttc gtgctcggca cacacgccct gacctccggc ccgttcggcg agacctacac   72960
atgccggccc cgcgatgacg aggatctcga cgccgccctc gccgctgcaa tcgatctatt   73020
gccggccgat ctctatgacg gcgagccgac accgatcgat attgatctgg aggaagaact   73080
cggcgagatc gtcgatctgc agccgagagg cggctccgtt cgcgagggca gcttcttcct   73140
cgaccggtcg aagggcctga tgcagatgct cgacggctcg gccgtgccgg tcaccgtccg   73200
caaaggtcgc acgggtaatg gggtcccgga aaagcacgtc cggatcgtct caaagctgat   73260
cctgatccgc gatgcagtgc gcgaggtcct gaaggcgcag gaagccgatc ggccatggcg   73320
cgatctccag gtgcgattgc gcatcgcctg gtcgagtttt gtgcgcgatt tcgggccgat   73380
caaccacaca gtcgtttccg ttcaagagga tatcgagacc ggcgaggtca aggaaacgca   73440
tcgccaaccg aacctcgcac cgttccgcga cgatcccgat tgctggctgg tcgcctcgat   73500
cgaggactac gatctggaga cggacacggc gaaaccgggg ccgattttt ccgaacgcgt   73560 gattgctccg ccggccgccc cgacgattac ctcacctgcc gatgcgctcg ccgtcgtgct   73620
gaatgaacga ggcacgtcg atatcgacca tgtcgcggac tgttgcaca gcgatccggc   73680 tgatgtggtc gacgagctgg gcgaggccat cttccgcgat ccggccgatg gatcgtggaa   73740
gacggcggac ggatatctct caggggccgt ccgcacaaag ctcgccgccg cgcaggcagc   73800
ggtcgagctc gaccccgcct atgagcgcaa tgtccgcgcc ctccaggagg tccagccggc   73860
tgatctccgg ccatccgaca tcacagcccg cctcggcgca ccttggatcc cggccgcga   73920 tgtcgtcgcc ttcgtcaggc aaaagatgga ggcggaaatc cgcatctacc acatgccgga   73980
gcttggttcc tggacggtgg acgcacggca gttcggttac agcgccgctg gcacatcgga   74040
atggggaacg agccgccgcc acgccggcga cctgctgtct gacgcgctga atagccgggt   74100
ccctcagatc ttcgacgtgt tcaaggatgc ggacggcgag cgccgggtcc tcaatgtcgt   74160
tgacaccgaa gccgcgcgcg acaagctcca aaggatcaag caggcattcc aggactgggt   74220
ctggaccgat ccggatcgaa ccgaccggct ggcccgcgat tacaatgacc gtttcaacaa   74280
catcgcgccg aggaaattcg acggctccca cctgagactc cctggcgcct ctggcgcctt   74340
tattttgtat gggcaccaga aacgcggcat ctggcggatc atcgccgatg gctcgaccta   74400
tcttgcccat gccgtcggcg ccggtaagac gatgaccatg gcggcagcca tcatggagca   74460
gcgccggctt ggcctgatcg ccaaggcgat gctggtcgtg cccggccatt gccttgcgca   74520
ggcggcgcgc gagtttctag gactctatcc aaatgcccgc attctcgttg ccgacgagac   74580
caacttcacc aaagacaagc gtgcccggtt tctgtctcgt gcggcgactg caacgtggga   74640
tgcgatcatc atcacgcatt cggcgttccg tttcatcgcc gtgccctcaa ccttcgagca   74700
acagatgatt caggacgagt tgcagctcta tgaggatctg ctgaccaagg tcgacagcga   74760
ggaccgcgtt tcgcgcaagc gcctcgaacg gctgaaggaa ggtcttcagg agcggctcga   74820
aggcttggcg acccgcaagg acgaccttct gaccatctcc gaaatgggcg tcgatcagat   74880
cgtcgtcgac gaggcacagg agttccgcaa gctgtccttc gccaccaaca tgtcgacgct   74940
aaagggcatc gatccgaacg gctcgcagcg cgcctgggat ctctatgtca aatcccgcta   75000
cgtcgaaacg aagaaccccg gccgctcact ggtgctcgct tccggcacgc cgataacgaa   75060
```

```
tacgctcggc gaaatgtttt cgatccagcg cctgctcggc catgctgcgc ttgccgaacg    75120
cggattgcac gagttcgacg cctgggcctc ctgcttcggc gacacgacca ccgaactcga    75180
aatccagcct tcgggcaaat acaagccggt cagccgcttt gcgtcgttcg tgaacgtgcc    75240
ggagctgatc gccatgttcc gctcgtttgc cgatgtggtg atgccggatg acctgccggca   75300 atacgtgaag gtgcccaaca tctcgaccgg ccggcggcag atcatgacgg ccaagccgac    75360
ggcactgttc aagacctatc agcagaccct cggcagcagg atcaaggcga tcgagcagcg    75420
cgagggtccc gccaagcccg gcgacgacat cctgctgtcc gtcatcactg atgggcgcca    75480
tgcggcgatc gacctgcgcc tcgtcatgcc ggcggctgaa acgaggaga caacaagct     75540 caatctgctc gtccgcaatg cctacgggat ctggaaggat accggcgagg cgatctatcg    75600
acgccccgac ggcaaagact tcgatctacc aggggctgcc cagatgatct tctccgatct    75660
cggcacgatc aatgtcgaaa agtcccgcgg cttctcggcc taccgcttca tccgcgacga    75720
gctgatccgg cttggggtgc cgggatcgca aatcgccttc atgcaggact acaagaagac    75780
cgaagccaag cagcgactgt tcggcgatgt cagggccggc aaggttcgtt tcctgatagg    75840
ctcgtctgaa acgatgggca cgggcgtgaa cgctcaagcg cggctgaagg cgctccatca    75900
cctcgatgtg ccatggctgc cgtcgcagat cgaacagcga gaaggccgga tcgtccgtca    75960
gggcaaccag cacgaagagg tcgatatctt cgcttatgcc acagagggtt cgctcgatgc    76020
cagcatgtgg caaaacaacg agcgtaaagc ccggttcatt gccgcggccc tgtcgggaga    76080
tacctcgatc aggcggctcg aagacgttgg cgaaggggcg ccaaccagt ttgccatggc    76140 caaggcgatc gcatccggtg atgaacggtt gatgcagaag gcaggcttgg aggccgatat    76200
cgcacggctc gagcggctgc gggccgccca cgaggacgat caatatgccg tccgtcggca    76260
gatgcgcgat gcagagcgcg aaatcgaggt ctcagcccgg cggatcgccg aaatcggcca    76320
ggacatcgcg cggcttcagt cgaccaccgg cgacgccttc acgatgacgg ttctaggtaa    76380
agaacatgcc gagcgcaagg aggccggccg ggcgttgatg aaggagatac tcacactgct    76440
gcagctccag caggagggtg aagttcatct ggcgacgatc ggcggcttca atctcgttta    76500
tgatggtgag cggttcggca agggcgacgg ctatcgctac gagacgctgc ttcggcgtac    76560
cggtgcggac tacgagatcg atctggcgat cacggtgacg ccgctgggcg caatctcacg    76620
gctggagcat ggactcggcg gcttcgagga ggaacagcgt cagtatcgct ggcggctcga    76680
cgaggccgag cgccggctga gttcgtatca gtcgcgcatc ggcggcgctt tccagttcgg    76740
cgatgagctc ggcgccaaga agaagcaact tcgcgagatc gaggaagaac tggctgcatc    76800
cgccatcgca ggcttttgc ctgggctcca ttccagtcgt ggcatcgacg aaggatcgcg    76860
ggtagagact tgtaatttct cgacctcatc catgtctgat gatcacttcc cgttcagatg    76920
atgtcctgca aatggcgctt ggcaatggct ttcggagtcg tccgggttag acaaagggcg    76980
ctcccttcgc gggtcgagcg cccttttttgc gttttcgttt cctggcaagg tcctgcgtgc    77040
cattcgcgcc gcagcgtgcg cgggccagcc cttcaataga ggaatggagg agaaggagga    77100
gggaaagaac cgattgctga tcgatcctcc tgccgacgca gctgctcaac cgccacctgc    77160
gccatcccgg ctactcgtcc ttcgcagggc tgtcagcccc gcttgttctt cgcagcaggg    77220
atgctcggtc gcagttgcgt cagtccggcc gatcagcggt ccgggagatg tcttcgagaa    77280
aaatgaagac aggaagggcc ggcatggcgc cggtccggaa ctctctagac aaggacaaat    77340
cccatgcaaa tcatcaaggt tgacccgcgc gcgttgaagg aaaaccccga ccggatgcgc    77400
```

```
cagtcgaagt cgtcgccgca ggccgatgcg ctgatgctgg ccacgatcaa ggccgtcggc    77460
atcgttcagc cgccggtggt cgcaccggaa acggatggcg gaaatggtta tatcattgac    77520
gccggccatc gccgtgtgcg ccttgccatc gccgcaggcc tcgaagaaat cgaaatcctc    77580
gtcgttgatg cagccaacga caacggcgcg atgcgttcca tggtcgagaa cagcgttcgc    77640
gaagcgctca atccggtaga ccaatggcga ggtgttgaac gccttgttgc actaggctgg    77700
acagaggaag cgatcgccgt cgctcttgct cttcccgtcc gccagatccg caagctgcgc    77760
ctgcttgcca atgtcctgcc agctatgctg gagcagatgg cgctgggcga catgccgtcc    77820
gagcagcagc tacgggtgat cgcggccgcg ggccaagtcg atcagaaaga agtctggaag    77880
gcgcacaagc caaagaaggg tgatacggcg ccatggtggc agatcgccaa tgcgctgacg    77940
aaaaagcgca tgtatgccag ggacgcgagc ttcggtgacg atctggctca ggcctacggc    78000
atcgaatggg tggaggatct cttcgcaccg gccgacgagg acggccgcta caccaccaat    78060
gtcgaaggtt ttcttggcgc ccagcacgaa tggatgacga caatctgcc gaaacgcggc    78120 gcgatcgtcg aggtcaacag ctggggccag ccggaactgc cgaaaaaggg atcccaagtt    78180
tacggcaagc cgtccaagtc cgaccatacg gcgctctacc tcgatcgtga cggcaaggtc    78240
cagaccgtgc attaccgcat gcccgaggcg gcgaagccga agggtgctgt tggcgacgga    78300
tcggtcactg gcggcgatga caccgacgca gtcgccacgc cgaaagcccg gcccgacgtc    78360
acgcagaagg gccacgacat gatcggcgat ttccgcactg atgccctgca cgatgcgctc    78420
ggtcgcgcgc cgatcgagga tgatatgctg atggcgctga tggtcctggc gttcgccggc    78480
cagaatgtcc gcatcgactc cggcgcagat ggcaccttgt acggcggcaa gcgcttctcg    78540
cgtcatgccg tcggactgtt tgacgagcat ggcaagctcg ccttcgatca ggacacgctt    78600
cggatcgccg cccgctcggt gctgatcgac gtcctctcgt gccggcgggg catgtcgaac    78660
agcggcatgg tcgcgcgctt cgccggcgag gctattggcg ccgacgcttt cctgccaaac    78720
atgggctcaa aggacttcct cttgtgcttg tcgcgtcagg cactggaagc ctcttgcgcc    78780
gaggcatcgg tccagccgcg cccgaaggtc cgcgaaaccc gcgcggcact cgtcgagcat    78840
ttcgcgtacg aacacttcgt gcatgcgtcg gcccgcttcg caccgcctgc cgacgagttg    78900
ctcgagtgga tccgggcagg cgcggacacg ggtggcatcg gcgccacgcc ccaggatgaa    78960
ggggaaagcc gtaccgatga tccatcggta gatcagccag aacacaatac cgacgatgtg    79020
gtcgaaggcg aaactgagga tgcggatctg cccgaccatg atgtgcatga cgaagacgtc    79080
gatcagaggg ttgcagcatg accgccgcct tccagtcgaa catgacacca cccacccccg    79140
atcatttggg ggtggagttt gccaccactg cggacggcct gcccgtggcc cgcatcggtg    79200
acctggtcct tgccatggtc acatcacaga gcggctttgc ttttattgca agcgcccgtg    79260
cgatccgtcg gccactcgca gatctgacgc gcgccgactt catcgggcat gacggccggg    79320
tggcggatga agcagagttc cgggcccgtg tcgccgagac cgctggtcac aaacgcgatc    79380
tggccaaact gaaccgcatg caaacccgca tttcggccag cacaccatgg ggcggatcgc    79440
agagagcggt cgtgtacgcc gagggcgtcg tcgcccacat gacatcaggg catgggggct    79500
tccatctgtc gacagagcgc aatgccaagg tccatccgct gctgcggaag gatatgccct    79560
ggtacgagga agactgcgaa tgggcgatcg tagcgatctg cttttcggac ctgttcacca    79620
cctatgagcg gtcgatggct gagaagaccg tccgcaatac ttggcccgac gcctgggaga    79680
aaatccatgg gcgtgcgctc gccgagggcg agagctgggc caaggatcgc cgggcgttcg    79740
atcagcgtca tgccgtcgac ttcatagtca cgtcggcaat cttgtccgat cagcgccccg    79800
```

```
gcatgacgga ggtcgtggcg aagatcggcg gaggccatat ccgcggtggc gaagaacgcc   79860
gatttctggt ggcaagcgac gaatatgcgg ggcggggggcg gttcggcttc gtcatcgatc   79920
tcgcgcgcca cgctgaatat gatggcccct cctccttcat tggctggaga accggggggg   79980
atgggtcatg atcgacatcc gcctattgag gccgctggcg aaagcaatcg gcgcccggcg   80040
cgagacccag cggcatctcg attgtctgac tcgccagatt gcggcgcgcg ccgcaagaca   80100
ggcgaccaca gtgaaggtcc ggagccgcgc gcggcaccgg tccagtcccc gtctctacca   80160
tcgggagatc gtcgaccgcc ttgccttcga gcgctgggtc gaactcgaca tgatcgcctg   80220
caggctggcg atgcaggagc aggtcatcgg ggcgttcctg catcgcgacc gcgagcctgt   80280
gctgcatccg gcgatatagg aggacccgaa gcgaaaggac ctggcgatgt cctacccggc   80340
tgcgatgtca tcgtcatggt gggcttggcc atgtctgtcg cttgccttgg gattgatatc   80400
ggacccgtgg cggactgccc ttcttgttcg ctgcggtctg aaccggcggc cggtcgtttc   80460
aaggccgctt gcgcgccgcg gggcggccga tccagcctct ctgcgcgagg gcaggctcgc   80520
ggtctgctca ggtcaagacc tgctggcccg caaccctacc ctgctggctc agccagatcg   80580
gacctgtgaa gccacccgtc ccttgccggt tcctggtcgt ccgcatcgaa gggcagaccg   80640
gcacgggccg gaaccgcttc gcaagccaag gaaggaacag acatggccaa gccctctacc   80700
cccaatcgct ccaacaccag gtcgtcgcaa tcccgcaaag gtgcaaccct cgaaatggtc   80760
cgcctcacat gccccgacgc cacccaggcg tccaagatcg cgacaagctt cggcacggca   80820
gtcgtcgaca gcgatggcat ccgcagcctt cacgagcggc tgatcgtcga gaccgccgaa   80880
agtctgtccg aaggcctcgg cgagaaggcg atgcagatcc acctccagcg catcgtcggg   80940
tcctttgtcg gatccgcgca tggcgccggg caattctact cccgcgccgt cacagaggcg   81000
cgcgacgcaa cggccaaggc gtccaacgat gcccgtgacg aggatctcga tggtccggtc   81060
ggctatgaca gcgccgccca gcgcaagcgg gagttcgcgg ccgacatggg tgtccaatcg   81120
cacgccctgc gcatggcagc cgagggcgca gtcgcggctt acgaacaggt catcggcgag   81180
acctggaagc ccttcgaccg gccggtcgaa aatccgggcg catcactcga ccgcaaagca   81240
gccgaagctc agttggccgc tttcggataa cacattggcg gggtcgcacc ccgcccttttc   81300 ttcatgttcc gaggcaggcc ctcgcagggg cccgcctttt ctcatgtcaa aaatgaaagc   81360
tgggtgcgcg cctatcgcgg cccgtcccgc tcggcggtcc tgcaggagcc gggcacccat   81420
gcaacggctt tgccgtcctc cacgctgttg cggccgttcc ggtgcatggc cgcaccatcg   81480
cccctgactt cggacctccg tgacggaccg cgacaggcgc ggtcttcaag aaaaggagaa   81540
ggaagtcatg ccaggaaaaa cggataaaga tcgcatcgat atctacaccc ggatcacaga   81600
tcggatcatt gaggatctcg aacagggcgt gcgtccctgg atgaaaccat ggagcgctgc   81660
caacaccggt ggccggatca cccggcccgt gcgacacaac ggcctcccct attccggcat   81720
gaacgtggtc ctcctgtggt cggagcaggt atcgcgggc ttcgcgtcgt cgatgtggat   81780
gacgttcaag caatccctcg aactgggcgg ggccgtgcgc aagggcgaga ccggctcgac   81840
cgtcgtcttc gccagccgct tcaccaagtc cgaagcggac gggaatggca acgaggttga   81900
tcgggagatc ccgttcctga aggcctattc ggtgttcaac gtcgagcagg tcgacggtct   81960
gccccaaagc tattatgcgc cgccggccaa ggtcgttgat ccgatcgcgc ggctcgagag   82020
cgtcgatcgc ttttttccgca ataccggcgc agtcatccgt cacggggca accaagccta   82080 ctactccccg gtcatggact atatccagat gccgcccttt gagtcgtttc gcgatgcagg   82140
```

```
cggatacgcg gctgtgctca gccatgaggc gacccactgg acggcggcgg agaatcgggt    82200
gggacgtgac ctatcgcgct atgcaaagga ccggaccgag cgggcacggg aagaactcat    82260
tgcagaactc ggcagttgct tcctctgcgc cgatcttggc atcgcaccgg agctcgaacc    82320
gcggccggat catgcatcct atctgcagtc gtggctctcg gtgctggcca acgacaggcg    82380
ggctatcttc caggcggcgg ctcatgcgca gcgcgctgtg aatttcctgc attccttgca    82440
gccggaagtg gatgtgaagg ctgcggcctg acgctcaggc gcggtcgtta ccaccggtgg    82500
cggccgcgtg attttcatca tgttggtcct tgagaccctg cgcaatgtca gcatccagcc    82560
ttccccagat cgacggtttc tgagcgtcgg atttgggttt acgggatggt ttgcgctcaa    82620
tgatgaacgg cttggtctgc tgacgcattg atcctccagg cagcgatttg cgagcgcaac    82680
gatatcgcaa tgggcgcagt cagcaagcgg gccagtgttg acaggcacgg cttgtccccc    82740
gattgaggca gtgcagcacc ggtctgaggg ggcgtagcgc aggatgccat tcgtgcccat    82800
ggcgaatgcg gcggaacgcc attgccatat cccttcacgt cagagtttcc ggcaacccat    82860
ctgcgggctc gataaggcat gtctgaccgg agaccggctg cgcctcaatc gttttcccgc    82920
aacggcaagc cgtaaatttc ttaccccgga gcccacctac cccactcgac aagtcgagcg    82980 gggacccag ctcggctcct cctctcccac taacaaatct gcgacttgcc gccctccatt    83040
tcattccggc cttatcaggt gcggtccgat catcaccggt cctttgacag ctatcgaggt    83100
cgcgatgggc gcggcccgaa catgagaaaa ggaatacgac aatggcaacc atcggcacat    83160
tcacctccac cgaaaacggc ttcaccggct ccatccgcac gctcgccctc aacgtcaagg    83220
cccgcatcgc ccgggtcgaa accccctccg acaagggccc gcagttccgc gtctacgctg    83280
gcagcgtcga gctgggcgcc gcctggcaga aaacctcaga acagggccgc gactacctct    83340
cggtcaagct cgacgatccg agcttcccgg ctcctatcta cgcaacgctc gccgaagttg    83400
aaggcgagga tggcctccag ctcatctggt cccgcccgaa ccgggactga ttgacatcac    83460
ggggctccgc cgccggcgga gccttctcct ctgccgagaa ctcaaagcag taccctgcat    83520
cgagccaggt cctgcttttt tggtggcata ccgagacggg ggatatgctg ctcagatcgg    83580
gcgagggtgc cgggccggaa tgacggcgtc aaggacgagc ggttccccca atttcgcgcg    83640
aacgctcttt gagcgcccgc acgaaatcgg ctcccccact cgccgccgct ggcggtcgca    83700
tccgcgatcc ctgaccccgc catcccgccc gccctgcga tgtcgtcttt cacaaactca    83760
aggagatggg acgatgacga tcgaacagca catcgaagaa ctgcgcgccg agctcaagaa    83820
cgcatgcgac gctgcggagc gcggcgagat ccagaccgag ctggacctgg ctcaagcgga    83880
gttggcaatc atcacggcag agcaggacgg aagcgttgat gccgagccgc ccttctgagg    83940
gcggtagacg acacagccag gcgtggtctc tgtgtaaggt gtcgaaaggc cgagacattg    84000
caccgcgtcc ttgtcgagct aggccatcga catcagggat gttgcagtcc ggtcgtcggg    84060
cagcaactca tcgccatcag aattttcccc gccgcttcgc gtctcctcgc gcgccaaaat    84120
tcaggtgtcg ataagtcctc cgcttcgctg cggccgtacc gatgcaatcc tccttgtccc    84180
ggcctgcggc cgatccctgc gatgtccgca atcgacaagg agaaaccacc atgcaacgcc    84240
tcgcgcaatt cctggccgcc acaggccgca agctttcttc ccttggcaag gtgatcggtc    84300
acattttccg caagggcaaa ctcggcctga agctcgcgat caagatcccg ttcttcgtcg    84360
agatcgagat ctccttttgaa acagattgga gcaggcgccg ataacggcgt tgtgcaacgg    84420
ccagcaatcg tgggccggtt tcagcaccag ggctgtctac ggcccgtcca ggttctggcc    84480
aggccttccg atacgaggat atcgccgaga ctcctgccgt cacggatgag gacgcggagc    84540
```

```
ttgcgaccgt atctgtcttc gtcgcgtccg ggccatgcgc gaagcttgaa ggaccoctga   84600
ttgaccagtt cgatcaggcg atcggtcgct cgatttccaa gcgccagctc cgttgcgcat   84660
ttcggctcac tgatctcggg agcatcgata tcggcaattc ggattttgc gccctcaatc    84720
cagagagtat ctccgtccac gacgcaggcg aagcgatcac caccataaca tttccggtat   84780
gtcgtctctg gactgatgac cgagctcgca gcctcggcga ctggagtgag cccaaatatg   84840
tgagagccca gcgcgcagcc ggatactgcg atcgcgacga tgatccttct cacggggtaa   84900
cggacctctg gcagaccgct atggtcgctt ctctacaatt ccatggctct caatttcaat   84960
gcgatccgtc agagatggtt ttcatatcgc tcttcggtgc agctggcgca aacgccactg   85020
cgagctttcc cgatcacgta tgttgcgccg agttgattgt acggtatccc cggtggcgtt   85080
tttgcctgac gagatcaagg aacaattcaa ccgcgtcttt ctcttgctcg aagtgatgaa   85140
gctttagctg gcctctggtg ccgatgcgtc cccaacgccg cataagacag gcctctccga   85200
agagggtcgg ctcgatcgat atggcataga agcgtgccat attcttctca gcatccgtgc   85260
gttcgatata gaggtgatag ggctgggcga tcatggtgag aggatcgcgc aatcgggcct   85320
atgcgtccaa cgacagttgt gaatcgatgg tcggggaatg attcagtttt gtgaagtatg   85380
gacagacgga gcaccgggcg gtccgccttt ggcgtacggc tctattcgct ggagcgaacg   85440
aagccgagct gtggtcttcg ccgatcccgg taacgatcct cccgcgatag ccgactgcca   85500
ttgatcagta tcccaggtaa ccgagaatat cggcgccaca atagtcggct tgctcgtctg   85560
gatgaacgat gagatcaccg gtcgtgacat ccaccaaagc gctatcgctt tcgcgaacga   85620
tggcctcaat ttgatggacg cggcattctt cgatggcctc ttctaccgtg acctgtgcct   85680
cgcaggcttc ccaatatctc atcgcccggt tctggatttt gggttctccc tcagaccttg   85740
atttccaatg gtccacggtt tccatggaag cggttatcgc caacgcagga cttcatgtcg   85800
gctcgccgga accacatcgc gcgaccgcat cgaagcggcg catttccccc ggtgaacaca   85860
atctgctcat cggcacgcat tcgcaggact tcgtgcggct ggatcaatgg tcggctggca   85920
agttgctttg atcgggttcg tgacgaaccc ctcgcctgaa agctgcggct gacctggtcg   85980
atctcgactg tcgttgttcc acaacgccgg gagatatagt ccgcggtctc cggatcgttg   86040
atcgctgaga aactgatcca gctcgcgctt tcgaaccact tgctggtggc gtcgcgtccg   86100
ccataggttt cgcgcatctg gccgatcgac tgatagatca tgagaagcgt gatcccgtac   86160
tttcggccgg catcgcgtgc cgtctcaagg atcctcatga aacccaggcg agcgacctcg   86220
tcgagaagga agagagcgcg tcccggcatc gccccgtcac gattatagat ggcgttcagg   86280
aatgagccga tgatcacccg cgccagacct ccgtgggttt ccagcgtttt gagatccagt   86340
gcgacgaaca cgtcggtcgt tcccgacgcg atgtcatcgg tcgaaaaggt cgaaccggac   86400
acgagaccgg catagttcgg atagctcagc caatgtgttt cttttgatcgc attggcatag   86460
acaccggaaa atgtctccgg cgtcatgttc acgaacgctg caacgttctc ctttacgaaa   86520
tcggactcgg agttgtcgta gatttcctga agccgcgccc gcagctttgg ctccggttcc   86580
gagaggttca tcggacggt ccgcagcgtc tgattcttct tttccgtatg accggacagg    86640
cagacatcgc cgatgatcgc cgtcagcagc tgcaagccgg acgcccgaaa gaaatcgtcc   86700
cggacgccgc taacgcggcc gctctcgctc atgatccagg aggcgaccgc agcgatatcc   86760
tcttccttcg tcccgccatg ctgaccgatc cagtcgaggg cattaaaccc gatatcggga   86820
tctttcgggt cgagcacgat gacatcacgg ccggccttaa tccgatgcgc cttgaccatc   86880
```

```
ggcgccacct cattggatgg atcaagtacg atcagcgtgc cgccccattt cagcgccgtt    86940
ggaattgtca ccgacgtagt cttgaaaccg ccggagcccg cgaacacgat gccatgcgac    87000
gatccgaacg aaccatcgaa gcagagcagc ggtgacttgc ccccggtgcc ccatgtctca    87060
ggctgatcgg cccgaaacga gagtgccgcc gtgctgtcgc gatcgacacg ataccgctcg    87120
ccgatcacga tgccgccgcc gtctgcgaac agtttctctg cttccggcag tttcatccat    87180
tccgcctcgc catgcagcgc gcgtttaccg cggatgcgtt tcggctcgga acgcgagaat    87240
gcggcgttgc cgatcaccgc gacgcgcagc gcgaacatgc cagagaacag agctgcggca    87300
gcacctgtca ttgttgccgg gtcgacgtag gacaggatcg acctggccgc aggcgcctgt    87360
ccggcaaatt gcgaaagtcg cattccttcc cgaacgacgg caatggcgat gacggcgccc    87420
gatccggcag cgacgcccca ccctgcggtc ttgatgttga ccgatccctg ggcactgagg    87480
agaaagatca gcccgatcgc agcacttgcg atatagggca gcgacagtcc gattcggccg    87540
agggtcaatt tggcctctgc cgttttttccg aaactggcga gccactgttc gatccccggc    87600
aacatcagtg cgatggcgat catcaccagc ggcggaacaa cggcgagcag gatcctattc    87660
gctgtcattg ccgaatgcct ccgcgccgat tgcgatcaga cgggatcgct ccgcctcatc    87720
ggccttgatc ctcgtcttcg cttcgatcaa cagaccgagc aacagcgcgc gttttttcata    87780 gcgcagtcct gccttgacga tcaggccgcc caattcgatc ttctcgcggg catccttctt    87840
tcttgcctct gctgtggtca gccgctgcat ccgctcaagc ctcgccagcc tggcccgcag    87900
ccgcgccagc actgagcgac gttgccgacg atgttccggt cgctccagcg gcactctttt    87960
cttttccgtt cgatccggct ttggttccgc gaaaccgctt cgccacgtcc tcgaacgctg    88020
cctgaaggtc ggcgtcgtcg acttcgatct ctccaagtcc ggccttcagc gcaatgcggc    88080
cgatgcgttc ggcgtcacgc gtttccgctt gcttcagctg ttcttgcagg cgggcaagtt    88140
cttcgcggat tttcgacgtt ggcttcttca tcggaatgca atctccagtc atgtccgtgg    88200
aatgatggga tgagggtccc cgattttttc ccggcaggac aggtacaaat ttgtacctcg    88260
ccaaagcgtc agcatttggc gaatgatccc gccgctcgac aagagcggat ccaagggcgc    88320
aattatacgt cgctgacgcg acgttctgct tttgcccccct ggtggggtca cctcttgcga    88380
tcaacctgtt gatttcgttt gcaagaagga gcgctccacc cgtggccgtc ccgcatttct    88440
cagtcagcat cgtcgcccgt ggctctggcc gcagcgcagt gctgtctgcg gcctaccggc    88500
actgcgccag gatggactac gagcgggaag cacgcacgat cgactacaca ggcaagcagg    88560
gtcttctgca cgaggagttc gtcatccctg ctgatgcgcc agactggctc cgcaccatga    88620
tcgccgatcg ctcggtctcg ggtgcctcgg aggcgttctg gaacaaggtc gaggcgttcg    88680
agaaacgggt cgatgcccaa ctcgccaagg acatcaccat cgcgctgccg atcgagctct    88740
cctccgagca gaacatcgcg ctgatgcaag acttcgttgc cgagcatctt acgacgaagg    88800
gtatggttgc agactgggtc tatcacgatg cacctggcaa cccgcatgtc cacctgatga    88860
cgacattgcg gcctctgagc gaggacgggt tcggtgccaa gaaggtcact gttcgtggat    88920
cagacggcca gcccatgcgc aatgacgccg gcaaaatcat ctatgaactc tgggcgggtg    88980
gcgccgagga cttcaatgcc tttcgtgacg gatggttcgc tgtccagaac cggcacctgg    89040
cgcttgccgg gctggatatc cgcatcgatg gccgatcctt cgaaaagcag ggtatcgagc    89100
tgacacccac aattcatatc ggcgtcggcg cgacagccat cgagcgaaaa tcagaaatgg    89160
aaaaccggct ggcgacagct gggtcacgta agcttgagcg gatcgaattg caggaggagc    89220
ggcgcgcgga gaatgtccgg cgcatccagc gcaatcccgg tattgtgctc gatctgatca    89280
```

-continued

```
cccgggagag aagcgttttc gacaaccagg acgtggcgaa aatcctccat cgctatgtcg    89340
acgacgcggc cctcttccag agtctgatgg cgcggatcat gcagcatctg acgtgctgc    89400 gcctcgattg cgagcggatc aactttacct ctggtgtcag gacgccagcg cggtacacga    89460
cgcgcgagat gatccgcctt gaggccgaga tggcaaaccg gtcgatctgg ctgtcgcagc    89520
gatcatcaca tggcgtccgt cagaagatca tcgaggcggt gttcgagcgc cataagcgcc    89580
tctcggatga gcagaaaacg gccatcgagc acgttgcagg tcaagagcgg attgcagccg    89640
tgatcggccg cgccggcgcc ggcaagacca cgatgatgaa ggcggcgcgc gaggcctggg    89700
aagcggccgc ctatcgtgtc gttggcgccg ccctggcggg aaaggcggcc gaaggattgg    89760
aaaaggaagc gggtattctt tcccgcacat tatcctcctg ggaactccgc tgggcccaag    89820
gtcgcgatca gctcgacgac aagacagtca tggtcctcga cgaagccggc atggtctctt    89880
cgaagcagat ggcactgctt gtcgaagagg caacggtgcg aggggcaaag ctcattctca    89940
tcggtgatcc cgaacagctg cagccgatcg aggcaggtgc cgccttcagg gccatcactg    90000
atcgcatcgg ctacgccgaa ctcgaaacca tctatcgcca gcgcgagcaa tggatgcgcg    90060
acgcgtcact cgatctcgcc cgcggcaaca tcgccaaggc tgtcgagtcc tacagcgcaa    90120
acggtcggat gatgggatcg accttgaagt cacaagctgt cgaaaacctt atttccgatt    90180
ggaaccgcga gtacgatccg gcccattcct cgctgatcct cgcacacctt cgccgcgacg    90240
tgcggatgct caataccctg gcgcgcgcca agctggtcga gcgcggcctt gtcgatgacg    90300
gtcacgcctt caaaaccgaa gatggtgtcc gccatttcgc tgctggagat cggatcgtct    90360
tcctcaagaa tgaaagctcg cttggcgtca agaacggcat gctggccaag gtggtggaag    90420
ccacccgggg gcgtatcgtt gccgaaattg gtgaaggcga acatcgcaaa gctatcagcg    90480
tagagcagcg gttctacaac aatgtcgatc atggatatgc gaccacgatc cataagagtc    90540 aggggcgac cgtcgacagg gtcaaggttc tggcctcgct ctccctcgat cgtcacctga    90600
cctatgtggc gatgacccgt catcgagagg atatcggcgt ctattatggc gcgcgatcct    90660
tcgccaaggc gggcggcctg gccgagcttt tatcgcgtac gaactcaaag gaaacgacgc    90720
tcgactacga gaagggcgcc ttctatcgcg cggcccttcg cttcgccgac gcgcgcggcc    90780
tgcatctggt caatgtcgcg cgcacccctcg ttcgcgaccg cctcgactgg accgttcgcc    90840
agaaacagaa gctctttgat ctcaccgccc gcttggcgac gatccgcgca cagctcggtc    90900
tcaagggccc gaatacccaa gtgacctcga aacccgacat ggaggcaaag ccaatggtat    90960
caggcatcac gacgttcccg aaatcgatcg accatgccgt tgaggatcgc ctagtcgccg    91020
atccgggttt gaagaagcaa tggcaggagg tcacgacacg ctttatccaa gtcttcgccg    91080
agccggagac cgcgttcaag gcggtcaatg tcgatgccat gctgaaagat ccggcaagag    91140
cgcagacaac gcttgcgaag atcgcagctg agccggaaag gtttggagcg ctcaagggca    91200
agaccggcat cttcgccgga gcgaatgaga aggcggcgcg cgacacgcg cttgtcaacg    91260 cgcctgcctt ggcgcgaaac ctcgagcgct atgtgacggc gcgtcgag gcggagcgca    91320 agcatgaagc gcaagagcgg gcaatccgcc tcaaggtctc catcgacatc cctgccctct    91380
cgccatcggc caggcagacg cttgagcgga tccgcgatgc gatcgatcgc aacgatcttt    91440
ctgccggtct cgaatatgcg ctggccgaca gaaacgtgaa agctgagctt gaaggctttg    91500
ccaaggccgt gtccgagcgt ttcggagaac gcagcctgct gccgatctcg gcaaaagatg    91560
caaacggcga gacctttcac aaaataacgg ccgggatgac cccttcgcag aaaagcgaag    91620
```

```
tgaagtcggc ctggaacagc atgcgcactg tgcagcaact cgccgcgcac gagcgcacca    91680
cgctggcatt gaagcaggct gaaacagcgc ggcaaaccca gactaagggg ctttctctga    91740
aatgatattg gcgatgcctg aaagcactgc gatgtctcgt caacgaagct ccgcattgat    91800
tacgttatcg gtggctgccg gcctgctgat cgtcttcttt gcggcgggtc ggattggtgg    91860
tctgcgcgtc aacatgacgc cgagtgagcc gctcggcctc tggcgcatta ttccgctgac    91920
gcgcgcggcc cggtccggcg atacagtttt cgtctgcccg cctgacaatg ccgcatgcg    91980 cgaggcgagg cagcgcggat atctccgccc gggactttgc cccggtgggt tcgcaccgtt    92040
gatcaagaca gtcatcgcgt tggcgggaca gcgcgtggac gtcaccgatc gcatcgccat    92100
tgatggcgta ccgatcgcca gatcccgcat catggagaag gacggacagg ggcgatctct    92160
acggcacgat caaagcgaaa tggtgcggcc cggagaggta tatttgcatt ccaacttcat    92220
cggctcatgg gattcccggt atttcgggcc ggtacctgtt tcaggtgtgc tcggtctggc    92280
gcaagaggtg ttgacctatg cgccgtgagg tcaggatgac tgccgttctc gtcccgcttg    92340
ccgtggtcgc cggggcggtt ggctggagcg gccaggcgtt cctgctccct gcggcaacac    92400
tcttcccgct tctgtgggcg cgatcaccaa cgcggatcgc agcggccctc gtcgcggccg    92460
gctatttcct ggcggcgtca cggggtttgc catccggcgt cgcagagttc tttgctgagg    92520
atctctgggt cagcctcagt ttctgggtcg cggcggcatc gtctttcgtt gctgtccatg    92580
cggcgctttg gacgatgcgg tcgggctcgg caaaatcagc acgctatctg ctcatcttgg    92640
ctctcaccgg tctgccgcca ctcggcatca caggctgggc gcatccgctg acggcggccg    92700
gcatactgtt tccagaatgg ggatggtggg ggcttgtcgc gttgacagcc ggcctgatcg    92760
gtctcgtaac ccggatcggg ccggctatcg ccattgccct gtcaggtcta tggctttggt    92820
ccgccgcatc ggggacaaat cagattcttc cggaggggtg gcgtggtgtc gaccttgaaa    92880
tgggcgcgag tctcggccgc gatcaatccc ttcgacttca acgtgacctg gtgacggctg    92940
ttcggcaggc tgccggaaca cgagagaccg tcgtcgtgct ccccgagagc acactgggct    93000
tctggacgcc aacgcttgaa cgtttctggc ggaatgagct gcaaggaacg cacgtgactg    93060
tagtcgccgg cgcggcggtc gtcgatgcgg ttggctacga caacgtcatg gtggccatcg    93120
atgcgcatgg ggggcgtgtc ctctatcgcg agcgcatgcc tgtgccggtt tcgatgtggc    93180
gtccatggga gcgatggaca ggagagactg cggcgcccg cgccaacctc ttggccaatc    93240
ccgtcgtcga ggtcgcgggc cgaaagatcg cgcctcttat ctgctacgag cagctcgtac    93300
tgtgccccat tctccagtcg atgctacacc gacccgacgc gatcgttttg atcggcaatg    93360
gctggtggac gacgggtggc aacatcgtcg ccatccagcg cgctagcgcc aaagcctggt    93420
ccgctctgtt cggcgttccc cttgtgattt ccttcaatac ctgaactttg gagccttcgt    93480
catggatgct gcctttatcg cggaatgcgc cgatctctcc ctgaaacccg ccatcgtcga    93540
gcagttcgta gccgctgtcg gtcctggcga tcccctggct gtcacggtca atccggagg    93600 gcggctcatc cttgtaccaa aaccgaagac cccagacgag gcaatggagg tcatacgcca    93660
gtatgtcgga caggccgtcg tgcgtgtggg cctgacacag ttcccggcgg gtgtcggcgt    93720
gaaggacgcg tccgcgctga aaccagatct ggttgaccca tgcgaaaatc ttcgcatggg    93780
gacgaggatg tttcaaaga tcatgcgcat cgtttcaaag tggtatggca acccaacgag    93840
cagtgaggtg cttccgcaga tcttcgaaga tgccgtttac gcctggaaca ccggccagtt    93900
cgaaggtgaa agcgtgtttc aggcggagga tccaggtggt acaatcgtcg atcggaagga    93960
agtttcttcg gatgccgcag acaaacctgc tgatgccacc gcctcccaga gcgaagggga    94020
```

```
gccctcagac gaaaaggagg ttggaaccgc gggaattcgg gtcgatttgt cccggatcgg    94080
tgggcagaag tagtgctgta tccgacttcg acgacaggta aaatatcagg gatcaggttc    94140
gacaattgcg acattgaggt cgttcagtac atcagccaga cccggcgcgc ggatcagctt    94200
cgtcgtgcgg accgccttca gttttccaat agctcgatcg aacactgcaa ggttggtgtg    94260
gccgttgagc cgagacgggt agatgatgcc gtccacctgg ctgtcgtgtt cattgaaggc    94320
gaccgcccac ttccgtgcga gggattgctt tgagcccttc gcgacatccg tcggcacacc    94380
catcttgatc ggcccgtcgt ctcgaagatc gaccatcatc agcggattga tgacctcgat    94440
ctctgcgaaa ttgcggtcgt acaattcgga ttcagctatc ggcaggtcgc cgaggacccc    94500
atcgcgctga tcgcgcagga cggcttcgag aaagcacacc ttcactgtat cgcccaaata    94560
gagcaccccg aaccggttag cgaattttcg ccggcgtgga tcgctgaaac ggctcggcgt    94620
cttaccgaag cctagcggat cggggtatgt gcccagatag atgcgaccga accgaagtcc    94680
ggccgcgacc gtatgaaggt gaaggctcgc attcgcaaag ccgggaggcg gcagaacacg    94740
tgccattcag cggaaatctc gaccaatgct ctcgacaacc tcgagcgctt gctcggcccg    94800
tccccgctcc aatgcctggc gacctgtcag tccgtccagc tctccgtggg gctgaccag    94860
gaagcggtaa accgcccaag ctccgcccag tcgctcgtgg agcgttgcaa gcgctgcaaa    94920
cggcttgcca tcggcatcga tctgccaatc cgggaagcga aagccgcgtt tcgcgccatc    94980
cagccccaat accagtccgg tctggcgctt tgaattcacc gttacccgtg tcgtgccaag    95040
cagcttggcg aattcgtcgg cattcagcat gtcagtgccg ctgaggacct cagcagcctt    95100
tatgcgtccc cgcgcccgtg cggccaccaa cgcctgctcc aattccggat ccagtgcatc    95160
gttctcctct acgacaggca ccgttgtcat ttccaccgcc tcaacgggag tgacaaccat    95220
ctcaccttcg gaatcgacat cgacacggaa gctgaccggg tggccagcag aacggctttt    95280
tgcgatcgct tgaccatatt cctggaggag cgccttgacg cgattgggat tgccggtcag    95340
ggcttttgat gcattgtccg ggatcttgat cttgaaggcg gctctcccct tcgccagcgg    95400
ggcggcgcct gtggtcagga aaaagccat ggattcagcg cccggttttt cgcgcccgct    95460
tgcaccgtca cgtatgctgg ttttggactt cagagatgcc atctctcacc ctccgttcgg    95520
agagctatat atggcaaggt tggttaagtt cgtcaagttg gtaaagagcg tagcgctcct    95580
gatcttctgt gtcctgattg cggctacgtg gacgactgcg gagtgatcga cgacaatcat    95640
ggttgatgca ggtcgtcgag gatttctttc ggggatgatg tatcaagcag cggtagggca    95700
gaaaccttt cccgatcgc tgtcatctgt tcgacggtca tgcgatgtct cacaggcagg    95760
tcgccgaaaa ccccgagagc ctgagcttca cgttcgaggg cagcgcgtat gatatcgtcc    95820
ggtctgcgcc cgacacgggc cgcaatttta cgggcaagct gctcggtgtc gtgggtaagc    95880
tgcaacatgg gttcgctcta aatgggtcct tccatgtaaa gcatttctca aaacaatgac    95940
agatttctgc tcagggccca tgaagctgag atcgcttggc caattgtgag ctgacacgtt    96000
ttccgcgagt aagcaaaatc cgtggtttgc aattccgaga aacgattta gaaaccatt    96060
ccttgatggt caacttacgc gattgaatat gccttattct ttgccagatc actgttcgca    96120
cgcgtcgcga tccttctgac tgcgacgcat tccgccactg cggaacaggt gcgatccaca    96180
gggagattat ggatgtcaaa ctgggtcgag aaactgctgg atatcaccgt gatcggaaat    96240
gatcagtcca tggtcaaggg cgctctggcg aatcttgctg atcggttcga ttttgtgggc    96300
tatgccttcg tcaacattcg tccggggcag acctatgcgg tctccaacta cgatatcgac    96360
```

```
tggcagaaaa tctatgacac gctggactac cggttcatcg atccggtcat gcggcaggcc   96420
cagcttataa ggcgcgcttt cgcctggtct ggcgaagccg acaagagctc gctgtcaaaa   96480
gagcagaaaa acttcttttc gaaagccgct gattttaaca ttcgctcggg cgtttccatc   96540
ccggtcgcca ccgccaacgg tgcgatgtcc atgctgacct ttgcatcggc gaagccttcg   96600
cttgccagtg atatggagat cgatgcgatt atggctgcct cagcggtcgc ccagcttcat   96660
acgcgtcttg agcacatgcg ggtcacgccc tccatcgagg aaaagatcgt cttgacgccg   96720
aagcaggtga actacattcg ctggctgtcg cttggcaaaa cggtcgaggt gatcgctgaa   96780
ctggagcagg caaagtatgc tggcgtccgc tctgcgattg acgatgtcag aacgcgctac   96840
aatctggcca atcatgcgca ggtggtgcct ttggctatac gacgcggcct gatttaggct   96900
gatctggcgt atcaggcctt gggcgtatag cccagaatgt gcagcagggt cgtcagggct   96960
gacatttgcg cgtgcatcct gatggttgcc tcgagatagg caatattggc atcgccaaga   97020
agctccttac cggctttaac gtcagccggc agttcattga acagattttc tgcccgctcc   97080
aacagtttgc gatgttcacg gatcgcatcg atcgtgagac gctcgacaag cggtgacgga   97140
agcccatgca ggagcccttat cagcggcttc agatcgactg cctcgccatt caatcggtcg   97200
tcggcgtcca tgttcaactc ccaaaacagg aatgcgcggt tcgcccccgc atagttcctg   97260 accccctggcg atcggggagt ttgtaaccga gcacactcag cccatggacc tttagttccg   97320
aggaacctgg acatacgtcc acggctcccc gaccataggt cgaggaattc ggcgccctaa   97380
cggcgggcac caaaccggtg tgcttcgggt acaaagccc ggaggcagcg cgtactgcct   97440
caccagcgct tatagcgacc taaccacatc cgcgccaccg cagatttgtt ggcgtccgag   97500
gtcggctcgc ggccagcgat tgaagaagga gactggaggc gttgtcgctt tggtgtccaa   97560
aatgaaacgg gtgatcgtcc aatagtcaaa cgaagttaac ctcggcattg cgatgcctct   97620
cctcgccgtg aagttgcgtt tgaaccacga aagcaatcag gctacagcac gatcccttga   97680
agttctgcat cgccgccgaa atcggttggc tgatcattcg atctctgcgg cggattgtca   97740
ggtcgcagtg ctggaagcgg atattgacac gatctctcgc cgattttttcc gacgttaagg   97800 aacgccttgc aaagacgggc tcggtgacgg aagcgctcca tttcatacag tcggtctatc   97860
gcgtcgattt cataacctac caccttgctt cgacggtgat cggtgatttt gatgctccgt   97920
tcgtacgcac gacctacccg gatgcgtggg tatccaccta tctgttgaag ggctatgtca   97980
ccatcgatcc tgtcgcgcgg gagggctttt tgcgccagct gccattcgat tggcgagaac   98040
tcgacgtcac gcccgagatg ctgatgtttc tggaagacgc aatacgccat gggatcggcc   98100
gttttggttt ttccatcccg atatcggata aagccggccg tcgcgccatc ctctctttga   98160
attcgaacgc ctccgccgaa gactgggagg atctggtcag tgctcatcgg agtgaatggg   98220
gcgatctcgc gtatctcgtc caccagatgg cagtgttcga gctacatgga gcgagcgatc   98280
cgatcccggc tttaagtccg cgggaacgtg agtgcctcta ctggagcgcg ctcggcaagg   98340
attacaagga tatcgcgctt attctcggcc tttcgcatca cacgacccgc agctacatca   98400
agtcggcgag gacaaaactc ggttgcgcca cgatctcggc ggcggccact cttgccctga   98460
agctacgcgt gatcacgata tgagccgacc gcccgccagt cttgtgacaat acccgcatat   98520 gggtctgacc atatgcggga atatctggct cctccgccaa gcggcatctt ccagccaaga   98580
tcaacagctg gagataaacc ttgttcattc tggttcaagc gcatcaatac acccgttatc   98640
aggctctcat ggatcaggca tttcgcctgc gaaaacgcgt ctttcacgac cagctcggat   98700
gggccgtcac aatcgacggt gattgcgagc gcgacgaata cgatgctctg cggccggctt   98760
```

```
acctgatgtg gtgcaatgat cgcgcggatc gcctttatgg aacccgtgcg ctgatgccaa    98820
ccaccggccc gacgcttctc tacgacgtct tccgcaacac gtttgcgggt gcaaacctga    98880
ttgcacccgg tatctatgag ggaacgagaa tgtgcctcga tgaggaaaca ctttccgtgg    98940
atttcccgag cctggaaacg ggcaaggctt tcggcatgct gttgctggct ttgtgcgaat    99000
gcggattgtc gcacggtatc gagacgctgg tgtcgaacta cgagccgcac ctagcgcgcg    99060
tctatcgtcg ggcggggctc gccgttgaag aggttggccg cgcagacggc tatggtcgct    99120
ctccggtttg ctgcggtatc ttcgaagttt cagaggaagt tcgcacgcgc atgcagcagg    99180
cgcttggtgt cgcggctccc ctttatgcag gatatcggcc gcgcaaaaat gcagccagcg    99240
agcccgtgcg catatctgcc tgatccagga gttgtcccaa ggcggttgcg gcaacatgtg    99300
cctcaaccgc cataatttcc gggaaagaca atgtcctggt cgacgagaac gttgaacttg    99360
tagcccggcc ggatctggat ggtgggctga acattcagat tcttggaaat cgtctgctcc    99420
gcgacgcggc cgaaggtctc cgcaaagttc ctgcgtgccg cgtcagaggc tgtatcctgt    99480
gtggcgaggg tggaactcgc cggaaccgcc atatcgatgc cggtaccaat cagtgcaaca    99540
agcgccgcca aaccgaaggt gcggaaatag tgattattga ccttgtcaga gaacccgcca    99600
tagccctgcg agtctgttcc agccatgccg ccgatctgca gtgtagagcc attcgggaag    99660
atgacatccg tccagacgac cagaacgcgg ctttggccaa acgagacctt gctgtcatag    99720
cgtccgagta gtttggtacc ctgcggaatg agaagaaaat gcccggtggc gctgtcgtag    99780
atgtgctggc tcacctgcgc tgtgatccgg cccggcaaat cggagatgat gccggtaatc    99840
atggtggccg ggatgacgga gccgcgcttc aattcatagc gtgactgttg gggtacaacc    99900
tggttcggca ggtagccgag atccttgatg tcggcgttga agaaatcttc cttcgaagtc    99960
tgtccgttcg gatcggcatt ctggcccatc aaacccgatt tcatggccgc ggcgtagaga   100020
tcagaggcgc cgttattggt ggtcggctgc cggtctgttg tcctggtgtt gctggagata   100080
tttcccagct ccgagatttt gaccttcagc ggcgagtcaa acgcagtcgc acgggcctga   100140
aggctggcca tccgctgtcg ctgctgttca cgcaggactt gttcgcgctg ttcgcggcga   100200
agtcgggcca accattcttc ttccgactcc atttgcggtc ggcgctcttc tcgtgcctgc   100260
tgctttatct gctcttcttc aatcggcttg gcctccacct gtgtctgggt tgctggcgtg   100320
ggctggaata cgggctgctc ttcgcgatcc ccgatgatgc cgtctttcac cccgcgcttc   100380
atctgatcag cgaaggtcga ggccgggacg ttcgagcctg cttcatccgg aattctgtcg   100440
ccgaaccgca gtccccggga tgagatgccg tagacaagga caccggcgac gacgactgcg   100500
ataccgatgc caaagaacac cggcaggcga ttgagccgtt tcatgcccct tcctgcgcg    100560
gcgctgctcg gattgccgag ctggagcgac tggaccatat ctgtctctcc ttagtttcgc   100620
ttcattaatg aaagcgggct cgccggcgtg gcgccacctg atgacacaga ataggcccgc   100680
ccaagctcaa gcgtctcgct ggaaagcctc actagtacct gtccgtcgat gtcgatcaac   100740
gagtatgcca gttcgatcgg tttggcggtg tctttcccccg agcgtgcctt gtcatccgtt   100800
atgacagtga aaccccaccc ttttaacgcg gcttcgagcg cggccgcgaa atctgatgcg   100860
tcgctgtgaa gcctgatcgg cgtggcggtt gaccctgcct gctcggcata acgtccagct   100920
atgtcgccgg cgatcgcgct tgcggcgggg cctgttacag tcgaaggcgc ggggctcgtc   100980
gtgagcgcgt ctgttccggt ctggcaacca gagagaagaa cggcagcgac aaagggaaaa   101040
aggcaaaggc gcatcgatca gcctccccgt cggatggtga ttttctgctg acgccagccg   101100
```

```
acgccggaaa cgaggacagc cttgtcgata ttgtagtcga taatcatcat attgttcttc   101160
atgcgataat tgacgatccg gttttgcccg ccagagacca cgaagaggac cggcgcatcc   101220
tgaccggata gtgcgcgcgg aaactgaatg taggtcttct gcccgtctga atagacgcgc   101280
ttcggcttcc agggcgcgct gccactcaga gaataggcga aggcaagttg ctctggcggg   101340
acgccgccgt cggaattggt catcgtctga atacgagcat taatgtcgga cagtctcgtc   101400
gcggcctctt ccggatactc gaagccgacg cgggccatgt actggttcgg gtgcgatttg   101460
agctggatat gataggtgcg tcttgaggtc gtcaccacca tcgacgtcac cagacccgcc   101520
tcagacggtt tgacgatcag gtgaattgcc tgcccccctg cagcaccgga tgttgccggc   101580
tcgaccttcc agcgcaccgt gtccccgaca agcacgtcgc gcacgatctc cccaccctga   101640
agctcgatgt cgcagacctg taaaggtgag cagacgacag acggctgcgt ctcaccgaac   101700
aggaagatga cttttccgtc agcgcccgtt gtcaccagtc cccgctgccc acgccatttg   101760
ttggagagcg tggttccctt agcctcattc gtcgtcaggc tctgggcaaa acccgatgtc   101820
gtcgccgtga ccaaaagcgc aagtgcggtc atgcagcaaa gcgctgcccg atttaaccTT   101880
gtattcattg aagtcccctg cccttacagt tgcgcggtcc agtcgaagtc cttgacatag   101940
aggccgatgg gattgagccg gatcgtcgcc tcgtcctggg gcgcggtgat cgccaccgtg   102000
gctatgccgc gaaatcggcg tgtcgcaatt tccttgccct tgcggtcccg ttcgtactca   102060
gtccagtcga tctgataggt ctggttagac agcgcgacga tgttgttcac ctcgatggcg   102120
acggtcgcat tcacggcctt ttcgaatggc gagttgccgc ggaaccaggc attgatcttt   102180
tgggtcgagg gatcgcttgt cctaagaagc gcataggtcc tgtcgatgta ttgcttctgc   102240
acgacggcat caggcgtgat agagcggaaa ctggtgataa agccgccaag cgtggcccgg   102300
atgaccctgg catcggcata ttcgatctgc tggggaaatc cggcggagac ggtgtttccc   102360
agcttgtcga cctcgacgat gtacggcacg agtttgacct gcgtgctcag atacagtgag   102420
tagccaaaac tgattaccgc catgccgagg ctcaagatgc cgaccgtccg ccatgcgagc   102480
gctgccctta cgtaagaacc gtatcgttcc gaccattcct gccttgcggc aagatacggg   102540
ttctctgggg cgcgttgcgc tgccatattg ttttccctgc cttaaattta cgatttgtcc   102600
tgccgctccg gcggctgacc gggcgaggct cccttgccac gagcctggtc gagcttcgcg   102660
ttagccaggc caaggatgga gccggcatag gccccgggcg acccgatcgc cttctctttg   102720
gctgcggatc ctgcggcttg tgctcctgaa ccaaagctag cgccaatccc gcgaagagta   102780
gcgccggcg tcgaagaccc cgccgcccgt gccgattgtg ctgctgcata tcctgcccca   102840
gcagcgccag ccgcaagaaa agcggcgcct gcagcgaagg aagcgccctg ccgccatgg   102900
cgaatagtct ccatgccgcc agtgacggac gctccctgaa cgacccctg gataatgttc   102960
ggcacgtaca tggcgatgat gaacaccacg acggcgatgc cggcgatcgc aagtgcggtc   103020
tgaaattgat cgccgatatt tggttcgttg gcgagcccga ttagtacctc ggaaccaata   103080
cgggagatca taacgagcgc catcagtttc atgccgaccg aaaacgcgta gaccagatat   103140
cggacagcaa agtccttggt gaacgacgag ccgccaagcc caagcatgat catcccggcg   103200
agaaggccaa gatacatctc gaccatgacg gagacaaaga ttgctgcgac gagtgaaaat   103260
gcgatcaccg tcacgaccat tgcaaatgcg gccgatatcg ccagtgcatt atcctcgaaa   103320
agtccgaact gcactttcgc tgacatcttc gttgctaccg tcagaccggc attgaagacg   103380
tctgcaggtg aggccgtacc tcctccggca ccgatctgaa aaagactgtc caccacggct   103440
ttggcgaatg tcggtccttg cgtcagcacg aaggcaaaga atcccacaaa catgatccgc   103500
```

```
ctgacgagct cggcgaacca gctgtccagt gatgcggcct gcaatgccaa ccaaacagcg   103560
gcaattccaa tctcgatggt ggcgagaatc cagaagagag atttcgccgc gtccatcacg   103620
gtggtctccc acccttggc cgcggttgta atctgggtct aagagacgt cagaacagag    103680 ccttcctgcg caaaagccgg gtgagcaatc acgacaggaa cggtgacaag tagcagagcg   103740
acccgcaatt cgctgttgga gatcgtcatt ggttcaccat tcgaccttca tcttctctcc   103800
gccagaagtc gggtaggtct tcgacgaacc gaaaaatgtt gcgcggaggt gttgcgcctc   103860
ctgtttctcg gacatcagga accatagccc ggcgctgccg acagcgagca aagatgcgac   103920
tgcgatcaag atcagcttcg ttctcaccat tcgaccttca tcttttcgcc gccggaggtg   103980
gacggtgctg cgccgttgaa gaattccttc cgccgagctt gtgccagatc cttgtcggtc   104040
tgctcgcttt gcagccacgt ccccatcatc gtcatctgct gggatacgag accacgcagc   104100
ttttgcgttt gcgcaacctg ctgcgctgca atctcgtggc cgacctggag agctttcatt   104160
tggccatcgg ccgattccga catgtttcgg agcgagtcca tcgtatcctc ctcgctgtcg   104220
aactgctcag ccgtcaggct tgcggccttg agtgtgctgg cgatggtgtc gcgattggta   104280
tcagaccaac tggcatagtt tgaggacagg tctgtcccgc tggcggcggc agtctgtaga   104340
tcggcatagg attgaaagcg ctgcttcagc acatcatccg cgctccccat agagaaagag   104400
atgctctgtc cctgatcgac gatatcccgc agcggttga ggtcgttttc gacttggccc    104460
cagatgtgat cgggcagctg cgccgtgttt tgcagcatat tctcgtagat gttcagctgg   104520
ttttggatct gctcggccaa ctgactgatc tgtgtcagct gattgtcgac ttgcaggccg   104580
gagcttttaa ggaggtcgac gagctgtgca ttgttggcaa gctgtgtcca ctcggttgca   104640
gcgcccgtcg ctgagccggc aaatgctggt gccgaagcgc agactgcaaa agctgccacg   104700
atagcggtcg cggattttct tctgagcgat aggatatggt caggcatagc gattgatccc    104760
tctttcattg agccattggg tcggccagtc tttgccgtag gttgagagaa gttcccggat   104820
ccgagcgagg tcggctttgc cggaagcacc gacgaaggag agggtgagcg gccccagcgc   104880
catatcgaaa aggcggcgtc cgtccggcga cgtcacgtaa tattcccgct ttggaatggc   104940
ggctgcgacg atttcgattt ggcgaggatt aaagccgatg cgctcataga attctcgtgt   105000
cccggactcg cgtgcagccc cattcgggag gcagatcttg gttgggcagg attccttcag   105060
gacatcgatg atgcccgaac gctctgcgtc cgaaattgac tgagtggcga gaacgacggc    105120
gcagtttgcc tttcgcagca ccttcagcca ctcgcggatt ttgtcgcgga aaccgggtg    105180 gccgagcatc agccaagcct catcgagaat gatgaggctt ggtgccccg tgagccgctt    105240 ttcgatcctg cgaaacagat aggtcagcac ggggacgaga tttcgctcgc ccatattcat   105300
cagttgctcg atctcgaagc actggaattg accgagggtc agcgaatcct gttcagcgtc   105360
gagaagctgg cccatggggc cgtcaacagt atagtggtgc agcgcgtcct tgatctcccg   105420
catctgcacg ccactcacaa aatccgacag cgaccggcct ggagccccg ccatcaaacc    105480 gatctgccga gatatggcgt ttcggtggtc cgggttgacc gtgacaccct gcagggagac   105540
gagtgtttcg atccactcgg aagcccaggc gcggtcggtc tcggtcgaga ggtcggagag   105600
agggcaaaag gcaagcctag cccctccc tgcctcgccg ccgatttcgt aatgattacc      105660
atcaacggcc agcgtcagcg gcagaataga gttgcctttg tcgaaggcga aacctgcgc    105720 acccttatac cggcgaaatt gcgctgcgat gagcgcgaga agcgttgact tgccggaacc   105780
ggttggtccg aaaataagcg tatgcccgac atcatccaca tgaaggttca gtcggaaggg   105840
```

```
tgacgatccg gaagccacct gcgtcagtgg cggcgcgtcc ggtggataga acgggcaggg   105900
cgcaagtgga ctgcccgacc agacggaatt gaggggatg aggtccgcga ggttgcgggt    105960
gtttatcagc ggttcccgga tattgcagta ccagttgcct ggcaggctcc cgaggaatgc   106020
gtccgtcgca ttcaacgtct cgatccgcgc gccaaatccc tcagcctgga tcaaccttcg   106080
aaccgactca gctttatcgg cgagcttttc tctgctctcg tcgaatagaa tgatgaccgg   106140
cgtgtagtag ccataagcga ccagctgcga agaagcctcg cgatcgcgt cttcagtctc    106200 agcgaccatg gccattgcgt cctggtcaac cgatcggctt tgcgtctgga agagttggtc   106260
gaagaacggc cgcaccttct gttgccattt cttgcgcgtg cgctccaacc gctgtttggc   106320
ttcctcggca tccagaaaga taaagcgtga cgaccagcga taggtgagcg gcaagagatc   106380
gaggctattc aagatgcctg gccagctctc ggccggcaaa ccgtcgatcg caatcgcgct   106440
gaggaaccgg ttttcgactt cggggtaag gccgtgctct agctccgcgg tcgccagcca    106500
atccaaatac atgggaattt caggcagaca gactgggtgg ttttcaccgg tgatgcagaa   106560
ccggatgaac tggaacagct catcgtagcg ggcaatgcgg gtgccaccgc gttccggcac   106620
ctcacgcgtc cgcatacgct caatggagat gacgttgccg aggtattgct caatctctcg   106680
ggtggagcgc ctgaaactgt cgagcaccgt gtcggcatag gtcgccgtcc ggctctcagt   106740
gtccgagtag atataacgcg tgacgccaga tcgccggcgc tcgggagggc gatatgtcag   106800
gacgagcgca tgccggctct cgaaatgccc gcgctcttgt tcgaagtgct gcgccgctc    106860 atcatcgatc attcgagtga cagcatcggg gaaatgactg cgttccgcag aaggatagtc   106920
agttgttggg atgcgcacgg cctcgacctg gatcatccag ccggaaccta gccgtgaaag   106980
gatcgtattg atctgacggg acagatcgtt gcgctcgaaa tccgtggcgc tctcggagtc   107040
agggccggca aaataccacc ccgccatgag acttccgtcc ttgagaagaa tggtcccatt   107100
gtcgaccagt ccggcatagg gcacgagatc ggcgaacgac ggtgcagacg ggcgaaggga   107160
acacaaagcg accatcatgg cacctctaaa acgccgcca cggcgaagac gtgggcaggt    107220
agtgatgccg gtagcgcaaa tgccgcacgt agacatgacg catgagggga tcggatttg    107280 ccatcatgcg cagtgcgccg acgatcacga accagatggc gatgccgaac agcgctgaat   107340
acagggtgag cacgacgaag atcaggatga tcgccaccag ccctgtgaca agcaggagct   107400
ctcggtctgc ccccatcagc agattcggtc gtgaaagagc gcggtgaatg cgattgcgtt   107460
ggagagcgga atgcggctca cccattggcc ccctcccctc ttgcaacgga catcggctgg   107520
gaaacggtcc ctggcaaact tgtggcagtg atgccgatcg acgcgccggt cgcaccgaac   107580
agtccgacaa tcgtcgtcgc ccccagcagg ataccggcga ccagtacgat gtagacgagg   107640
cgtcgcgcga aatcgttgag ctcgccgccg aagatcagca ttccgccggc gatcgccatg   107700
gcggcgaggg caattgctcc tgcgactggc ccagtgatgg attcctgaat ctgttcaagc   107760
ggcccctccc agggaagact cccaccggaa ctggcaaggg ctggcgcggc aagcgccgcg   107820
cagaacatcg cagcgagcag tccgaggcga aaagagcgat tatgcagcat gaatgtcctc   107880
atcaatttga gcgtaatgtt cggtctggta ccggctaccg ctgaagccct cgacattgat   107940
gacctctcgt acccgtctcc ccctcccgc gcgctcgatc gagatgacaa gatcaacggc    108000
ctcgccgatc acagcctgca tcggttgctg gctgacctcg gcggtcagtt gctccagacg   108060
acgcaaggcg gacatggcgg tattggagtg gacggtggtg acgccaccgg gatggccagt   108120
attccaggct ttcagcagcg ttagtgcggc gccgtcgcgg acttcgccaa cgatgatgcg   108180
gtcgggacgg aggcgcatgg tgctcttgag cagtcgcgcc atatcgatcg tgtcactggt   108240
```

```
atgcaggcac accgcattct ctgccgcaca ccggatttcc gcagtatctt caagaatgac    108300
catgcggtcg tccggagctg aggctatgat ttcggcaatt acggcattgg ccagtgtcgt    108360
tttgcccgag ccagttccgc ccgcaattac gatgttaagc cgattggcga ttgcgctcct    108420
aatgactgcg gcttgggcct ccgtcatcac cttgtcagcg acataatcgt caagcgggat    108480
cagccgtgac gctcgccgcc ggatcgtgaa cgttgggac gcaacaaccg ggggcagcag     108540
cccttcaaag cggtgcccgc caatgggaag ttcgcccgaa atgatcggcc gctcttcgtc    108600
cgcctcagat tgaagagcgt gtgcgacgga gccgatgact gtttccgctg ctgtcgccgc    108660
catctcaccc gcgggcgcaa tgccctgccc taaccgctcg ataaaaactc tgccgtctgg    108720
gttgagcatg atctcgacga ccccagggtc gtcgagggcg atacatagac gatcgcccag    108780
tgcttcttga agcttgcgca caaggcggga atgcgactga agcattgcga cgttctcctc    108840
gctgattgat ttgggggaga aaaaagcggg acggcaccaa gctgtccacg tacaaatttg    108900
tacctcgcga ttctctgtcg tttcctgcac ggtggcgc                           108938
```

<210> SEQ ID NO 2
<211> LENGTH: 37
<212> TYPE: DNA
<213> ORGANISM: artificial
<220> FEATURE:
<223> OTHER INFORMATION: Primer AIOf_XbaI

<400> SEQUENCE: 2

```
ggtggctcta gacagcggct tcacacatag tccccag                              37
```

<210> SEQ ID NO 3
<211> LENGTH: 28
<212> TYPE: DNA
<213> ORGANISM: artificial
<220> FEATURE:
<223> OTHER INFORMATION: Primer AIOr_Bsu15

<400> SEQUENCE: 3

```
ggtatcgatg cacccacgat ggcgagag                                        28
```

<210> SEQ ID NO 4
<211> LENGTH: 30
<212> TYPE: DNA
<213> ORGANISM: artificial
<220> FEATURE:
<223> OTHER INFORMATION: Primer ArsF_Bsu15

<400> SEQUENCE: 4

```
ggtggtatcg atgaaaagca ggcagaggcc                                      30
```

<210> SEQ ID NO 5
<211> LENGTH: 38
<212> TYPE: DNA
<213> ORGANISM: artificial
<220> FEATURE:
<223> OTHER INFORMATION: Primer ArsR_Xba

<400> SEQUENCE: 5

```
gtttctgaga cacttcttga cgtagccgca actaactc                             38
```

<210> SEQ ID NO 6
<211> LENGTH: 20
<212> TYPE: DNA
<213> ORGANISM: artificial
<220> FEATURE:
<223> OTHER INFORMATION: Primer ParsH-L

```
<400> SEQUENCE: 6
tgacgtagcc gcaactaact                                              20

<210> SEQ ID NO 7
<211> LENGTH: 20
<212> TYPE: DNA
<213> ORGANISM: artificial
<220> FEATURE:
<223> OTHER INFORMATION: Primer ParsH-P

<400> SEQUENCE: 7
tggcttgtgc tgcgaataag                                              20

<210> SEQ ID NO 8
<211> LENGTH: 20
<212> TYPE: DNA
<213> ORGANISM: artificial
<220> FEATURE:
<223> OTHER INFORMATION: Primer aoxBF

<400> SEQUENCE: 8
ccacttctgc atcgtcggct                                              20

<210> SEQ ID NO 9
<211> LENGTH: 20
<212> TYPE: DNA
<213> ORGANISM: artificial
<220> FEATURE:
<223> OTHER INFORMATION: Primer aoxBR

<400> SEQUENCE: 9
gtcggtgtcg gataggccat                                              20

<210> SEQ ID NO 10
<211> LENGTH: 20
<212> TYPE: DNA
<213> ORGANISM: artificial
<220> FEATURE:
<223> OTHER INFORMATION: Primer repAF

<400> SEQUENCE: 10
cgtgcgctat cttcagacgg                                              20

<210> SEQ ID NO 11
<211> LENGTH: 20
<212> TYPE: DNA
<213> ORGANISM: artificial
<220> FEATURE:
<223> OTHER INFORMATION: Primer repAR

<400> SEQUENCE: 11
gcttgagttc ttcgtagtcc                                              20

<210> SEQ ID NO 12
<211> LENGTH: 20
<212> TYPE: DNA
<213> ORGANISM: artificial
<220> FEATURE:
<223> OTHER INFORMATION: Primer traIF

<400> SEQUENCE: 12
gtgctcatcg gagtgaatgg                                              20

<210> SEQ ID NO 13
<211> LENGTH: 20
```

```
<212> TYPE: DNA
<213> ORGANISM: artificial
<220> FEATURE:
<223> OTHER INFORMATION: Primer traIR

<400> SEQUENCE: 13
gacatcaagg atctcggcta                                              20

<210> SEQ ID NO 14
<211> LENGTH: 20
<212> TYPE: DNA
<213> ORGANISM: artificial
<220> FEATURE:
<223> OTHER INFORMATION: Primer 12F

<400> SEQUENCE: 14
gcaatcggtc tcacaagagg                                              20

<210> SEQ ID NO 15
<211> LENGTH: 20
<212> TYPE: DNA
<213> ORGANISM: artificial
<220> FEATURE:
<223> OTHER INFORMATION: Primer 12R

<400> SEQUENCE: 15
aaggcgcaca tcagctcgaa                                              20

<210> SEQ ID NO 16
<211> LENGTH: 20
<212> TYPE: DNA
<213> ORGANISM: artificial
<220> FEATURE:
<223> OTHER INFORMATION: Primer 27F

<400> SEQUENCE: 16
agagtttgat cmtggctcag                                              20

<210> SEQ ID NO 17
<211> LENGTH: 19
<212> TYPE: DNA
<213> ORGANISM: artificial
<220> FEATURE:
<223> OTHER INFORMATION: primer 1492R

<400> SEQUENCE: 17
ggttaccttg ttacgactt                                               19
```

BACTERIAL STRAINS, PLASMIDS, METHOD OF PRODUCING BACTERIAL STRAINS CAPABLE OF CHEMOLITHOTROPHIC ARSENITES OXIDATION AND USES THEREOF

RELATED APPLICATIONS AND INCORPORATION BY REFERENCE

This application is a divisional of U.S. patent application Ser. No. 14/163,565 filed Jan. 24, 2014 which is a continuation-in-part application of international patent application Serial No. PCT/IB2013/055577 filed Jul. 8, 2013, which published as PCT Publication No. WO 2014/009867 on Jan. 16, 2014, which claims benefit of Polish patent application Serial No. P.399883 filed Jul. 10, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention provides novel strains *Agrobacterium tumefaciens* KKP 2039p and *Paracoccus alcaliphilus* KKP 2040p, the plasmid pSinA and its functional derivative, a method for producing bacterial strains capable of chemolithotrophic arsenite oxidation, and novel bacterial strains produced by this method. The invention also provides a composition comprising a novel bacterial strain or plasmid pSinA or its functional derivative and the use of these novel strains as well as the method of bioaugmentation of an arsenic-contaminated environment, particularly the method for the removal of arsenic from waters.

BACKGROUND OF THE INVENTION

Arsenic is among the elements which are widely distributed in the Earth's crust, where it is present in trace amounts, mainly in the soil and minerals. Under the influence of natural processes and human activities, arsenic is also released to waters and air. The presence of arsenic compounds in drinking water sources poses a threat to human and animal health. The most dramatic effects of the influence of arsenic are observed in Bangladesh and in Western Bengali in India, where, according to the World Health Organization (WHO), over 50 million inhabitants are exposed to the consumption of drinking water contaminated with this toxic element.

Biological removal of arsenic from contaminated areas seems to be a necessary complement to many traditional, chemical methods of remediation. The use of such methods as coagulation or filtration is associated with the removal of not only arsenic, but also other elements present in the treated environment. Current studies on biological systems for arsenic removal, mainly focus on the use of the potential of microorganisms and plants (Kostal et al., 2004, Tripathi et al., 2007).

Effective purification of an arsenic-contaminated waters is associated with the removal of both inorganic forms of arsenic (As III and As V). While arsenates can be efficiently and selectively precipitated on strong adsorbents (Pattanayak et al., 2000), in the case of arsenites there is no possibility of using selective oxidants without side effects to the environment. Microbial oxidation of As (III) becomes therefore an alternative to chemical oxidation. Lievermont et al. (2003) proposed an efficient, low input, two-step technology for arsenic removal from waters with the use of *Herminiimonas arsenicoxidans* ULPAs1 bacteria. The authors have demonstrated that the strain ULPAs1, immobilised on alginate deposit, can efficiently oxidise even 100 mg/L of As (III) and may be applied in technologies for the removal of arsenic, where initial oxidation of contaminated waters is required.

The known applications of arsenite-oxidising bacteria in bioremediation processes are so far limited to laboratory studies and ex situ methods. The known ways of bioremediation of areas contaminated with arsenic by in situ methods do not fulfill their functions, because bacteria introduced into the "new" environment are not able to survive in the new conditions. This is mainly due to the existence of physico-chemical conditions other than laboratory and to the interspecific competition with the indigenous microflora. The proposed solution to this problem is the biostimulation of indigenous microflora or the use of genetically modified organisms.

Yang et al. (2010) relates to a lab constructed vector, derivative of the plasmid pBBR1MCS-5, carrying genes for the large and small subunits of arsenite oxidase. This vector contains the gene for resistance to gentamicin and its use requires an application of selection pressure of gentamicin at concentration of 60 mg/L. Because of this, an introduction of bacteria harbouring such plasmid into the environment carries the risk of dissemination of genes for gentamicin resistance, and also involves the risk of instability of such strains in the environment. The vector of Yang et al. (2010) is used for constructing strains useful in bioremediation of arsenic, but it only works when introduced into strains originally capable of arsenite oxidation, and it only increases the efficiency of the already existing process. This vector does not cause the acquisition of a new ability, which is the possibility of catalysing the oxidation reaction of As (III) to As (V).

The proposed use of genetically modified organisms involves the introduction of foreign genes carried by them, such as marker genes for antibiotic resistance or encoding the green fluorescent protein (Gfp) into the natural environment, which is unacceptable for social reasons and undesirable for environmental reasons, as well as causing the loss of plasmids in case of the absence of selection pressure for the chosen markers in the natural environment.

Citation or identification of any document in this application is not an admission that such document is available as prior art to the present invention.

SUMMARY OF THE INVENTION

It is desirable for the microorganisms capable of arsenite oxidation to also show resistance to the presence of other heavy metals in the environment.

*Sinorhizobium* sp. M14 strain was isolated from microbial mats from a gold mine in Zloty Stok (Drewniak et al., 2008). This strain can grow chemolithoautotrophically using arsenites as the source of energy and can mobilise arsenic from arsenopyrite (Drewniak et al. 2010). Strain M14 carries two megaplasmids: 109 kbp plasmid named pSinA and about 300 kbp plasmid named pSinB (Drewniak, 2009). Partial sequence of the plasmid pSinA was revealed in the GenBank NCBI database under the accession number GU990088.1 (the revealed sequence corresponded only to nucleotides 21498 to 48497 of SEQ ID NO: 1 according to the present invention).

The aim of the present invention is to overcome the indicated inconveniences and to provide novel bacterial strains, plasmids, and methods enabling the introduction of a plasmid into a bacterial strain, especially an indigenous strain, in order to produce stable, improved strains, capable of arsenite oxidation, which, are furthermore characterized by an increased resistance to other heavy metals. Such strains may be simultaneously deprived of undesirable marker genes, such as antibiotic resistance genes. The aim of the invention is also to provide novel bacterial strains capable of arsenite oxidation, but not accumulating arsenic, compositions comprising them, and their use.

The essence of this invention is thus based on an unexpected finding, that it is possible to use the natural plasmid pSinA of *Sinorhizobium* sp. M14 to produce stable bacterial strains of various species of bacteria, capable of arsenite oxidation, preferably not bearing any undesirable marker genes, as well as on the development of a method for producing novel bacterial strains, using strains comprising this plasmid or plasmid pSinA. Surprisingly, it has been found that plasmid pSinA introduced into bacterial strains and species other than *Sinorhizobium* sp. is fully functional and stably maintained in them and enables such bacteria to chemolithotrophically oxidize arsenites. Moreover, it was unexpectedly found that unlike the *Sinorhizobium* sp. M14 strain, the new obtained strains comprising the plasmid do not accumulate arsenic inside their cells, but allow it to be processed, leading to the obtaining of biomass free of harmful arsenic.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with the IAFB Collection of Industrial Microorganisms of the Institute of Agricultural and Food Biotechnology in Warsaw, Poland, under deposit accession numbers KKP2039p and KKP2040p were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 2A-C. Shows a comparison of the ability to oxidise arsenites by wild-type strains (wt) *Agrobacterium tumefaciens* LBA288 and *Paracoccus alcaliphilus* JCM7364R and their derivatives *Agrobacterium tumefaciens*, deposited as KKP 2039p (D10), and *Paracoccus alcaliphilus*, deposited as KKP 2040p (C10) harbouring the plasmid pSinA. In order to compare the abilities of the investigated strains to oxidise arsenites to arsenates, cultures were carried out in minimal MSM medium containing 5 mM (375 ppm) of sodium arsenite. (A) and (B) show the content of As(III) and As(V) in culture fluids collected from the cultures every 24 hours. (A) shows a comparison of kinetics of arsenite oxidation carried out by the *A. tumefaciens* LBA288 strain and its derivative, the *A. tumefaciens* (D10) strain with pSinA; (B) shows a comparison of kinetics of arsenite oxidation carried out by the *P. alcaliphilus* JCM7364R strain and its derivative *P. alcaliphilus* (C10) with pSinA; (C) shows a comparison between the minimal inhibitory concentration (MIC) values for As(III) of the wild-type strains *A. tumefaciens* LBA288 and *P. alcaliphilus* JCM7364R, and their respective derivatives harbouring the plasmid pSinA: *A. tumefaciens* KKP 2039p (D10) and *P. alcaliphilus* KKP 2040p (C10).

*Sinorhizobium* sp. M14 and the newly created strains harbouring pSinA plasmid: *Agrobacterium tumefaciens* KKP 2039p (D10) and *Paracoccus alcaliphilus* KKP 2040p (C10). In order to compare the efficiency of the investigated strains to oxidize As(III) to As(V) and to remove the resulting arsenates, cultures were carried out in minimal MSM medium containing 5 mM (375 ppm) of sodium arsenite. As(V) content in culture fluids collected from the cultures every 24 hours is shown on the graph.

FIG. 5A-B. Photograph from the observations and analysis of granules of high electron density in the cells of *Sinorhizobium* sp. M14. A—Transmission Electron Microscopy. B—X-ray analysis.

Figure 6:
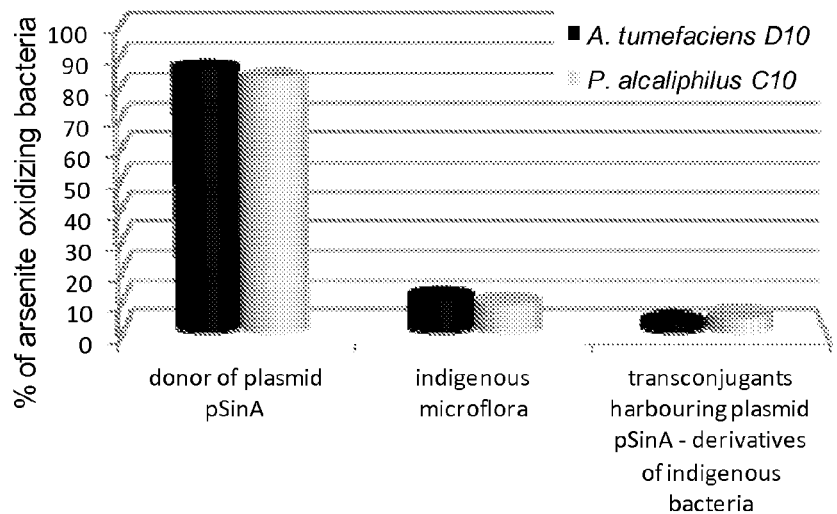
Figure 7:
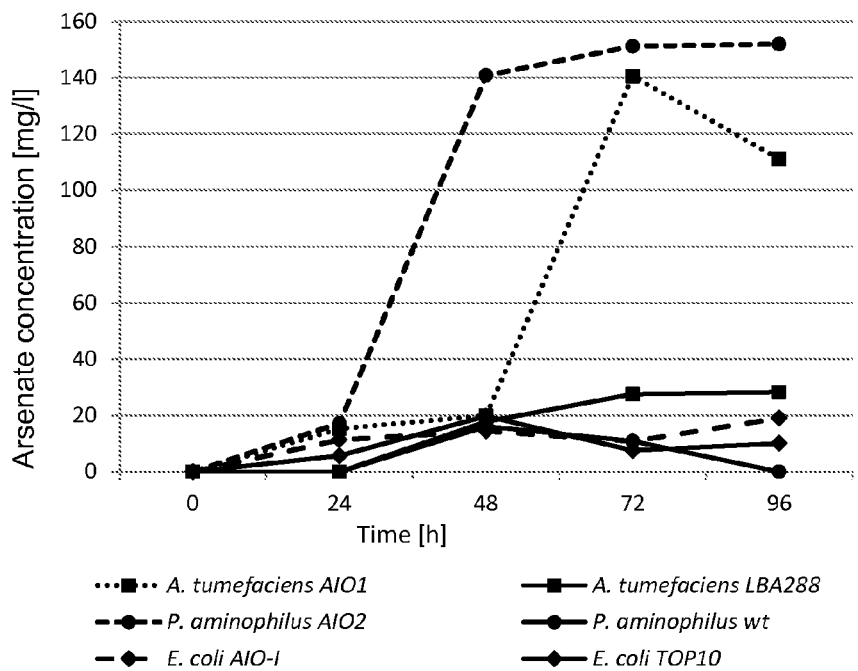

FIG. 6. Shows a graph illustrating the frequency of conjugative transfer of the plasmid pSinA from the produced strains harbouring this plasmid: *Agrobacterium tumefaciens* KKP 2039p (D10) and *Paracoccus alcaliphilus* KKP 2040p (C10) to the cells of indigenous bacteria. In the experiment, a soil sample from the Zloty Potok area was used. The frequency of conjugal transfer was assessed after 15 days of incubation at room temperature. ■—indicates the rate of conjugal transfer of the plasmid pSinA when *Agrobacterium tumefaciens* KKP 2039p (D10) was used as the donor; ■—indicates the rate of conjugal transfer of the plasmid pSinA when *Paracoccus alcaliphilus* KKP 2040p (C10) was used as the donor;

FIG. 7. Shows a comparison of the efficiency of arsenite removal out of the cell carried out by wild-type strains (wt) *Escherichia coli* TOP10, *Agrobacterium tumefaciens* LBA288 and *Paracoccus aminovorans* JCM7685, and their derivatives *Escherichia coli* AIO, *Agrobacterium tumefaciens* AIO1 and *Paracoccus aminovorans* AIO2 harbouring the plasmid pAIO1. In order to compare the efficiency of the investigated strains to oxidize As(III) to As(V) and to remove the resulting arsenates, cultures were carried out in minimal MSM medium containing 2 mM (150 ppm) of sodium arsenite.

Figure 8:
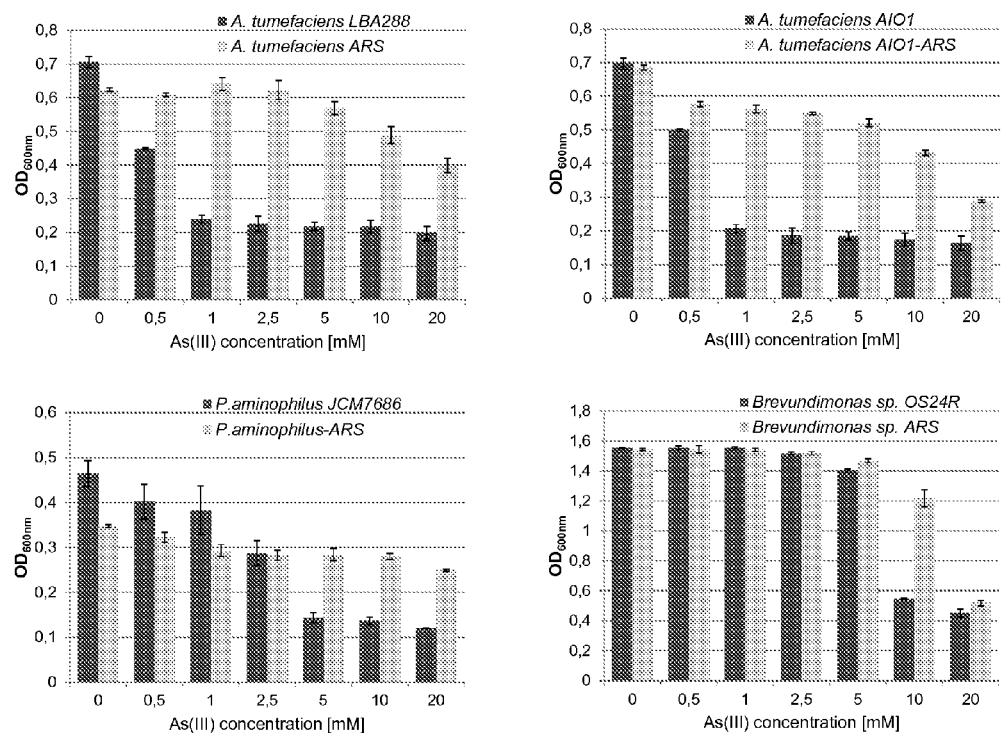

FIG. 8. Shows a comparison of MICs—minimal concentration of As(III), inhibiting the growth of the wild-type strains, and their derivatives harbouring the plasmid pARS1. In order to compare the MICs for As(III), cultures were carried out in LB medium, with various concentrations of sodium arsenite (up to 20 mM). After 48 h of cultivation at 30° C., optical density of the cultures ($OD_{600nm}$ measurements of absorbance at 600 nm) was monitored.

DETAILED DESCRIPTION OF THE INVENTION

The present invention concerns the novel strains *Agrobacterium tumefaciens* (D10) deposited under the number KKP2039p on the 30 Mar. 2012 and *Paracoccus alcaliphilus* (C10) deposited under the number KKP2040p on the 30 Mar. 2012 in the IAFB Collection of Industrial Microorganisms of the Institute of Agricultural and Food Biotechnology in Warsaw, Poland and functional derivatives (variants) thereof.

The term variant (derivative) of the novel strain or strains produced by the method according to the invention is to be understood a mutant strain or strain obtained by culturing the deposited strain or the strains produced by the method according to the invention as the starting material, which may comprise the plasmid pSinA shown in SEQ ID NO: 1 and is capable of chemolithotrophic arsenite oxidation.

Furthermore, the invention relates to the isolated plasmid pSinA shown in SEQ ID NO: 1 or its functional derivative.

The term 'derivative of the plasmid' or 'functional derivative of the plasmid' may comprise plasmids having a nucleotide sequence coding for open reading frames, encoding products comprising an amino-acid or a nucleotide sequence identical or highly homologous to the sequences coded by the original plasmid e.g. pSinA, wherein the coding sequences or other plasmid sequences which have been modified e.g. by substitution, replacement, deletion or insertion, such that it does not essentially alter the activity of the products of these open reading frames, and enables the maintenance of functional features carried by the original plasmid e.g. pSinA, such as the ability to chemolithotrophically oxidize arsenites and the resistance to arsenates [As(V)] and arsenites [As(III)]. A highly homologous sequence means that the sequence is homologous, preferably identical in at least 70%, preferably 80%, more preferably 90%, the most preferably, in at least 95%.

The invention relates to the use of novel strains: *Agrobacterium tumefaciens* KKP 2039p and *Paracoccus alcaliphilus* KKP 2040p, harbouring the natural plasmid pSinA of *Sinorhizobium* sp. M14 and the use of the plasmid pSinA of *Sinorhizobium* sp. M14 alone or its functional derivative, carrying: (i) all the genes necessary for chemolithoautotrophic arsenite oxidation, (ii) heavy metal resistance genes, and (iii) genes coding for the replication-stabilization system (with partitioning-active separation), multimer resolution system, and addiction toxin-antitoxin system providing stable maintenance of the plasmid in bacterial cells, for constructing bacterial strains capable of chemolithotrophic oxidation of arsenites. Such strains or the plasmid are useful in bioremediation, including the direct application in the process of bioaugmentation of the microflora of an arsenic-contaminated environments. Such strains may also be used to produce other strains capable of chemolithoautotrophic oxidation of arsenites or to improve the strains that already possess such a characteristic. The complete sequence of the plasmid pSinA of *Sinorhizobium* sp. M14 has been shown in SEQ ID NO: 1. The presented solution enables the construction of strains useful for the removal of arsenic from the contaminated environments, without the use of genetic manipulations and introduction of common risk genes (e.g. resistance to antibiotics) into circulation in the environment. By the invention, it is possible to introduce the plasmid pSinA to the cells of indigenous strains isolated from given environment and to construct stable strains capable of arsenite oxidation. Moreover, the invention allows for the conduction of a method for selection and monitoring of the strains harbouring the pSinA plasmid.

The invention therefore relates to the method for producing bacterial strains capable of chemolithotrophic arsenite oxidation, comprising the following steps: a) obtaining the recipient strain, and b) introduction of the plasmid pSinA, shown in SEQ ID NO: 1 or its functional derivative into the recipient strain. In the preferred method, step b) is carried out by:
  (i) triparental mating using a donor strain, containing the plasmid pSinA shown in SEQ ID NO: 1 or its functional derivative and a helper strain carrying a helper plasmid, or,
  (ii) biparental mating using a donor strain, containing the plasmid pSinA shown in SEQ ID NO: 1 or its functional derivative.

The preferred donor strain in this method is *Agrobacterium tumefaciens* (D10) deposited under the number KKP 2039p or *Paracoccus alcaliphilus* (C10) deposited under the number KKP 2040p.

In the preferred method for producing bacterial strains capable of chemolithotrophic arsenite oxidation in step a) of obtaining the recipient strain, a gene encoding an additional selection marker, preferably, coding for resistance to antibiotics, is additionally introduced into the recipient strain. More preferably, the gene coding for an additional selection marker is introduced on a plasmid, preferably by triparental mating with a bacterial strain harbouring the plasmid containing a gene coding for the additional selection marker and the helper strain, containing a helper plasmid.

In the preferred method for producing bacterial strains capable of chemolithotrophic arsenite oxidation the recipient is a bacterial strain isolated from the natural environment, preferably from an arsenic-contaminated environment, a particularly preferred recipient strain being a bacterial strain belonging to Alphaproteobacteria and Gammaproteobacteria.

The invention relates to the construction of strains capable of chemolithotrophic oxidation of As(III). By the use of the pSinA plasmid, its derivative or the strains: *Agrobacterium tumefaciens* KKP 2039p, *Paracoccus alcaliphilus* KKP 2040p, it is possible to construct bacterial strains capable of carrying out such reactions, starting from the strains which originally did not possess the entire gene apparatus, necessary for arsenite oxidation.

The invention provides for the construction of strains basing on bacteria isolated from various arsenic-contaminated environments, without limitation by the latitude. Due to the fact that the plasmid pSinA is capable of replication in bacterial cells belonging to Alphaproteobacteria and Gammaproteobacteria, it may be used in practically any environment. It is commonly known that the bacteria belonging to Alphaproteobacteria and Gammaproteobacteria are generally found in every environment studied.

The invention also relates to the composition, comprising the novel bacterial strain *Agrobacterium tumefaciens* KKP 2039p, *Paracoccus alcaliphilus* KKP 2040p, a novel bacterial strain capable of chemolithotrophic arsenite oxidation, produced by the method according to the invention or the plasmid pSinA shown in SEQ ID NO: 1, or its functional derivative.

In another aspect, the invention relates to the use of the novel bacterial strain *Agrobacterium tumefaciens* KKP 2039p, *Paracoccus alcaliphilus* KKP 2040p, a novel bacterial strain capable of chemolithotrophic arsenite oxidation, produced by the method according to the invention or the plasmid pSinA shown in SEQ ID NO: 1, or its functional derivative or a combination thereof, for constructing bacterial strains capable of chemolithotrophic arsenite oxidation.

Furthermore, the invention relates to the use of the novel bacterial strain *Agrobacterium tumefaciens* KKP 2039p, *Paracoccus alcaliphilus* KKP 2040p, a novel bacterial strain capable of chemolithotrophic arsenite oxidation, produced by the method according to the invention, the plasmid pSinA shown in SEQ ID NO: 1, or its functional derivative, the composition according to the invention, or a combination thereof, in the processes of biological removal of arsenic.

In the preferred embodiment, biological removal of arsenic may comprise bioremediation or biometallurgy of arsenic.

By "bioremediation" it is to be understood the conversion of harmful substances present in the environment to less toxic or completely safe metabolites, using microorganisms or higher organisms.

According to the invention, "bioaugmentation" means the introduction into the natural or degraded environment, of selected strains/a composition of microorganisms in order to increase the performance and capabilities of the course of a given process.

By "biometallurgy" it is to be understood the technology for metal recovery from metal ores and metal industry wastes.

In another aspect, the invention relates to the method of bioaugmentation of an arsenic-contaminated environment, which may comprise the step of introducing the novel bacterial strain *Agrobacterium tumefaciens* KKP 2039p, *Paracoccus alcaliphilus* KKP 2040p, a novel bacterial strain capable of chemolithotrophic arsenite oxidation, produced by the method according to the invention, or the plasmid pSinA, shown in SEQ ID NO: 1, or its functional derivative, the composition according to the invention or a combination thereof, into the arsenic contaminated environment.

The invention therefore relates to the method of introducing the plasmid pSinA directly into an environment as a part of bioaugmentation with the strain *Agrobacterium tumefaciens* KKP 2039p, *Paracoccus alcaliphilus* KKP 2040p, *Sinorhizobium* sp. M14, a bacterial strain capable of chemolithotrophic arsenite oxidation, obtained by the method according to the invention, comprising the plasmid pSinA shown in SEQ ID NO: 1, or its functional derivative, the plasmid pSinA or the composition according to the invention.

In case there is no possibility of directly constructing arsenite oxidizing strains based on the indigenous microflora, the plasmid can be introduced into the environment through the methods of bioaugmentation. A strain harbouring the plasmid pSinA or its derivative, or the composition according to the invention, is introduced into the soil and/or water contaminated with arsenic compounds and as a result of natural conjugation, the plasmid is transferred to the cells of indigenous microorganisms (autochthonous microorganisms).

The advantage of the bacterial strains comprising the plasmid pSinA, shown in SEQ ID NO: 1, or its functional derivative produced by the method according to the invention, is their stable maintenance of the plasmid introduced. Such strains are unable to get rid of it even in the absence of selection pressure i.e. in the absence of arsenic in the medium, as a result of possession of genes encoding the toxin and antitoxin system on the plasmid, providing for stable maintenance of the plasmid in bacteria. Particularly preferred in bioaugmentation, is the use of the *Agrobacterium tumefaciens* KKP 2039p strain, a derivative of *A. tumefaciens*—a bacteria recognised as environmentally safe and approved for use in soil and water environments. Moreover, an advantage of newly produced bacterial strains comprising the plasmid pSinA, like *Agrobacterium tumefaciens* KKP 2039p (D10), *Paracoccus alcaliphilus* KKP 2040p (C10), in contrast to the parental strain—*Sinorhizobium* sp. M14, is the ability to oxidize (up to ~400 mg/L) arsenites to arsenates with 100% efficiency or close to 100%, as well as the lack of accumulation of arsenic inside the cells.

The invention also relates to the method of removing or recovering arsenic through chemolithotrophic arsenite oxidation, in which the chemolithotrophic arsenite oxidation step is carried out by the novel strain *Agrobacterium tumefaciens* KKP 2039p, *Paracoccus alcaliphilus* KKP 2040p, a novel bacterial strain capable of chemolithotrophic arsenite oxidation, produced by the method according to the invention, the composition according to the invention, containing strains capable of chemolithotrophic arsenite oxidation, or a combination thereof.

In the preferred method of removing or recovering arsenic, the step of chemolithotrophic arsenite oxidation is followed by the step of arsenate removal e.g. by precipitation of the resulting arsenates in the form of an insoluble, stable precipitant or by adsorption of arsenates. For the precipitation or adsorption and effective removal of arsenates, among others, burnt lime (CaO) (Twidwell et al. 1999), calcium hydroxide $Ca(OH)_2$ (Bothe, Brown 1999) or bog iron ores may be used.

The invention also relates to the method of selection and identification of transconjugants, obtained as the result of bi- and triparental mating, based on the phenotypic characteristics encoded by the plasmid pSinA.

In another aspect, the invention relates to a plasmid comprising the nucleotide sequence corresponding to nucleotides 24376-34453 of SEQ ID NO: 1 or its functional derivative.

Such plasmid is a derivative of the plasmid pSinA, which may comprise the nucleotide sequence corresponding to nucleotides 24376-34453 of SEQ ID NO: 1, i.e. the aio module, comprising aioXSRABmoeA genes, and may be used as a plasmid or as a sequence fragment integrated into the bacterial genome for constructing strains capable of arsenite oxidation.

The invention also relates to a bacterial strain comprising a plasmid, which may comprise the nucleotide sequence corresponding to nucleotides 24376-34453 of SEQ ID NO: 1 or its functional derivative, or a bacterial strain comprising such a nucleotide sequence, comprising the fragment 24376-34453 of SEQ ID NO: 1 or its functional derivative integrated into the bacterial genome of the strain. The strains containing the nucleotide sequence corresponding to nucleotides 24376-34453 of SEQ ID NO: 1 or its functional derivative will be capable of arsenite oxidation and/or arsenate production.

The invention also relates to the use of a plasmid comprising the nucleotide sequence corresponding to nucleotides 24376-34453 of SEQ ID NO: 1 or its functional derivative, or a bacterial strain, which may comprise the nucleotide sequence corresponding to nucleotides 24376-34453 of SEQ ID NO: 1 or its functional derivative, or a bacterial strain comprising such a nucleotide sequence, comprising the fragment 24376-34453 of SEQ ID NO: 1 or its functional derivative integrated into the bacterial genome, for arsenite oxidation and arsenate production.

In a further aspect, the invention relates to a plasmid comprising the nucleotide sequence corresponding to nucleotides 43229-50772 of SEQ ID NO: 1 or its functional derivative.

Such plasmid is a derivative of the plasmid pSinA, which may comprise the nucleotide sequence corresponding to nucleotides 43229-50772 of SEQ ID NO: 1, i.e. the ars module, comprising arsR1C1C2BtrkAmsfarsHarsR2 genes, and may be used as a plasmid or as a sequence fragment integrated into the bacterial genome, for constructing strains resistant to arsenic, both As (III) and As (V), and for increasing resistance to arsenic, particularly in relation to the original strain, into which such a sequence is to be introduced.

The invention also relates to a bacterial strain comprising a plasmid comprising the nucleotide sequence corresponding to nucleotides 43229-50772 of SEQ ID NO: 1 or its functional derivative, or a bacterial strain comprising such a nucleotide sequence, comprising the fragment 43229-50772 of SEQ ID NO: 1 or its functional derivative integrated into the bacterial genome of the strain. The strains comprising the nucleotide sequence corresponding to nucleotides 43229-50772 of SEQ ID NO: 1 or its functional derivative will have an increased resistance to arsenic and/or will acquire the resistance to arsenic, both As (III) and As (V), particularly in comparison with the original strain.

The invention also relates to the use of a plasmid comprising the nucleotide sequence corresponding to nucleotides 43229-50772 of SEQ ID NO: 1 or its functional derivative, or a strain comprising a plasmid, which may comprise the nucleotide sequence corresponding to nucleotides 43229-50772 of SEQ ID NO: 1 or its functional derivative, or a bacterial strain comprising such a nucleotide sequence, comprising the fragment 43229-50772 of SEQ ID NO: 1 or its functional derivative integrated into the bacterial genome, for producing a strain with an increased resistance to arsenic, both As (III) and As (V), particularly in comparison with the original strain.

The following examples are presented merely to illustrate the invention and to clarify its various aspects, but are not intended to be limitative, and should not be equated with all its scope, which is defined in the appended claims.

In the following examples, unless it was otherwise indicated, standard materials and methods described in Sambrook and Russell. 2001. Molecular cloning: A laboratory manual. Cold Spring Harbor Laboratory Press, New York. were used, or the manufacturers' instructions for specific materials and methods were followed.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Characteristics of Plasmid pSinA and Determination of Its Complete Sequence

Plasmid pSinA, of the size of 109 kbp, was isolated from the *Sinorhizobium* sp. M14 strain (Drewniak et al., 2008, Drewniak et al. 2010). In order to sequence the plasmid, plasmid pSinA was isolated from 200 ml of overnight culture of *Sinorhizobium* sp. M14 by alkaline lysis method. Plasmid pSinA was sequenced by pyrosequencing method, using "shotgun" strategy on the GS FLX Titanium (454) sequencer (in the Oligo Pl. centre). For the construction of DNA library, approx. 5 μg of pSinA DNA was used and reagent kits provided by the manufacturer were applied (GS FLX Titanium Library Preparation Kit, Roche). The constructed library was sequenced and assembled using the software from the Newbler de novo assembler package (Roche). The obtained sequences were then assembled into contigs using Seqman software from Lasergene package (DNAStar) Annotation of the plasmid (identification of the open reading frames and determination of their potential functions) were performed using Artemis program and BLAST programs (from the NCBI database).

Sequencing of the plasmid pSinA showed that it is a DNA particle of the size of 108 938 bp and the GC-content of 59.5%. It may comprise 103 open reading frames (ORF), which constitute 89% of the sequence of the plasmid. Table 1, below, features a detailed description of the identified ORFs within SEQ ID NO: 1.

TABLE 1

Determination of the potential coding sequences of the plasmid pSinA in reference to SEQ ID NO: 1.

| ORF No | Coding sequence (start-stop codon)* | Protein size (aa) | Predicted protein function | The greatest similarity (BLASTP program) | | |
|---|---|---|---|---|---|---|
| | | | | Identity (%) | Organism | GenBank number |
| 1 | 189-1463 | 424 | Replication initiation protein (RepA) | 90 (380/424) | *Agrobacterium rhizogenes* (pRi1724) | NP_066713 |

TABLE 1-continued

Determination of the potential coding sequences of the plasmid pSinA in reference to SEQ ID NO: 1.

| ORF No | Coding sequence (start-stop codon)* | Protein size (aa) | Predicted protein function | Identity (%) | Organism | GenBank number |
|---|---|---|---|---|---|---|
| 2 | 1567-2571 | 334 | Replication initiation protein (RepB) | 71 (236/335) | *Agrobacterium rhizogenes* (pRi1724) | NP_066714 |
| 3 | 2740-3951 | 403 | Replication initiation protein (RepC) | 73 (288/399) | *Rhizobium etli* CFN 42 (p42a) | YP_471771 |
| 4 | 4297-5457c | 386 | Integrase family protein (Cre-like recombinases) | 82 (305/372) | *Rhizobium leguminosarum* bv. *trifolii* WSM2304(pRL8) | YP_770909 |
| 5 | 5535-5813 | 92 | Prevent-host-death family protein | 84 (77/92) | *Rhizobium leguminosarum* bv. *trifolii* WSM2304(pRL8) | YP_002279248 |
| 6 | 5800-6231 | 143 | Hypothetical protein (PemK-like protein) | 75 (107/143) | *Brucella ovis* ATCC 25840 | YP_001257527 |
| 7 | 6467-7597 | 376 | Protein of unknown function (DUF1612) | 67 (253/380) | *Agrobacterium radiobacter* K84 | YP_002546559 |
| 8 | 7688-8281 | 197 | Hypothetical protein | 97 (179/185) | *Agrobacterium tumefaciens* (pTi) | NP_053264 |
| 9 | 8345-8731 | 128 | Predicted nucleic acid-binding protein (PilT protein-like protein) | 91 (100/111) | *Agrobacterium tumefaciens* (pTi) | NP_053265 |
| 10 | 8768-12582c | 1271 | Putative protein involved in cell division and chromosome partitioning | 28 (326/1181) | *Rhizobium etli* CIAT 652 | YP_001984284 |
| 11 | 12767-13393 | 208 | Hypothetical protein | 85 (177/209) | *Rhodopseudomonas palustris* BisB18 | YP_532912 |
| 12 | 13414-14253 | 279 | Hypothetical protein | 34 (87/256) | *Bacillus thuringiensis* serovar huazhongensis BGSC 4BD1 | ZP_04087111 |
| 13 | 14474-16219 | 581 | Predicted ATPase (COG5293) | 45 (258/585) | *Nostoc* sp. PCC 7120 | NP_485895 |
| 14 | 16235-17032 | 265 | Hypothetical protein (transposon) | 80 (211/265) | *Pseudomonas aeruginosa* | ACD39332 |
| 15 | 17092-17913 | 273 | Hypothetical protein | 49 (97/202) | *Agrobacterium tumefaciens* (pTi) | NP_059784 |
| 16 | 18097-21072 | 991 | Hypothetical protein (ATPase involved in DNA repair) | 86 (837/978) | *Labrenzia alexandrii* DFL-11 | ZP_05114452 |
| 17 | 21082-21768 | 228 | Putative siderophore biosynthesis-associated protein | 72 (131/182) | *Methylobacterium extorquens* DM4 | YP_003066102 |
| 18 | 21761-22699 | 312 | Hypothetical protein | 84 (244/293) | *Methylobacterium extorquens* DM4 | YP_003066101 |
| 19 | 22735-23241 | 168 | Hypothetical protein | 68 (108/161) | *Xanthobacter autotrophicus* Py2 | YP_001415141 |
| 20 | 23283-23777 | 164 | Hypothetical protein | 92 (150/164) | *Oceanicola granulosus* HTCC2516 | ZP_01157550 |
| 21 | 23783-24139c | 118 | Hypothetical protein | 96 (113/118) | *Rhizobium etli* CIAT 894 | ZP_03526252 |
| 22 | 24660-25877c | 405 | Molybdenum-biosynthesis protein (MoeA) | 84 (338/404) | arsenite-oxidising bacterium NT-26 | ABC18312 |
| 23 | 26035-26418c | 127 | c-type cytochrome c552 | 97 (122/127) | *Agrobacterium tumefaciens* | ABB51926 |
| 24 | 26508-29045c | 845 | large subunit of Arsenite oxidase AioB (previously AoxB)) | 99 (831/845) | *Agrobacterium tumefaciens* | ABB51928 |
| 25 | 29058-29585c | 175 | Small subunit of Arsenite oxidase (AioA (previously AoxA))) | 98 (171/175) | *Agrobacterium tumefaciens* | ABB51929 |
| 26 | 29723-31051c | 442 | Putative transcriptional regulator (AioR (previously AoxR))) | 97 (428/442) | *Agrobacterium tumefaciens* | ABB51925 |
| 27 | 31041-32507c | 488 | Putative sensor histidine kinase (AioS(previously AoxS))) | 97 (470/488) | *Agrobacterium tumefaciens* | ABB51924 |
| 28 | 32504-33424c | 306 | Phosphate/phosphonate ABC transporter (AioX (previously PhnD) | 57 (167/295) | *Xanthobacter autotrophicus* Py2 | YP_001418827 |
| 29 | 33604-34296c | 230 | Phosphate regulon transcriptional regulatory protein (PhoB) | 83 (187/227) | *Agrobacterium vitis* S4 | YP_002548344 |
| 30 | 34661-35698 | 345 | Phosphate-binding protein (PstS) | 75 (229/306) | *Alcaligenes faecalis* | AAQ19844 |
| 31 | 35756-36679 | 307 | Phosphate ABC transporter, inner membrane subunit (PstC) | 75 (227/305) | *Alcaligenes faecalis* | AAQ19845 |
| 32 | 36679-37626 | 315 | Phosphate ABC transporter, inner membrane subunit (PstA) | 70 (212/303) | *Alcaligenes faecalis* | AAS45094 |
| 33 | 37644-38486 | 280 | phosphate ABC transporter, ATPase subunit (PstB) | 75 (195/262) | *Alcaligenes faecalis* | AAS45095 |
| 34 | 38502-39179 | 231 | Phosphate transport system regulatory protein (PhoU) | 49 (108/224) | *Pseudovibrio* sp. JE062 | ZP_05085295 |
| 35 | 39203-39865 | 220 | Phosphate regulon transcriptional regulatory protein (PhoB) | 40 (88/225) | *Pseudovibrio* sp. JE062 | ZP_05085350 |
| 36 | 39872-40963c | 273 | Bifunctional protein: N-terminal transcriptional regulator (ArsR) and C-terminal arsenate reductase (ArsC) | 47 (130/280) | *Nitrobacter hamburgensis* X14 (pPB12) | YP_571847 |
| 37 | 40850-41803 | 317 | Phosphate/phosphonate ABC transporter (PhnD) | 78 (232/300) | *Xanthobacter autotrophicus* Py2 | YP_001418843 |
| 38 | 41877-42716 | 279 | Phosphonate ABC transporter, ATP-binding protein (PhnC) | 76 (190/251) | *Roseobacter* sp. AzwK-3b | ZP_01904969 |
| 39 | 42716-43531 | 271 | Phosphonate uptake ABC type transporter (PhnE) | 75 (197/266) | *Fulvimarina pelagi* HTCC2506 | ZP_01438481 |
| 40 | 43531-44349 | 272 | Phosphonate uptake ABC type transporter (PhnE) | 70 (187/268) | *Vibrio metschnikovii* CIP 69.14 | ZP_05881311 |
| 41 | 44496-44855 | 119 | ArsR family transcriptional regulator | 72 (80/112) | *Rhizobium etli* CIAT 894 | ZP_03530366 |
| 42 | 45085-45612 | 175 | Tyrosine arsenate reductase (ArsC) | 89 (147/166) | *Rhizobium etli* CIAT 894 | ZP_03530368 |
| 43 | 45717-46151 | 144 | Arsenate reductase (ArsC) | 80 (114/143) | *Sinorhizobium medicae* WSM419 | YP_001313767 |

TABLE 1-continued

Determination of the potential coding sequences of the plasmid pSinA in reference to SEQ ID NO: 1.

| ORF No | Coding sequence (start-stop codon)* | Protein size (aa) | Predicted protein function | The greatest similarity (BLASTP program) | | |
|---|---|---|---|---|---|---|
| | | | | Identity (%) | Organism | GenBank number |
| 44 | 46237-47307 | 356 | Arsenite efflux transporter (AsrB) | 89 (314/356) | *Sinorhizobium medicae* WSM419 | YP_001313766 |
| 45 | 47324-48367 | 347 | FAD-dependent pyridine nucleotide-disulphide oxidoreductase (TrkA) | 62 (206/336) | *Burkholderia vietnamiensis* G4 | YP_001114753 |
| 46 | 48317-49537c | 406 | Major facilitator superfamily (MFS_1) protein | 68 (272/404) | *Rhizobium leguminosarum* bv. *trifolii* WSM1325 | YP_002976231 |
| 47 | 49534-50241c | 235 | NADPH-dependent FMN reductase (ArsH) | 84 (196/235) | *Rhizobium leguminosarum* bv. *viciae* 3841 | YP_768473 |
| 48 | 50290-50622c | 110 | ArsR family transcriptional regulator | 65 (63/97) | *Agrobacterium vitis* S4 | YP_002547788 |
| 49 | 50781-51596c | 271 | Putative universal stress response protein (UpsA) | 34 (92/271) | *Rhizobium etli* CFN 42 | YP_472650 |
| 50 | 51610-52875c | 421 | Putative phosphopyruvate hydratase (enolase) | 70 (291/421) | *Methylococcus capsulatus* str. Bath | YP_114366 |
| 51 | 52931-53116c | 61 | Hypothetical protein | 51 (30/59) | *Rhizobium leguminosarum* bv. *trifolii* WSM2304 | YP_002279234 |
| 52 | 53176-53514c | 112 | Hypothetical protein | 92 (94/103) | *Rhizobium etli* IE4771 | ZP_03517489 |
| 53 | 53752-55569c | 605 | ClC sycA-like chloride channel protein | 80 (343/433) | *Agrobacterium vitis* S4 | YP_002548815 |
| 54 | 55761-56153c | 130 | Hypothetical protein | 48 (30/63) | *Burkholderia phytofirmans* PsJN | YP_001893937 |
| 55 | 56215-56706 | 163 | Putative Co/Zn/Cd efflux system component (CzcD) | 71 (109/155) | *Methylobacterium nodulans* ORS 2060 | YP_002497120 |
| 56 | 56763-57551c | 262 | Predicted permease (DUF81) | 76 (177/233) | *Methylobacterium extorquens* DM4 | YP_003068171 |
| 57 | 57710-58918c | 402 | pH-dependent sodium/proton antiporter | 74 (287/392) | *Rhizobium etli* CFN 42 | YP_468132 |
| 58 | 59238-59546 | 102 | Hypothetical protein (probable helicase) | 50 (38/77) | *Agrobacterium vitis* S4 | YP_002542648 |
| 59 | 59529-59969c | 146 | MerR family transcriptional regulator | 100 (146/146) | *Ochrobactrum anthropi* ATCC 49188 | YP_001371693 |
| 60 | 60055-60480 | 141 | Mercuric transporter (MerT) | 100 (141/141) | *Ochrobactrum anthropi* ATCC 49188 | YP_001371694 |
| 61 | 60501-60794 | 97 | Mercuric transport protein periplasmic component (MerP) | 100 (97/97) | *Ochrobactrum anthropi* ATCC 49188 | YP_001371695 |
| 62 | 61040-63277 | 745 | Mercuric reductase (MerA) | 100 (745/745) | *Ochrobactrum anthropi* ATCC 49188 | YP_001371697 |
| 63 | 63661-65805c | 714 | Hypothetical protein (putative phage integrase) | 99 (713/714) | *Ochrobactrum anthropi* ATCC 49188 | YP_001371699 |
| 64 | 65802-67610c | 602 | Hypothetical protein (putative phage integrase) | 100 (602/602) | *Ochrobactrum anthropi* ATCC 49188 | YP_001371700 |
| 65 | 67610-69049c | 479 | Putative XerD integrase | 100 (479/479) | *Ochrobactrum anthropi* ATCC 49188 | YP_001371701 |
| 66 | 69480-70514 | 344 | Putative RecA relaxase | 62 (209/341) | *Rhizobium etli* CFN 42 | YP_471728 |
| 67 | 70577-71182 | 201 | Protein of unknown function (DUF1419) | 73 (145/201) | *Agrobacterium rhizogenes* | NP_066672 |
| 68 | 71278-71571c | 97 | Hypothetical protein | 37 (35/95) | *Agrobacterium tumefaciens* | NP_053284 |
| 69 | 71747-76921 | 1724 | S-adenosylmethionine-dependent methyltransferase | 86 (1445/1687) | *Rhizobium leguminosarum* bv. *viciae* 3841 | YP_770997 |
| 70 | 77344-79101 | 585 | Partitioning protein ParBC | 71 (408/578) | *Agrobacterium rhizogenes* | YP_001961038 |
| 71 | 79098-79991 | 297 | Hypothetical protein | 61 (171/282) | *Agrobacterium rhizogenes* | YP_001961040 |
| 72 | 79998-80299 | 103 | Hypothetical protein | 43 (38/89) | *Ochrobactrum anthropi* ATCC 49188 | YP_001373171 |
| 73 | 80356-80589 | 77 | Hypothetical protein | 68 (27/40) | *Rhizobium etli* IE4771 | ZP_03514174 |
| 74 | 80683-81270 | 195 | Hypothetical protein | 83 (161/194) | *Agrobacterium rhizogenes* | YP_001961043 |
| 75 | 81548-82471 | 307 | Conjugal transfer antirestriction protein (ArdC) | 82 (244/300) | *Rhizobium leguminosarum* bv. *viciae* 3841 | YP_771003 |
| 76 | 82799-83125 | 108 | Hypothetical protein | | No significant similarities found | |
| 77 | 83142-83450 | 102 | Protein of unknown function (DUF736) | 99 (100/102) | *Sinorhizobium meliloti* | YP_001965632 |
| 78 | 83600-83938 | 112 | Hypothetical protein | 61 (69/114) | *Agrobacterium vitis* S4 | YP_002551439 |
| 79 | 84033-84302 | 89 | Hypothetical protein | | No significant similarities found | |
| 80 | 84441-84893c | 150 | Putative nuclease | 64 (96/150) | *Rhizobium leguminosarum* bv. *viciae* 3841 | YP_771010 |
| 81 | 85731-87668c | 645 | Conjugal transfer coupling protein (TraG) | 82 (508/627) | *Rhizobium etli* CFN 42 | YP_471745 |
| 82 | 87655-87870c | 71 | Conjugal transfer protein (TraD) | 80 (56/70) | *Rhizobium leguminosarum* bv. *viciae* 3841 | YP_771013 |
| 83 | 87875-88171c | 98 | Conjugal transfer protein (TraC) | 69 (67/98) | *Agrobacterium tumefaciens* | BAB47248 |
| 84 | 88422-91745 | 1107 | Dtr system oriT relaxase (TraA) | 78 (855/1109) | *Agrobacterium tumefaciens* | BAB47249 |
| 85 | 91742-92308 | 188 | Conjugal transfer pilin processing protease (TraF) | 55 (102/188) | *Rhizobium leguminosarum* bv. *viciae* 3841 | YP_771016 |
| 86 | 92298-93464 | 388 | Conjugal transfer protein (TraB) | 62 (239/388) | *Rhizobium* sp. NGR234 | NP_443826 |
| 87 | 93482-94093 | 203 | Conjugal transfer protein (TraH) | 71 (144/205) | *Rhizobium leguminosarum* bv. *viciae* 3841 | YP_770822 |

TABLE 1-continued

Determination of the potential coding sequences of the plasmid pSinA in reference to SEQ ID NO: 1.

| ORF No | Coding sequence (start-stop codon)* | Protein size (aa) | Predicted protein function | The greatest similarity (BLASTP program) | | |
|---|---|---|---|---|---|---|
| | | | | Identity (%) | Organism | GenBank number |
| 88 | 94126-94746c | 206 | Hypothetical protein | 71 (144/205) | Rhizobium leguminosarum bv. viciae 3841 | YP_770822 |
| 89 | 94747-95502c | 251 | Hypothetical protein | 65 (165/255) | Rhodopseudomonas palustris DX-1 | ZP_06357667 |
| 90 | 96193-96897 | 234 | Putative LuxR-type transcriptional regulator protein (TraR) | 51 (119/234) | Sinorhizobium meliloti | YP_001965652 |
| 91 | 96912-97211c | 99 | TraR antiactivator (TraM) | 52 (51/99) | Agrobacterium tumefaciens | NP_053353 |
| 92 | 97764-98483 | 239 | AHL-dependent transcriptional regulator similar to LuxR | 59 (134/231) | Rhizobium leguminosarum | AF210630_2 |
| 93 | 98601-99263 | 220 | Conjugation factor synthetase (TraI) | 62 (136/221) | Rhizobium etli Brasil 5 | ZP_03504772 |
| 94 | 99303-100598c | 431 | Conjugal transfer protein (TrbI) | 76 (328/432) | Sinorhizobium meliloti SM11 | YP_001965654 |
| 95 | 100611-101054c | 147 | Conjugal transfer protein (TrbH) | 70 (100/143) | Rhizobium leguminosarum bv. viciae 3841 | YP_771025 |
| 96 | 101058-101888c | 276 | Conjugal transfer protein (TrbG) | 86 (237/276) | Sinorhizobium meliloti SM11 | YP_001965656 |
| 97 | 101904-102566c | 220 | Conjugal transfer protein (TrbF) | 92 (201/220) | Rhizobium leguminosarum bv. viciae 3841 | YP_771027 |
| 98 | 102588-103769c | 393 | Conjugal transfer protein (TrbL) | 87 (327/380) | Rhizobium etli IE4771 | ZP_03519561 |
| 99 | 103944-104747c | 267 | Conjugal transfer/entry exclusion protein (TrbJ) | 87 (205/238) | Rhizobium leguminosarum bv. viciae | AAO21104 |
| 100 | 104740-107175c | 811 | Conjugal transfer protein (TrbE) | 89 (719/809) | Rhizobium leguminosarum bv. viciae 3841 | YP_771030 |
| 101 | 107186-107485c | 99 | Conjugal transfer protein (TrbD) | 78 (77/99) | Rhizobium etli CFN 42 | YP_471765 |
| 102 | 107478-107870c | 130 | Conjugal transfer protein (TrbC) | 74 (97/132) | Rhizobium leguminosarum bv. viciae 3841 | YP_771032 |
| 103 | 107860-108825c | 321 | Conjugal transfer protein (TrbB) | 90 (288/321) | Sinorhizobium meliloti SM11 | YP_001965665 |

*The numbers in the coding sequence correspond to the nucleotide numbers in SEQ ID NO: 1.

Figure 1:
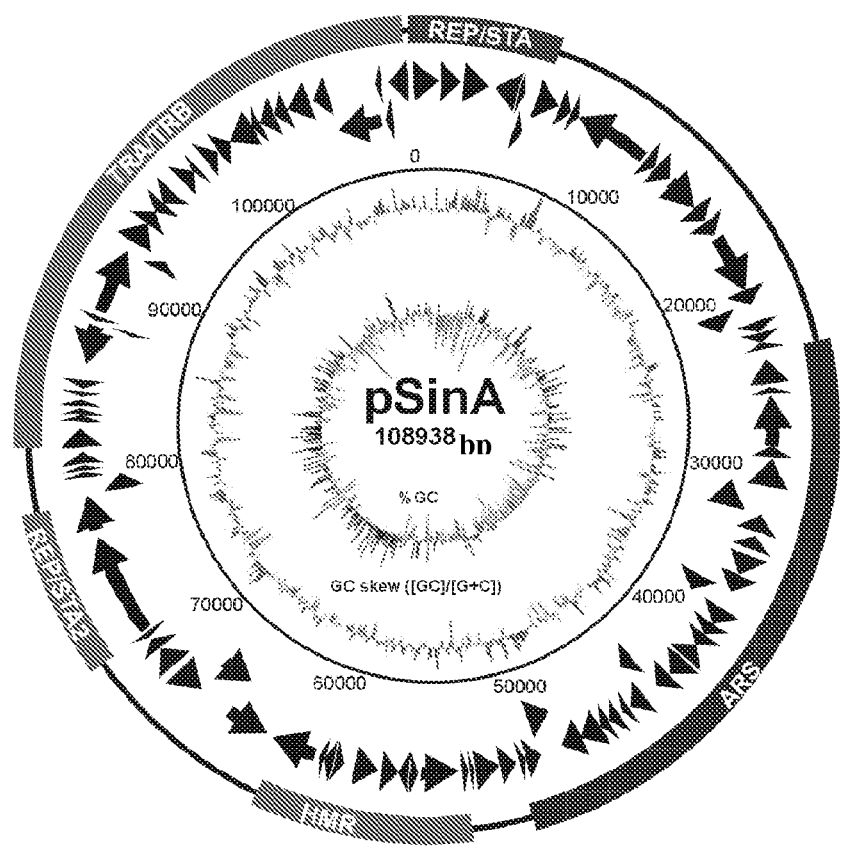
FIG. 1. Shows the genetic organization of the plasmid pSinA. In the diagram, different modules of the plasmid backbone and phenotypic regions have been described: REP/STA and REP/STA2—replication-stabilization modules, TRA/TRB—conjugation module, ARS—arsenic metabolism module, HMR—arsenic resistance module, and TOXIN/ANTITOXIN module. RepABC system (replication and partitioning system—active separation) MRS system (multimer resolution system) and PHD-DOC system (addiction system—toxin/antitoxin) are located within the REP/STA module.

The determined genetic organization of the plasmid pSinA has been presented in FIG. 1. The obtained, complete sequence of plasmid pSinA has been shown in SEQ ID NO: 1.

Example 2

Construction of the Agrobacterium tumefaciens and Paracoccus alcaliphilus Strains Capable of Chemolithotrophic Arsenite Oxidation In order to demonstrate that the plasmid pSinA can be used for constructing strains capable of arsenite oxidation, the plasmid pSinA was introduced into two strains belonging to Alphaproteobacteria. For the construction, two strains have been selected: Agrobacterium tumefaciens LBA288 and Paracoccus alcaliphilus JCM7364R, incapable of arsenite oxidation and susceptible to As (III) (1 mM of sodium arsenite inhibits the growth of both strains). As a method for introducing plasmid DNA, bi- and triparental mating, described in Sambrook and Russel (2001), was used.

In order to allow the introduction of the pSinA plasmid into the selected strains, one must know their phenotypic characteristics that can be used as markers for selection, enabling the elimination of the cells of the plasmid donor. In case none of the phenotypic traits encoded by the recipient strain can be used, it should be appropriately modified (example 2A) or an appropriate method for identification of transconjugants should be applied (example 2B).

Example 2A

Construction of Strains Resistant to Tetracycline

The A. tumefaciens LBA288 strain does not carry any phenotypic characteristics that enable the use of an appropriate selection pressure to eliminate the cells of the plasmid donor. In accordance with the above, in order to establish an adequate method for selection, plasmid pBBR1MCS3 (Kovach et al., 1995), carrying a gene for tetracycline resistance, was introduced into its cells. The Sinorhizobium sp. M14 strain is susceptible to tetracycline, which allows for the removal of the cells of the donor strain in conjugation. The plasmid pBBR1MCS3 (introduced into Escherichia coli TG1 cells beforehand) was introduced into the cells of the A. tumefaciens LBA288 strain, by triparental mating, in which the pRK2013 helper plasmid (Ditta et al. 1980) (introduced into Escherichia coli TG1 cells beforehand) was used. The helper plasmid facilitates conjugation in case of strains, carrying genes responsible for the transfer only, and not for mobilization to the transfer. The conjugation was carried out according to Sambrook and Russel (2001), and for the selection of transconjugants, LB medium supplemented with tetracycline (20 µg/ml) (eliminating the cells of the recipient) and rifampicin (50 µg/ml) (eliminating the cells of the donor strain and of the strain harbouring the helper plasmid—in both cases Escherichia coli TG1) was used. The prepared donor cultures (E. coli TG1 with the plasmid pBBR1MCS3), the helper strain (E. coli TG1 with the plasmid pRK2013) and the recipient (A. tumefaciens LBA288) were mixed in a ratio 1:1:2, and then 100 µl of the mixture were plated on LB medium. After 24-hour incubation at 30° C., bacterial colonies were washed off the surface of the petri dish with 2 ml of saline solution, and appropriate dilutions ($10^0$-$10^{-3}$) were plated on selective LB medium, supplemented with tetracycline and rifampicin, and then incubated for 48 h at 30° C. As a result of conjugation, transconjugants, derivatives of A. tumefaciens LBA288 harbouring the plasmid pBBR1MCS3, were obtained. For further analysis, one strain, named A. tumefaciens PBBR-Tc, was selected. The obtained strain was then used as the recipient strain in conjugation with Sinorhizobium sp. M14 strain.

Introduction of the Plasmid pSinA into the Cells of Strains Resistant to Tetracycline. Production of *A. tumefaciens* D10 Strain (Deposited as KKP2039p)

In order to introduce the plasmid pSinA into the cells of the *A. tumefaciens* PBBR-Tc strain, triparental mating was applied again (with the use of the pRK2013 helper plasmid, introduced into *E. coli* TG1 cells) and additionally, biparental mating. In both of these types of conjugation, the *Sinorhizobium* sp. M14 strain was used as the donor, capable of arsenite oxidation and resistant to As (III) (up to 20 mM) and susceptible to tetracycline. For the selection of transconjugants, LB medium (Sambrook and Russel, 2001), supplemented with 2.5 mM As(III) and tetracycline (20 µg/ml) was used. The prepared cultures of the donor (*Sinorhizobium* sp. M14 with the plasmid pSinA), the helper strain (*E. coli* TG1 with the plasmid pRK2013) (in case of triparental mating) and the recipient (*A. tumefaciens* PBBR-Tc) were mixed in a ratio 1:1:2, and then 100 µl of the mixture were plated on LB medium (Sambrook and Russel, 2001). After 24-hour incubation at 30° C., bacterial colonies were washed off the surface of the petri dish with 2 ml of saline solution, and dilutions ($10^0$-$10^{-3}$) were plated on selective LB medium, supplemented with tetracycline and sodium arsenite, and then incubated for 48 h at 30° C. Potential transconjugants were subjected to the following analyses:

1. physiological analysis to determine the ability to oxidize As (III) in modified MSM medium (Drewniak et al., 2008)—in order to determine the ability to oxidize As (III), potential transconjugant strains were cultivated in MSM medium supplemented with arsenites (the sole energy source) at 30° C. After 5 days of incubation under aerobic conditions, 500 µl of the culture were collected and added to 500 µl of 0.1 M solution of silver nitrate. The result of the reaction between $AgNO_3$ and As (III) or As (V) is the formation of a coloured precipitate. A brown precipitate indicates the presence of $Ag_3AsO_4$ (silver orthoarsenate), while a yellow precipitate indicates the presence of $Ag_3AsO_3$ (silver arsenite). In case of testing for the ability to oxidise arsenites, the presence of a brown precipitate indicates that As (III) was oxidised to As (V).

2. DNA-DNA hybridization (Southern blot)—in order to identify plasmid pSinA genes in the genomes of potential transconjugants. Fragments of the genes located on the plasmid pSinA, amplified by PCR (using the primers shown in Table 2) and labelled with digoxigenin were used as probes. Hybridization was carried out against the plasmid DNA isolated from transconjugants, obtained by alkaline lysis and visualised by DNA electrophoresis.

3. PCR analyses—in order to identify plasmid pSinA genes in the genomes of potential transconjugants, PCR was performed using primers, described in Table 2.

4. visualization of plasmids of potential transconjugants obtained by alkaline lysis and visualized by DNA electrophoresis.

For the hybridization analysis and PCR analysis, genes and primers presented in Table 2 were used.

TABLE 2

Sequences of the primers used in PCR amplification of plasmid pSinA genes and chromosomal 16S rRNA genes

| Gene name | Primer | Sequence | Position in the genome of plasmid pSinA, in reference to SEQ ID NO: 1 |
|---|---|---|---|
| aoxB | aoxBF | CCACTTCTGCATCGTCGGCT | 26701-26721 |
|  | aoxBR | GTCGGTGTCGGATAGGCCAT | 28954-28974 |
| repA | repAF | CGTGCGCTATCTTCAGACGG | 188-208 |
|  | repAR | GCTTGAGTTCTTCGTAGTCC | 1709-1729 |
| traI | traIF | GTGCTCATCGGAGTGAATGG | 98200-98220 |
|  | traIR | GACATCAAGGATCTCGGCTA | 99912-99932 |
| orf12 | 12F | GCAATCGGTCTCACAAGAGG | 12122-12142 |
|  | 12R | AAGGCGCACATCAGCTCGAA | 14139-14159 |
| 16SrRNA | 27F | AGAGTTTGATCMTGGCTCAG | Universal primers for amplification of bacterial 16S rRNA genes |
|  | 1492R | GGTTACCTTGTTACGACTT |  |

Figure 2C:
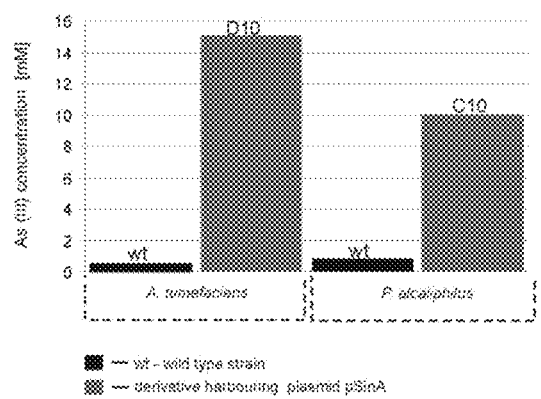

In both types of conjugation (bi- and tri-parental), transconjugants harbouring the plasmid pSinA were obtained. For further analysis, the *A. tumefaciens* D10 strain from biparental mating (deposited as KKP2039p) was chosen. This strain was capable of arsenite oxidation and of using them as an electron donor (energy source) (FIG. 2A). In addition, this strain has increased its tolerance to As(III) (FIG. 2C). To verify whether the constructed strain stably maintains the plasmid, a series of passages (4-6 times) in media without selection pressure was performed. The obtained results showed that the constructed *A. tumefaciens* D10 strain stably maintains the plasmid pSinA. After about 60 generations of growth in conditions without selection pressure (without arsenic) no plasmid-less cells were observed.

Example 2B

In case we do not want to apply selection pressure associated with the use of antibiotics, there is a possibility of indirect selection of transconjugants harbouring plasmid pSinA or its derivative. For this purpose, bi- or triparental mating is carried out using minimal MSM medium as the selection medium, and sodium arsenite as the sole compound for the selection of potential transconjugants. Subsequently, an identification of approx. 100-200 randomly selected colonies of potential transconjugants is performed. Identification of the appropriate strains is performed using the analyses described in Example 2A.

Example 3

Construction of the *Paracoccus alcaliphilus* Strain, Capable of Chemolithotrophic Arsenite Oxidation The strains into which the plasmid pSinA was introduced (e.g. *A. tumefaciens* deposited as KKP2039p (D10)) can also be used to construct further strains capable of arsenite oxidation. In order to confirm this assumption, the *A. tumefaciens* D10 strain was used for the transfer of the plasmid pSinA to the *Paracoccus alcaliphilus* JCM7364R strain (Bartosik et al., 2002). This strain is incapable of arsenite oxidation and is susceptible to As (III) (1 mM of sodium arsenite inhibits its growth). As the method for introducing plasmid DNA, biparental mating, described in Sambrook and Russel (2001) was used.

Construction of the *P. alcaliphilus* Strain, Resistant to Kanamycin

Because the *P. alcaliphilus* JCM7364R strain carries no phenotypic characteristics that allow for the application of an adequate selection pressure to eliminate the cells of the plasmid donor, genetic manipulations were performed, involving introduction of the plasmid pBBR1MCS2 (Kovach et al., 1995), carrying resistance to kanamycin, into the cells of the *P. alcaliphilus* JCM7364R strain. The *A. tumefaciens* KKP2039p (D10) strain that was used as the donor in conjugation, is susceptible to kanamycin, which allowed for the removal of the cells of the donor strain in conjugation.

The plasmid pBBR1MCS2 introduced beforehand, into *Escherichia coli* TG1 cells was introduced into the cells of the *P. alcaliphilus* JCM7364 strain using triparental mating, in which the pRK2013 helper plasmid (Ditta et al. 1980) (introduced into *Escherichia coli* TG1 cells, beforehand) was used. Conjugation was carried out according to Sambrook and Russel (2001), and LB medium supplemented with kanamycin (50 µg/ml), which eliminates the cells of the recipient, and with rifampicin (50 µg/ml), which allows for the elimination of the cells of the donor strain and of the strain harbouring the helper plasmid—in both cases *Escherichia coli* TG1, was used for the selection of transconjugants. The prepared donor cultures (*E. coli* TG1 with the pBBR1MCS2 plasmid), the helper strain (*E. coli* TG1 with the pRK2013 plasmid) and the recipient (*P. alcaliphilus* JCM7364R) were mixed in a ratio 1:1:2, and then 100 µl of the mixture were plated on LB medium (Sambrook and Russel, 2001). After 24-hour incubation at 30° C., bacterial colonies were washed off the surface of the petri dish with 2 ml of saline solution, and appropriate dilutions ($10^0$-$10^{-3}$) were plated on selective LB medium, supplemented with kanamycin and rifampicin, and then incubated for 48 h at 30° C. As a result of conjugation, transconjugants, derivatives of *P. alcaliphilus* JCM7364R harbouring the plasmid pBBR1MCS2, were obtained. For further analysis, one strain, named *P. alcaliphilus* PBBR-Km, was selected. The obtained strain was then used as the recipient strain in conjugation with *A. tumefaciens* D10 (deposited as KKP 2039p).

Introduction of the Plasmid pSinA of *A. tumefaciens* KKP 2039p (D10) to *P. alcaliphilus* PBBR-Km. Production of the *Paracoccus alcaliphilus* KKP 2040p (C 10) Strain.

In order to introduce the pSinA plasmid into the cells of the constructed *P. alcaliphilus* PBBR-Km strain, triparental mating was applied (using the pRK2013 helper plasmid, introduced into *E. coli* TG1 cells). The *A. tumefaciens* D10 strain, capable of arsenite oxidation and resistant to As (III) (up to 15 mM) and susceptible to kanamycin was used as the donor. For the selection of transconjugants, LB medium supplemented with 2.5 mM As(III) and kanamycin (50 µg/ml) was used. The prepared cultures of the donor (*A. tumefaciens* D10 with the plasmid pSinA), the helper strain (*E. coli* TG1 with the pRK2013 plasmid), and the recipient (*P. alcaliphilus* PBBR-Km) were mixed in a ratio 1:1:2, and then 100 µl of the mixture were plated on LB medium. After 24-hour incubation at 30° C., bacterial colonies were washed off the surface of the petri dish with 2 ml of saline solution, and dilutions ($10^0$-$10^{-3}$) were plated on selective LB medium, supplemented with kanamycin and sodium arsenite, and then incubated for 48 h at 30° C. Potential transconjugants were subjected to analyses analogous to those in Example 2A.

As a result of conjugation, *P. alcaliphilus* transconjugants harbouring the plasmid pSinA were obtained. For further analysis, the *P. alcaliphilus* C10 strain was chosen. This strain acquired the ability to oxidise arsenites and to use them as an electron donor (energy source) (FIG. 2B). In addition, this strain has increased its tolerance to As(III) (FIG. 2C). To verify whether the constructed strain stably maintains the plasmid, a series of passages (4-6 times) in media without selection pressure was performed. The obtained results showed that the constructed *P. alcaliphilus* C10 strain stably maintains the plasmid pSinA. After about 60 generations of growth in conditions without selection pressure (without arsenic) no plasmid-less cells were observed.

Example 4

Introduction of the Plasmid to the Cells of Indigenous Microflora of Arsenic Contaminated Environments by Means of Bioaugmentation with *Sinorhizobium* sp. M14 Strain In order to demonstrate that the plasmid pSinA can be used in bioaugmentation of indigenous microflora of arsenic contaminated environments, an experiment was conducted on two different soil samples coming from the gold mine area in Zloty Stok. The soil designated as ZP (I) came from the vicinity of the Zloty Potok and contained from 1149.3 to 1241 mg of As/kg of soil. The soil designated as PT (II) came from the vicinity of the Potok Trujaca and contained from 528 to 532 mg of As/kg of soil. The experiment was carried out for 60 days in microcosms, supplemented with 100 g of non-sterile soil, to which the *Sinorhizobium* sp. M14 strain was added. The soil not enriched with the M14 strain was used as the control. At the beginning of the experiment, and every 15 days, samples of soil were collected, and the bacteria were plated on solid MSM medium (Drewniak et al., 2008) with 5 mM sodium arsenite. The grown cultures were passaged to LB medium with 5 mM As(III) and to liquid MSM medium with 5 mM of As(III). In order to verify whether the grown colonies (potential transconjugants) harbour the plasmid pSinA, the following analyses were performed: (i) physiological analysis to determine the ability to oxidize As(III) on the modified MSM medium; (ii) DNA-DNA hybridization (Southern blot) in order to identify pSinA plasmid genes in the genomes of potential transconjugants; (iii) PCR analyses, in order to identify plasmid pSinA genes in the genomes of potential transconjugants; (iv) visualization of plasmids and megaplasmids of potential transconjugants. For the hybridization analysis and PCR analysis, genes and primers presented in Table 2 were used.

Figure 3:
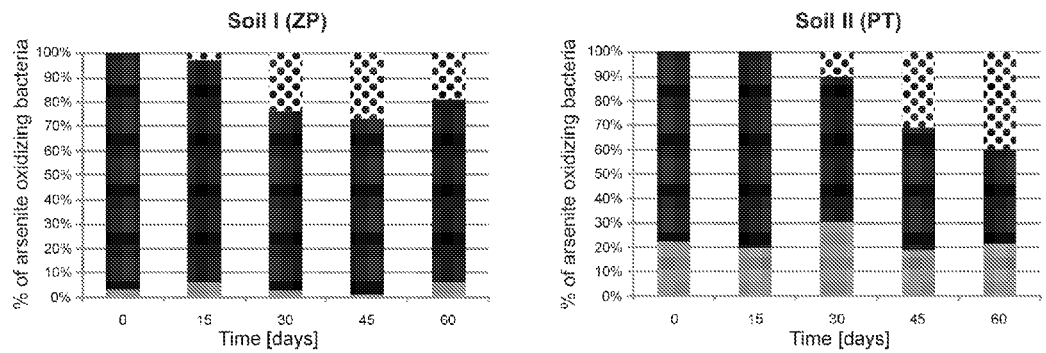
FIG. 3. Shows a graph illustrating the frequency of conjugative transfer of the plasmid pSinA from the cells of the *Sinorhizobium* sp. M14 strain to the cells of indigenous bacteria. In the experiment, two soil samples were used: (I) coming from the Zloty Potok area and designated as ZP and (II) coming from Potok Trujaca and designated as PT. ■—indicates the *Sinorhizobium* sp. M14 strain (donor of the plasmid pSinA); ■—indigenous microflora, capable of arsenite oxidation, comprising bacteria of the genera: *Brevundimonas* sp., *Stenotrophomonas* sp., and *Pseudomonas* sp. for the soil I (ZP) and (ii) *Achromobacter* sp., *Acidovorax* sp., *Acinetobacter* sp. *Brevundimonas* sp., *Microbacterium* sp., *Pseudomonas* sp., and *Stenotrophomonas* sp. for the soil II (PT); ▒—transconjugants harbouring the plasmid pSinA—derivatives of the indigenous bacteria, including bacteria of the genus *Sinorhizobium* sp. and *Pseudomonas* sp. for the soil I (ZP) and *Brevundimonas* sp., *Sinorhizobium* sp. and *Pseudomonas* sp. for the soil II (PT).

After 60 days of cultivation, in both soil samples, transconjugants harbouring the plasmid pSinA were identified. Depending on the type of soil, transconjugants constituted for 25-40% of all arsenite-oxidising bacteria isolated from microcosms (FIG. 3). In Table 3 below, a list of identified strains, to which the plasmid pSinA has been introduced, has been presented.

TABLE 3

Taxonomic classification of the obtained soil transconjugants harbouring the plasmid pSinA

| Name of the strain | Taxonomic group | Similarity to the sequences deposited in the GenBank database (GenBank no) and identity[%] |
|---|---|---|
| Soil transconjugants harbouring the plasmid pSinA, isolated from the soil ZP (I) | | |
| SZP1 | Alphaproteobacteria | *Ensifer adhaerens* strain REG34 (EU647697.1) [100%] |
| SZP2 | Alphaproteobacteria | *Sinorhizobium* sp. S1-2B (AY505137.1) [99%] |
| SZP3 | Alphaproteobacteria | *Sinorhizobium* sp. TB8-2 (AY505141.1) [99%] |
| SZP4 | Gammaproteobacteria | *Pseudomonas marginalis* strain LMG 2238 (HE586396.1) [97%] |
| Soil transconjugants harbouring the plasmid pSinA, isolated from the soil PT (II) | | |
| SPT1 | Gammaproteobacteria | *Pseudomonas* sp. PSA A4(4) (DQ628969.1) [97%] |
| SPT2 | Gammaproteobacteria | *Pseudomonas jessenii* strain Gd4F (GU391474.1) [99%] |
| SPT3 | Gammaproteobacteria | *Pseudomonas* sp. BIHB 813 (EF437218.1) [99%] |
| SPT4 | Alphaproteobacteria | *Brevundimonas* sp. sp. CCBAU (JF772569.1) [99%] |
| SPT5 | Gammaproteobacteria | *Pseudomonas* sp. OS8 (EF491958.1) [99%] |

Among the transconjugants harbouring the pSinA plasmid, there are strains classified as Alpha- and Gammaproteobacteria. All the constructed strains were capable of arsenite oxidation and of using them as an electron donor (energy source), and stably maintained the plasmid pSinA (after about 60 generations of growth in a medium without selection pressure).

The obtained results indicate the possibilities of a horizontal transfer of arsenic metabolism genes using the plasmid pSinA. This plasmid can be transferred between species belonging to Alphaproteobacteria and Gammaproteobacteria due to the presence of a broad host range replication system and conjugational transfer system. Due to the presence of a set of genes responsible for the arsenite metabolism, the strains harbouring the plasmid pSinA are characterised by high tolerance to arsenic compounds and are capable of arsenite oxidation.

Example 5

Analysis of the Accumulation of Arsenic by the Strains Harbouring the Plasmid pSinA and Oxidation Performance Analysis Oxidation performance analysis was carried out for the *Sinorhizobium* sp. M14, *A. tumefaciens* KKP 2039p (D10) and *P. alcaliphilus* KKP 2040p (C10) strains. Growth experiment and the performance analysis were carried out in MSM medium, enriched with arsenites as the sole source of energy, at 22° C. for 120 hours. From culture fluids, initially containing 5 mM (375 ppm) of sodium arsenite, samples were collected every 24 hours, and As(III) and As(V) content was determined (Drewniak et al., 2008).

The performance analysis of arsenite oxidation to arsenates revealed, that the initial *Sinorhizobium* sp. M14 strain completely oxidizes arsenites to arsenates, which are partially removed out of the cell, and partially accumulated inside the cell. Of the initial concentration of 388 mg/L of As(III), after 120 hours of incubation, 155 mg/L of As (V) remained (FIG. 4), which, as the As (III) content was zero, indicates that part of arsenic is accumulated in/on the *Sinorhizobium* sp. M14 cells. In order to verify whether the *Sinorhizobium* sp. M14 strain accumulates arsenic, cells cultured in MSM medium supplemented with arsenites were observed under transmission electron microscope (TEM) and were subjected to X-ray analysis. It was observed that, in the M14 cells, circular granules of high electron density are present (FIG. 5). All the cells cultured in medium supplemented with arsenic contained at least two "granules" each, and more than 90% contained three to five of them. No granules were observed in the cells cultured in medium without the addition of arsenic. The conducted analysis showed that the granules present in the *Sinorhizobium* sp. M14 cells contain mainly arsenic, iron and molybdenum (FIG. 5).

Figure 4:
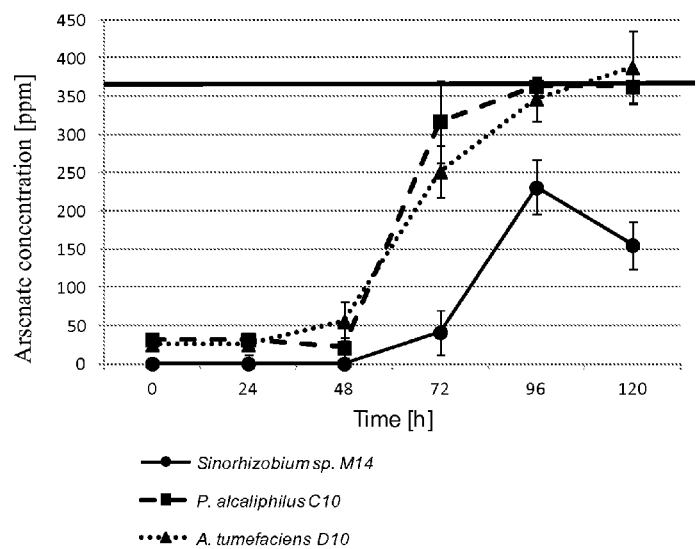
FIG. 4. Shows a comparison of the efficiency of arsenite removal out of the cell carried out by the wild-type strain
Figure 5:
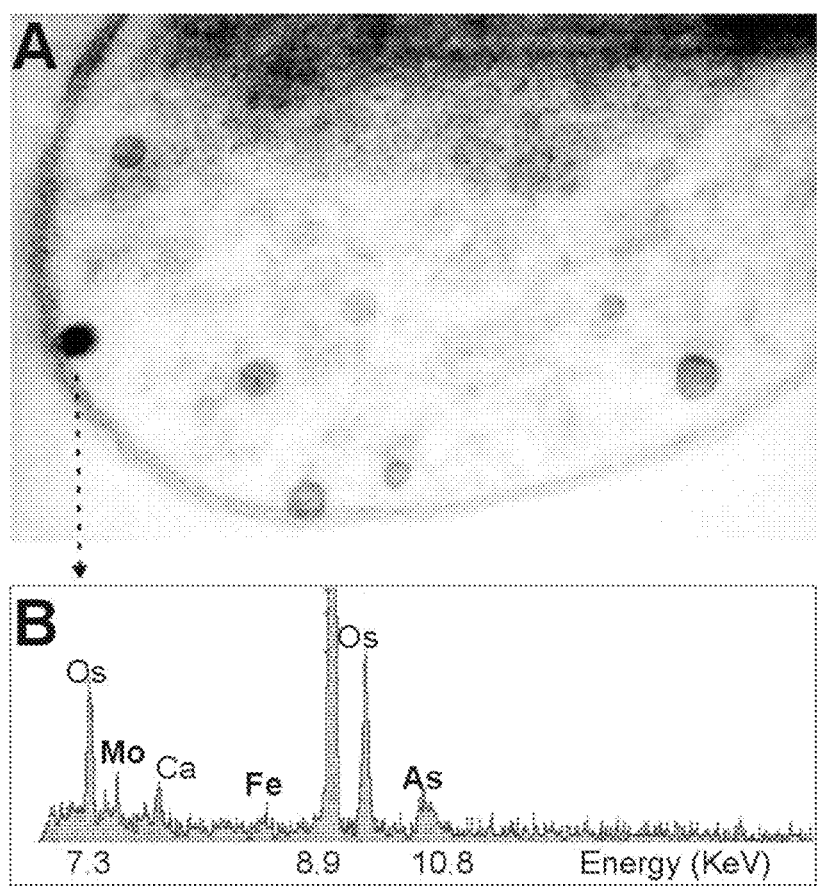

Oxidation performance analysis of the *A. tumefaciens* KKP 2039p and *P. alcaliphilus* KKP 2040p strains showed, that both strains, after 120 hours of cultivation, completely oxidize arsenites to arsenates, all of which are removed out of the cell (FIG. 4). On the basis of the data obtained, it has been found that, unlike the *Sinorhizobium* sp. M14 strain, from which the plasmid pSinA originates, the *Agrobacterium tumefaciens* KKP 2039p, and *Paracoccus alcaliphilus* KKP 2040p strains, do not accumulate arsenic in their produced biomass and they show increased efficiency of oxidation of As (III) to As (V).

Example 6

Introduction of the Plasmid to the Cells of Indigenous Microflora of Arsenic Contaminated Environments by Means of Bioaugmentation with the *A. tumefaciens* KKP 2039p (D10) Strain In order to demonstrate that the newly constructed *A. tumefaciens* KKP 2039p strain and the plasmid pSinA introduced into its cells can be used in bioaugmentation of the indigenous microflora of arsenic contaminated environments, an experiment was conducted on soil samples coming from the gold mine area in Zloty Stok, designated as ZP (I). The experiment was carried out for 15 days in 100 ml of liquid MSM medium (Drewniak et al., 2008), supplemented with 10 g of non-sterile soil, to which *A. tumefaciens* KKP 2039p was added. After 15 days of incubation at room temperature, samples of soil were collected and the bacteria were plated on solid MSM medium with 5 mM sodium arsenite. The grown cultures were passaged to LB medium with 5 mM As(III) and to liquid MSM medium with 5 mM of As(III). In order to verify whether the grown colonies (potential transconjugants) harbour the plasmid pSinA, their ability to oxidize As(III) was tested in modified MSM medium. All strains [the donor (*A. tumefaciens* KKP 2039p) and potential transconjugants] capable of arsenite oxidation were then subjected to detailed analyses: (i) verification of the presence of the plasmid pSinA through the identification of plasmid pSinA genes (aoxB, repA, traI, orf12) in the genomes of potential transconjugants using PCR; (ii) identification of the donor strain (*A. tumefaciens* KKP 2039p) and transconjugants, by analysis of restriction fragments of 16S rRNA genes (iii) visualization of plasmids and megaplasmids of potential transconjugants. For PCR analysis, genes and primers presented in Table 2 were used. The frequency of plasmid pSinA transfer from the cells of *A. tumefaciens* KKP 2039p to the cells of indigenous bacteria is shown in FIG. 6.

Example 7

Introduction of the Plasmid to the Cells of Indigenous Microflora of Arsenic Contaminated Environments by Means of Bioaugmentation with *P. alcaliphilus* KKP 2040p In order to demonstrate that the newly constructed *P. alcaliphilus* KKP 2040p strain and the plasmid pSinA introduced into its cells can be used in bioaugmentation of the indigenous microflora of arsenic contaminated environments, an experiment was conducted on soil samples coming from the gold mine area in Zloty Stok, designated as ZP (I). The experiment was carried out for 15 days in 100 ml of liquid MSM medium (Drewniak et al., 2008), supplemented with 10 g of non-sterile soil, to which *P. alcaliphilus* KKP 2040p was added. After 15 days of incubation at room temperature, samples of soil were collected and the bacteria were plated on solid MSM medium with 5 mM sodium arsenite. The grown cultures were passaged to LB medium with 5 mM As(III) and to liquid MSM medium with 5 mM of As(III). In order to verify whether the grown colonies (potential transconjugants) harbour the plasmid pSinA, analyses were carried out as in Example 6. The frequency of plasmid pSinA transfer from the cells of *P. alcaliphilus* KKP 2040p to the cells of indigenous bacteria is shown in FIG. 6.

Example 8

Construction of the Vector Carrying a Gene Module Coding for the Proteins Involved in Arsenite Oxidation and Its Use for the Production of Strains Capable of Oxidizing Arsenites In order to demonstrate, which genes located on plasmid pSinA (SEQ ID NO: 1) encode proteins responsible for arsenite oxidation, the aio module, comprising aioXSRAB-moeA genes, was cloned in the vector pBBR1-MCS2 (Km$^r$), in the *Escherichia coli* TOP10 strain, and then its functionality was tested.

In order to clone the aio module, amplification of a DNA fragment of the size 10077 by (comprising the region from position 24376 to 34453 in the genome of pSinA) was performed on a DNA template of the plasmid pSinA, isolated by alkaline lysis. For PCR reaction, the following oligonucleotides were used as primers:
AIOf_XbaI: ggtggc*tctaga* CAGCGGCTTCACACAT-AGTCCCCAG [position in the genome of plasmid pSinA: 24376-24400; the underlined sequence is the restriction site recognized by the enzyme XbaI (TCTAGA)], and
AIOr_Bsu15: ggt*TCGAT* GCACCCACGATGGCGAGAG [position in the genome of plasmid pSinA: 34430-34453; the underlined sequence is the restriction site recognized by the enzyme BsuRI (ClaI) (ATCGAT)] For the amplification, Phusion® High-Fidelity DNA Polymerase (Thermo Scientific) was used.

The obtained PCR product (10077 bp) was cloned into a plasmid vector: pBBR1MCS-2 (Km$^r$) (Kovach et al., 1995) digested (linearized) with SmaI. The ligation mixture of the PCR product and the vector pBBR1MCS2 digested with the enzyme SmaI (CCC↓GGG) was introduced, by means of chemical transformation, using the calcium-rubidium method according to Kushner (1978), into the cells of *Escherichia coli* Top10 strain [mcrA Δmrr-hsdRMS-mcrBC) φ80lacZΔM15 ΔlacX74 recA1 araD139 Δ(ara-leu)7697 galU galK rpsL endA1 nupG]. As the selection medium, complete LB medium with kanamycin (30 µg/ml), IPTG (0.5 µg), and X-gal (40 µg/ml) was used.

From the pool of the obtained transformants (white colonies resistant to kanamycin) strains that were harbouring a plasmid of the appropriate size: 15221 bp [pBBR1MCS2 (5144 bp)+aio module–(10077 bp)] were selected. The presence of the constructed plasmid was confirmed by electrophoretic analysis and sequencing. The *Escherichia coli* AIO strain (derivative of the *E. coli* TOP10 strain), harbouring the plasmid pAIO1 (derivative of pBBR1MCS2 with cloned aio module), was selected for further analysis.

In order to demonstrate that the constructed plasmid pAIO1 can be used for constructing strains capable of arsenite oxidation, the plasmid pAIO1 was introduced into 5 strains belonging to Alphaproteobacteria, Betatproteobacteria and Gammaproteobacteria. For the construction, the following strains were selected:
(i) *Agrobacterium tumefaciens* LBA288 and *Paracoccus aminovorans* JCM7685 (Alphaproteobacteria) as well as *Stenotrophomonas* sp. LM24R (Gammaproteobacteria) incapable of arsenite oxidation and susceptible to As (III) (1 mM of sodium arsenite inhibits the growth of these strains),
(ii) *Brevundimonas* sp. OS24R (Alphaproteobacteria) and *Pseudomonas* sp. OS29R (Gammaproteobacteria) incapable of arsenite oxidation, but resistant to As (III).

As the method for introducing plasmid DNA, triparental mating, described in Sambrook and Russel, 2001, was used. The *E. coli* AIO strain, harbouring the plasmid pAIO1, carrying the genes for arsenite oxidase and determining kanamycin resistance, was used as the donor. The prepared cultures of the donor (*E. coli* AIO with the plasmid pAIO1), the helper strain (*E. coli* TG1 with the plasmid pRK2013) and the recipient (*A. tumefaciens* LBA288, *P. aminovorans* JCM7685, *Stenotrophomonas* sp. LM24R, *Brevundimonas* sp. OS24R, and *Pseudomonas* sp. OS29R) were mixed in a ratio 1:1:2, and then 100 µl of the mixture were plated on LB. After 24-hour incubation at 30° C., bacterial colonies were washed off the surface of the petri dish with 2 ml of saline solution, and appropriate dilutions ($10^0$-$10^{-3}$) were plated on selective LB medium, supplemented with kanamycin (50 µg/ml), which eliminates the cells of the recipient, and rifampicin (50 µg/ml), which allows for the elimination of the cells of the donor strain and of the strain harbouring the helper plasmid. They were subsequently incubated for 48 h at 30° C. Potential transconjugants were subjected to the following analyses:
(i) verification of the restriction pattern of 16S rRNA genes [isolation of DNA, amplification of 16S rRNA genes using primers 27F and 1492R (Lane, 1991), digestion with the restriction enzyme HaeIII, DNA electrophoresis],
(ii) analysis for the presence of the plasmid pAIO1 in the transconjugant cells (alkaline lysis and visualization during DNA electrophoresis),
(iii) PCR analysis for the presence of arsenite oxidase genes (DNA amplification using primers aoxBF and aoxBR, and electrophoretic analysis of DNA),
(iv) physiological analysis to determine the ability to oxidize As (III) in modified MSM medium (Drewniak et al., 2008) according to the description presented in Example 2A.

In all the conjugations, transconjugants harbouring the plasmid pAIO1 were obtained. Physiological analysis with the AgNO$_3$ test revealed that all derivatives of the wild-type strains, previously incapable of arsenite oxidation, acquired the ability to oxidize arsenites with the introduction of the plasmid pAIO1 [all strains oxidized As(III) to As(V) and a brown precipitate formed in the reaction with AgNO$_3$].

In order to confirm that the newly constructed strains, harbouring the plasmid pAIO1, are capable of arsenite oxidation, an analysis of As(III) oxidation efficiency was carried out, on the example of *Agrobacterium tumefaciens* AIO1 (derivative of *A. tumefaciens* LBA288 harbouring the plasmid pAIO1) and *Paracoccus aminovorans* AIO2 (derivative of *P. aminovorans* JCM7685 harbouring the plasmid pAIO1). Wild-type strains were used as the control. The growth experiment and the performance analysis were carried out in MSM medium, enriched with arsenites as the sole source of energy, and with 0.004% yeast extract as the source of vitamins, at 30° C. for 96 hours. From culture fluids, initially containing 2 mM (150 ppm) of sodium arsenite, samples were collected every 24 hours, and As(III) and As(V) content was determined (Drewniak et al., 2008).

The performance analysis of oxidation of As(III) to As(V) (FIG. 7) revealed, that the strains harbouring the plasmid pAIO1 are capable of complete arsenite oxidation and production of arsenates already within 72 hours from the beginning of the culture. On the other hand, wild-type strains deprived of the plasmid pAIO1 are not capable of growth and arsenite oxidation, and thus, of producing arsenates.

The conducted experiments made it possible to confirm that the derivative of the plasmid pSinA, comprising the aio module (sequence from 24376 to 34453) can be used for constructing strains capable of arsenite oxidation.

Example 9

Construction of a Vector Carrying the Gene Module Coding for the Proteins Involved in Resistance to As (III) and Its Use for the Production of Strains Resistant to Arsenic In order to demonstrate, which genes located on the plasmid pSinA (SEQ ID NO: 1) encode proteins responsible for the resistance to arsenites, the ars module, comprising arsR1C1C2BtrkAmsfarsHarsR2 genes, was cloned in the vector pBBR1-MCS2 (Km$^r$), in the *Escherichia coli* TOP10 strain, and then its functionality was tested.

In order to clone the ars module, amplification of a DNA fragment of the size 7544 by (comprising the region from position 43229 to 50772 in the genome of pSinA) was performed on a DNA template of the plasmid pSinA, isolated by alkaline lysis. For PCR reaction, the following oligonucleotides were used as primers:

ArsF_Bsu15: ggtggt*ATCGAT* GAAAAGCAGGCAGAG-GCC [position in the genome of the plasmid pSinA: 43229-43523; the underlined sequence is the restriction site recognized by BsuRI (ClaI) (ATCGAT), that is present in the sequence of plasmid pSinA, while the sequence not present in plasmid pSinA was indicated by lower-case letters], and ArsR_Xba: gtt*tctgag* ACACTTCTTGACGTAGCCG-CAACTAACTC [position in the genome of plasmid pSinA: 50744-50772; the underlined sequence is the restriction site recognized by the enzyme XbaI (TCTAGA)] For the amplification, Phusion® High-Fidelity DNA Polymerase (Thermo Scientific) was used.

The obtained PCR product (7544 bp) was digested with the enzymes Bsu15I and XbaI, and subsequently, was cloned into the vector pBluescriptKSII(+) (Stratagene) previously cleaved with the restriction enzymes Bsu15I and XbaI. The ligation mixture of the PCR product and the vector pBluescriptKSII(+) was introduced, by means of chemical transformation, using the calcium-rubidium method according to Kushner (1978), into the cells of *Escherichia coli* TOP10F' strain: F' {lacIqTn10(TetR)} mcrA Δ(mrr-hsdRMS-mcrBC) Φ80lacZΔM15 ΔlacX74 recA1 araD139 Δ(ara-leu)7697 galU galK rpsL endA1 nupG. As the selection medium, complete LB medium with ampicillin (150 μg/ml), IPTG (0.5 μg), X-gal (40 μg/ml) was used. From the pool of the obtained transformants (white colonies resistant to ampicillin), the strains that were harbouring a plasmid of the appropriate size: 10456 bp (pBluescriptKSII(+)–2912+ars module–7544 bp) were selected. The presence of the constructed plasmid was confirmed by electrophoretic analysis and sequencing. The *Escherichia coli* ARS1 strain (derivative of *E. coli* TOP10F' strain) harbouring the plasmid pKS_Ars (derivative of pBluescriptKSII with cloned ars module), was selected for further analysis.

As the use of the plasmid pBluescriptKSII is limited to the strains of *Escherichia coli* as the only host, ars module was cloned into the broad-host-range plasmid pCM62, carrying resistance to tetracycline (Marx and Lindstrom, 2001). For this purpose, the plasmid pKS_Ars (isolated from *Escherichia coli* ARS1 by alkaline lysis) was digested with the restriction enzymes VspI, XbaI. Subsequently, the obtained DNA fragment of the size of 7742 bp, containing the module ars, was cloned into the vector pCM62 previously digested with the enzymes VspI and XbaI. The ligation mixture of the DNA fragment of the plasmid pKS-Ars (containing the ars module) and the vector pCM62 was introduced, by means of chemical transformation, into the cells of *Escherichia coli* TOP10F strain [F-mcrA Δ(mrr-hsdRMS-mcrBC) φ80lacZAM15 ΔlacX74 nupG recA1 araD139 Δ(ara-leu) 7697 galE15 galK16 rpsL(Str$^R$) endA1 λ$^-$]. As the selection medium, complete LB medium with tetracycline (10 μg/ml) was used. From the pool of the obtained transformants (colonies resistant to tetracycline), the strains that were harbouring a plasmid of the appropriate size: 14407 bp (pCM62–6863 bp+ars module–7544 bp) were selected. The presence of the constructed plasmid was confirmed by electrophoretic analysis and sequencing. The *Escherichia coli* ARS2 strain (derivative of *E. coli* TOP10F strain) harbouring the plasmid pARS1 (derivative of pCM62 with cloned ars module), was selected for further analysis.

In order to demonstrate that the constructed plasmid pARS1 can be used for constructing strains with increased resistance to arsenic, the plasmid pARS1 was introduced into *Agrobacterium tumefaciens* LBA288, susceptible to As (III) (1 mM of sodium arsenite inhibits the growth of LBA2888 cells), *Paracoccus aminophilus* JCM7686 showing low resistance to As(III) (5 mM of sodium arsenite inhibits the growth of the cells of the JCM7686 strain), and *Brevundimonas* sp. OS24R showing high resistance to As (III) (10 mM of sodium arsenite inhibits the growth of OS24R cells). As the method for introducing plasmid DNA, triparental mating, described in Sambrook and Russel, 2001, was used. The *E. coli* ARS1 strain, which harbours the plasmid pARS1, carrying the genes for arsenite oxidase and determining resistance to tetracycline, was used as the donor. The prepared cultures of the donor (*E. coli* ARS1 with the plasmid pARS1), the helper strain (*E. coli* TG1 with the plasmid pRK2013) and the recipient (*Agrobacterium tumefaciens* LBA288, *Brevundimonas* sp. OS24R, *P. aminophilus* JCM7686) were mixed in a ratio 1:1:2, and then 100 μl of the mixture were plated on LB. After 24-hour incubation at 30° C., bacterial colonies were washed off the surface of the petri dish with 2 ml of saline solution, and appropriate dilutions ($10^0$-$10^{-3}$) were plated on selective LB medium, supplemented with tetracycline (10 μg/ml), which eliminates the cells of the recipient, and rifampicin (50 μg/ml), which allows for the elimination of the cells of the donor strain and of the strain harbouring the helper plasmid. They were subsequently incubated for 48 h at 30° C. Potential transconjugants were subjected to the following analyses:

(i) verification of the restriction pattern of 16S rRNA genes [isolation of DNA, amplification of 16S rRNA genes using primers 27F and 1492R (Lane, 1991), digestion with the restriction enzyme HaeIII, DNA electrophoresis], (ii) analysis for the presence of the plasmid pARS1 in the transconjugant cells (alkaline lysis and visualization during DNA electrophoresis), (iii) PCR analysis for the presence of cytoplasmic arsenate reductase genes [DNA amplification using primers ParsH-L (TGACGTAGCCGCAACTAACT-position in the genome of pSinA:50745-50764) and ParsH-P (TGGCTTGTGCTGCGAATAAG-position in the genome of pSinA: 50155-50174) and electrophoretic analysis of DNA].

In all the conjugations, transconjugants harbouring the plasmid pARS1 were obtained. To confirm that the newly constructed strains, harbouring the plasmid pARS1, have an increased resistance to arsenic, analysis of MIC—minimal concentration of As(III), inhibiting the growth of the following strains: *Agrobacterium tumefaciens* ARS3 (derivative of *A. tumefaciens* LBA288 harbouring the plasmid pARS1), *Brevundimonas* sp. ARS4 (derivative of *Brevundimonas* sp. sp. OS24R harbouring the plasmid pARS1), *P. aminophilus* ARS5 (derivative of *P. aminophilus* JCM7686 harbouring the plasmid pARS1) was carried out. Wild-type strains were used as the control. Growth experiment and MIC analysis for As(III) was carried out in LB medium, with various concentrations of sodium arsenite (up to 20 mM). After 48 h of cultivation at 30° C., optical density of cultures at $OD_{600nm}$ was monitored. The conducted analysis revealed that all the investigated strains harbouring the plasmid pARS1 increased their tolerance to the presence of sodium arsenite, in relation to their related wild-type strains (FIG. 8). MIC for As(III) for *A. tumefaciens* LBA288 strain was 1 mM, while for its derivative, comprising the plasmid pARS1, 20 mM; for *P. aminophilus* JCM7686R strain 5 mM, while for its derivative, containing the plasmid pARS1, 20 mM. In turn *Brevundimonas* sp. OS24R could tolerate the maximum of 10 mM of As(III), and its derivative harbouring the plasmid pARS1 was resistant to 20 mM of As(III). The conducted analyses allowed to confirm that the derivative of the plasmid pSinA, comprising the ars module (sequence from 43229 to 50772) can be used for constructing strains with increased resistance to arsenic.

In the presented embodiments, the inventors have demonstrated the possibility of using a natural, genetically unmodified plasmid pSinA of its functional derivatives for constructing strains capable of arsenite oxidation, particularly preferably strains not accumulating arsenic compounds. Novel strains were produced: *Agrobacterium tumefaciens* (D10), deposited under the number KKP 2039p and *Paracoccus alcaliphilus* (C10) deposited under the number KKP 2040p, which do not accumulate arsenic, and do not store it in their produced biomass, and are characterized by an increased efficiency of oxidation of As (III) to As (V). It was unexpectedly found, that the use of the pSinA plasmid or its functional derivatives is not limited to strains originally capable of arsenite oxidation. Strains that are completely incapable of arsenite oxidation, acquire this ability with the acquisition of the pSinA plasmid. Introduction of the plasmid pSinA into the cells of the host, ensures their acquisition of resistance to arsenites and arsenates, as well as to other heavy metals.

Moreover, it was demonstrated, that the application of the *Agrobacterium tumefaciens* KKP 2039p, *Paracoccus alcaliphilus* KKP 2040p or *Sinorhizobium* sp. M14 strains, and other strains harbouring the plasmid pSinA, in the removal of arsenic by in situ methods and based on oxidation of As (III) to As (V), ensures the stability of this process. If the introduced strains will not be able to survive in the new conditions, then through the horizontal gene transfer they will pass the plasmid to the cells of indigenous microflora, and this, in turn, will ensure their capability of arsenite oxidation in a specific environment.

It was also demonstrated that the nucleotide sequence corresponding to nucleotides 24376-34453 in SEQ ID NO: 1 or its functional derivative, which contains the aio module of pSinA, gives the bacterial strains, to which it was introduced, the ability to oxidize arsenites and/or produce arsenates, and therefore this derivative of the plasmid pSinA can be used for producing bacterial strains, which after the introduction of such a sequence acquire the ability to oxidize arsenites and/or produce arsenates and can be used in applications that require such strains.

It was also demonstrated that the nucleotide sequence corresponding to nucleotides 43229-50772 in SEQ ID NO: 1 or its functional derivative, which contains the ars module of pSinA, gives the bacterial strains, to which it was introduced, an increased resistance to arsenic, and therefore this derivative of the plasmid pSinA can be used for producing bacterial strains, which after the introduction of such a sequence increase their resistance to arsenic and can be used in applications that require such strains.

LITERATURE CITED IN THE DESCRIPTION, INCLUDED HEREIN AS REFERENCES

Bartosik, D., Baj, J., Piechucka, E., Waker, E., and Wlodarczyk, M. 2002. Comparative characterization of repABC-type replicons of *Paracoccus pantotrophus* composite plasmids. *Plasmid* 48: 130-141

Chwirka J. D., B. M. Thomson and J. M. Stomp. 2000. Removing arsenic from groundwater. *J. Am. Water Works Assoc.* 92:79-88.

Ditta G., S. Stanfield, D. Corbin i D. R. Helinski. 1980. Broad host range DNA cloning system for gram-negative bacteria: construction of a gene bank of *Rhizobium meliloti*. *Proc. Natl. Acad. Sci. USA* 77:7347-51.

Drewniak, L., 2009. Characterization of arsenic bacteria isolated from Zloty Stok gold mine. PhD thesis. Laboratory of Environmental Pollution Analysis, University of Warsaw. Warsaw Drewniak, L., Matlakowska, R., Sklodowska, A., 2008. Arsenite and arsenate metabolism of *Sinorhizobium* sp. M14 living in the extreme environment of the Zloty Stok gold mine. *Geomicrobiology Journal* 25 (7-8), 363-370.

Drewniak, L., Matlakowska, R., Rewerski, B., Sklodowska, A., 2010. Arsenic release from gold mine rocks mediated by the activity of indigenous bacteria. *Hydrometallurgy* 104, 437-442.

Driehaus W., R. Seith and M. R. Jekel. 1995. Oxidation of arsenic(III) with manganese oxides in water treatment. *Water Res.* 29:297-305.

Hooykaas, P. J. J., den Dulk-Ras, H., Schilperoort, R. A. 1980. Molecular mechanism of Ti plasmid mobilization by R plasmids: isolation of Ti plasmids with transposon-insertions in *Agrobacterium tumefaciens*. *Plasmid* 4: 64-75.

Kostal J., R. Yang, C. H. Wu, A. Mulchandani and W. Chen. 2004. Enhanced arsenic accumulation in engineered bacterial cells expressing ArsR. *Appl. Environ. Microbiol.* 70:4582-7.

Kovach M. E., Elzer P. H., Hill D. S., Robertson G. T., Farris M. A., Roop R. M. and K. M. Peterson. 1995. Four new derivatives of the broad-host-range cloning vector pBBR1MCS, carrying different antibiotic-resistance cassettes. *Gene* 166:175-176

Lievremont D., A. N'Negue M, P. Behra and M. C. Lett. 2003. Biological oxidation of arsenite: batch reactor experiments in presence of kutnahorite and chabazite. *Chemosphere* 51:419-28.

Pattanayak J., K. Mondal, S. Mathew and S. B. Lalvani. 2000. A parametric evaluation of the removal of As(V) and As(III) by carbon-based adsorbents. *Carbon* 38:589-596.

Sambrook, J., Russell, D. W., 2001. Molecular Cloning: A Laboratory Manual. Cold Spring Harbor Laboratory Press, New York.

Simeonova D. D., K. Micheva, D. A. Muller, F. Lagarde, M. C. Lett, V. I. Groudeva and D. Lievremont. 2005. Arsenite oxidation in batch reactors with alginate-immobilized ULPAs1 strain. *Biotechnol. Bioeng.* 91:441-6.

Tripathi R. D., S. Srivastava, S. Mishra, N. Singh, R. Tuli, D. K. Gupta and F. J. Maathuis. 2007. Arsenic hazards: strategies for tolerance and remediation by plants. *Trends Biotechnol.* 25:158-65.

Wilkie J. A. and J. G. Hering. 1998. Rapid oxidation of geothermal arsenic(III) in streamwaters of the eastern Sierra Nevada. *Sci. Technol.* 657-662.

Yang C, Xu L, Yan L, Xu Y. (2010) Construction of a genetically engineered microorganism with high tolerance to arsenite and strong arsenite oxidative ability. *J Environ Sci Health A Tox Hazard Subst Environ Eng.;* 45(6):732-7.

The invention is further described by the following numbered paragraphs:

1. A novel strain *Agrobacterium tumefaciens* deposited in the IAFB Collection of Industrial Microorganisms of Institute of Agricultural and Food Industry under the number KKP 2039p.
2. A novel strain *Paracoccus alcaliphilus* deposited in the The IAFB Collection of Industrial Microorganisms of Institute of Agricultural and Food Industry under the number KKP 2040p.
3. A plasmid pSinA shown in SEQ ID NO: 1 and its functional derivative.
4. A method for producing bacterial strains capable of chemolithotrophic arsenite oxidation, comprising the following steps:
   a) obtaining the recipient strain;
   b) introduction of the plasmid pSinA, shown in SEQ ID NO: 1, or its functional derivative into the recipient strain.
5. The method according to paragraph 4, characterized in that, the step b) is carried out by:
   (i) triparental mating with the use of a donor strain harbouring the plasmid pSinA, shown in SEQ ID NO: 1 or its functional derivative, and a helper strain harbouring a helper plasmid, or,
   (ii) biparental mating with the use of a donor strain harbouring the plasmid pSinA shown in SEQ ID NO: 1 or its functional derivative.
6. The method according to paragraph 4 or 5, characterised in that the donor strain is *Agrobacterium tumefaciens* deposited under the number KKP 2039p or *Paracoccus alcaliphilus* deposited under the number KKP 2040p.
7. The method for producing bacterial strains according to paragraph 4, wherein in the step a) of the obtaining the recipient strain, a gene encoding a selection marker is additionally introduced into the recipient strain, preferably encoding antibiotic resistance.
8. The method for producing bacterial strains according to paragraph 7, wherein the gene encoding the additional selection marker is introduced on a plasmid, preferably by triparental mating with a bacterial strain harbouring the plasmid containing the gene encoding the additional selection marker and with a helper strain harbouring a helper plasmid.
9. The method according to claims 4-8, wherein the recipient strain is a bacterial strain isolated from natural environment, preferably from arsenic contaminated environment.
10. The method according to claims 4-9, wherein the recipient strain is a bacterial strain belonging to Alphaproteobacteria or Gammaproteobacteria.
11. A novel bacterial strain capable of chemolithotrophic arsenite oxidation, produced by the method according to claims 4-10.
12. A composition comprising the novel bacterial strain according to claims 1-2, the novel bacterial strain according to paragraph 11, the plasmid according to paragraph 3 or combination thereof.
13. Use of the novel bacterial strain according to claims 1-2, the novel bacterial strain according to paragraph 11, the plasmid according to paragraph 3, the composition according to paragraph 12, or combination thereof, for constructing bacterial strains capable of chemolithotrophic arsenite oxidation.
14. Use of the novel strain according to claims 1-2, the novel bacterial strain according to paragraph 11, the plasmid according to paragraph 3, the composition according to paragraph 12, or combination thereof, in the processes of biological removal of arsenic.
15. The use according to paragraph 14, characterised in that, the biological removal of arsenic comprises bioremediation, preferably bioaugmentation or biometallurgy of arsenic.
16. A method of bioaugmentation of arsenic contaminated environment, comprising the step of introducing the novel strain according to claim 1-2 or 11, the plasmid according to paragraph 3, the composition according to paragraph 12, or combination thereof, into an arsenic contaminated environment.
17. A method for the removal or recovery of arsenic by chemolithotrophic arsenite oxidation, wherein the step of chemolithotrophic arsenite oxidation is carried out by the novel strain defined in claims 1-2, the novel strain defined in paragraph 11, the composition defined in paragraph 12, or combination thereof.
18. The method for the removal or recovery of arsenic according to paragraph 17, wherein the step of chemolithotrophic arsenite oxidation is followed by precipitation of the resulting arsenates in the form of insoluble precipitate and/or adsorption of arsenates, wherein the precipitation or adsorption is preferably carried out using burnt lime (CaO), calcium hydroxide $Ca(OH)_2$, bog iron ores or combination thereof.

19. A plasmid comprising the nucleotide sequence corresponding to nucleotides 24376-34453 in SEQ ID NO: 1 or a functional derivative thereof.

20. A bacterial strain comprising the plasmid defined in paragraph 19 or the nucleotide sequence comprising the fragment 24376-34453 of SEQ ID NO: 1 or a functional derivative thereof.

21. Use of the plasmid defined in paragraph 19 or the strain defined in paragraph 20 for arsenite oxidation.

22. A plasmid comprising the nucleotide sequence corresponding to nucleotides 43229-50772 in SEQ ID NO: 1 or a functional derivative thereof.

23. A bacterial strain comprising the plasmid defined in paragraph 22 or the nucleotide sequence comprising the fragment 43229-50772 of SEQ ID NO: 1 or a functional derivative thereof.

24. Use of the plasmid defined in paragraph 22 or the nucleotide sequence comprising the fragment 43229-50772 of SEQ ID NO: 1 or a functional derivative thereof for the production of a strain with increased resistance to arsenic.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated or novel bacteria strain *Agrobacterium tumefaciens* deposited in the IAFB Collection of Industrial Microorganisms of Institute of Agricultural and Food Industry under the number KKP 2039p.

2. A composition comprising the novel bacterial strain according to claim 1.

3. An isolated or novel bacteria strain *Paracoccus alcaliphilus* deposited in the The IAFB Collection of Industrial Microorganisms of Institute of Agricultural and Food Industry under the number KKP 2040p.

4. A composition comprising the novel bacterial strain according to claim 3.

5. An isolated, novel non-naturally occurring bacterial strain capable of chemolithotrophic arsenite oxidation, produced by a method for producing a bacterial strain capable of chemolithotrophic arsenite oxidation, comprising introducing a novel or isolated or non-naturally occurring plasmid pSinA having a nucleotide sequence shown in SEQ ID NO: 1 into the bacterial strain.

6. An isolated, novel non-naturally occurring bacterial strain capable of chemolithotrophic arsenite oxidation according to claim 5, wherein the introducing is carried out by a process comprising:
   (i) triparental mating with the use of a donor strain harbouring the plasmid, and a helper strain harbouring a helper plasmid, or,
   (ii) biparental mating with the use of a donor strain harbouring the plasmid.

7. An isolated, novel non-naturally occurring bacterial strain capable of chemolithotrophic arsenite oxidation according to claim 6 wherein the donor strain is *Agrobacterium tumefaciens* deposited under the number KKP 2039p or *Paracoccus alcaliphilus* deposited under the number KKP 2040p.

8. An isolated, novel non-naturally occurring bacterial strain capable of chemolithotrophic arsenite oxidation according to claim 5, for producing a bacterial strain capable of chemolithotrophic arsenite oxidation, wherein the method of producing includes introducing a gene encoding a selection marker into the bacterial strain.

9. An isolated, novel non-naturally occurring bacterial strain capable of chemolithotrophic arsenite oxidation of claim 8 wherein the selection marker comprises antibiotic resistance.

10. An isolated, novel non-naturally occurring bacterial strain capable of chemolithotrophic arsenite oxidation according to claim 8, wherein the introducing is by a plasmid.

11. An isolated, novel non-naturally occurring bacterial strain capable of chemolithotrophic arsenite oxidation according to claim 10 wherein the Previously Presented plasmid is introduced by triparental mating including a bacterial strain harbouring the plasmid containing the gene encoding the selection marker and a helper strain harbouring a helper plasmid.

12. An isolated, novel non-naturally occurring bacterial strain capable of chemolithotrophic arsenite oxidation according to claim 5 wherein the bacterial strain into which a novel or isolated or non-naturally occurring plasmid pSinA having a nucleotide sequence shown in SEQ ID NO: 1 is introduced is the strain isolated from an arsenic contaminated environment.

13. An isolated, novel non-naturally occurring bacterial strain capable of chemolithotrophic arsenite oxidation according to claim 5, wherein the bacterial strain is an *Alphaproteobacteria* or *Gammaproteobacteria* bacterial strain.

14. A composition comprising the isolated, novel, non-naturally occurring bacterial strain according to any one of claim 6-11 or 5, 12, 13.

15. A composition comprising a novel, non-naturally occurring, isolated bacteria containing a novel or isolated or non-naturally occurring plasmid pSinA having a nucleotide sequence shown in SEQ ID NO: 1 introduced into the bacterial strain.

* * * * *